(12) United States Patent
Harrington et al.

(10) Patent No.: US 8,475,767 B2
(45) Date of Patent: Jul. 2, 2013

(54) ANTI-TRYPANOSOMAL PEPTIDES AND USES THEREOF

(75) Inventors: John M. Harrington, Athens, GA (US); Stephen L. Hajduk, Athens, GA (US)

(73) Assignee: University of George Research Foundation, Inc., Athens, GA (US)

( * ) Notice: Subject to any disclaimer, the term of this patent is extended or adjusted under 35 U.S.C. 154(b) by 0 days.

(21) Appl. No.: 13/282,623

(22) Filed: Oct. 27, 2011

(65) Prior Publication Data
US 2012/0070490 A1 Mar. 22, 2012

Related U.S. Application Data

(63) Continuation-in-part of application No. PCT/US2010/032545, filed on Apr. 27, 2010.

(60) Provisional application No. 61/172,908, filed on Apr. 27, 2009, provisional application No. 61/317,895, filed on Mar. 26, 2010.

(51) Int. Cl.
*A61K 49/00* (2006.01)
*A61K 39/005* (2006.01)

(52) U.S. Cl.
USPC .......................................... 424/9.1; 424/269.1

(58) Field of Classification Search
None
See application file for complete search history.

(56) References Cited

U.S. PATENT DOCUMENTS

| | | | |
|---|---|---|---|
| 5,820,864 A | 10/1998 | Paranhos-Baccala et al. | |
| 2006/0263348 A1 | 11/2006 | Pays et al. | |

FOREIGN PATENT DOCUMENTS

| | | |
|---|---|---|
| WO | WO 01/51072 A2 | 7/2001 |
| WO | WO 01/51072 A3 | 3/2002 |
| WO | WO 2010/129267 A2 | 11/2010 |
| WO | WO 2010/129267 A3 | 2/2011 |

OTHER PUBLICATIONS

Adler et al., "Post-SELEX chemical optimization of a trypanosome-specific RNA aptamer," Jan. 2008, *Comb Chem High Throughput Screen;* 11(1):16-23.
Axler et al., "Apolipoprotein M associates to lipoproteins through its retained signal peptide," Mar. 5, 2008, *FEBS Lett;* 582(5):826-828. Available online on Feb. 13, 2008.
Benach et al., "Phospholipid-induced monomerization and signal-peptide-induced oligomerization of SecA," Feb. 7, 2003, *J Biol Chem;* 278(6):3628-3638. Available online on Oct. 27, 2002.
"Biocompatible Polymers for Solubilization of Hydrophobic Drugs," Bayerische Patentallianz GmbH Innovations Report dated Aug. 19, 2010. Available online [retrieved on Sep. 25, 2012]. Retrieved from the Internet: <http://www.technologieallianz.de/webtemp/B68084jv_nanoformul193128a9.pdf>; 2 pages.
Bishop et al., "Insight into the mechanism of trypanosome lytic factor-1 killing of *Trypanosoma brucei brucei*," Nov. 2001, *Mol Biochem Parasitol;* 118:33-40.
Briggs et al., "Conformations of signal peptides induced by lipids suggest initial steps in protein export," Jul. 11, 1986, *Science;* 233(4760):206-208.
Brun et al., "The phenomenon of treatment failures in Human African Trypanosomiasis," Nov. 2001, *Trop Med Int Health;* 6:906-914.
Bulow et al., "Rapid lateral diffusion of the variant surface glycoprotein in the coat of *Trypanosoma brucei*," Apr. 5, 1988, *Biochem;* 27(7):2384-2388.
Cantor, "The lateral pressure profile in membranes: a physical mechanism of general anesthesia," Nov. 23, 1998, *Toxicol Lett;* 100-101:451-458.
Chattopadhyay and London, "Parallax method for direct measurement of membrane penetration depth utilizing fluorescence quenching by spin-labeled phospholipids," Jan. 1987, *Biochemistry;* 26(1):39-45.
Christoffersen et al., "The signal peptide anchors apolipoprotein M in plasma lipoproteins and prevents rapid clearance of apolipoprotein M from plasma," Jul. 4, 2008, J Biol Chem; 283:18765-18722. Available online on May 5, 2008.
Delgado et al., "Neuropeptides kill African trypanosomes by targeting intracellular compartments and inducing autophagic-like cell death," Mar. 2009, *Cell Death Differ;* 16(3):406-416. Available online on Dec. 5, 2008.
Drain et al., "Haptoglobin-related protein mediates trypanosome lytic factor binding to trypanosomes," Aug. 10, 2001, *J Biol Chem;* 276(32):30254-30260. Available online on May 14, 2001.
Engstler et al., "Kinetics of endocytosis and recycling of the GPI-anchored variant surface glycoprotein in *Trypanosoma brucei*," Mar. 1, 2004, *J Cell Sci;* 117(Pt 7):1105-1115.
Engstler et al., "Hydrodynamic flow-mediated protein sorting on the cell surface of trypanosomes," Nov. 2, 2007, *Cell;* 131(3):505-515.
Ferguson et al., "*Trypanosoma brucei* variant surface glycoprotein has a sn-1,2-dimyristyl glycerol membrane anchor at its COOH terminus," Apr. 25, 1985, *J Biol Chem;* 260(8):4963-4968.
Ferguson et al., "Glycosyl-sn-1,2-dimyristylphosphatidylinositol is covalently linked to *Trypanosoma brucei* variant surface glycoprotein," Nov. 25, 1985, *J Biol Chem;* 260(27):14547-14555.
Field et al., "A glycosylphosphatidylinositol protein anchor from procyclic stage *Trypanosoma brucei:* lipid structure and biosynthesis," Oct. 1991, *EMBO;* 10(10):2731-2739.
Field and Carrington, "The trypanosome flagellar pocket," Nov. 2009, *Nature Rev Microbiol;* 7(11):775-786. Available online on Oct. 6, 2009.
Göringer et al., "In vitro selection of high-affinity nucleic acid ligands to parasite target molecules," Oct. 2003, *Int J Parasitol;* 33(12):1309-1317.
Hager et al., "Endocytosis of a cytotoxic human high density lipoprotein results in disruption of acidic intracellular vesicles and subsequent killing of African trypanosomes," Jul. 1994, *J Cell Biol;* 126(1):155-167.
Hager and Hajduk, "Mechanism of resistance of African trypanosomes to cytotoxic human HDL," Feb. 27, 1997, *Nature;* 385(6619):823-826.
Haines et al., "Killing of trypanosomatid parasites by a modified bovine host defense peptide, BMAP-18," Feb. 2009, *PLoS Negl Trop Dis;* 3(2):e373. Available online on Feb. 3, 2009.
Hajduk et al., "Lysis of *Trypanosoma brucei* by a toxic subspecies of human high density lipoprotein," Mar. 25, 1989, *J Biol Chem;* 264(9):5210-5217.

(Continued)

Primary Examiner — Padma V Baskar
(74) Attorney, Agent, or Firm — Mueting Raasch & Gebhardt, P.A.

(57) ABSTRACT

The present invention provides methods of killing, inhibiting the growth, and/or inhibiting the reproduction of kinetoplastid protozoan with hydrophobic signal sequence peptides and compositions including such hydrophobic signal sequence peptides.

36 Claims, 17 Drawing Sheets

OTHER PUBLICATIONS

Hajduk, Stephen L., "Mechanisms of Resistance and Susceptibility to African Trypanosome Infection," Grant Abstract, Grant No. R01AI039033 [online]. National Institute of Allergy and Infectious Diseases, National Institutes of Health; project dates Feb. 15, 1996 to May 31, 2015 [retrieved on Sep. 25, 2012]. Retrieved from the Internet: <http://projectreporter.nih.gov/pr_Prj_info_desc_dtls.cfm?aid=8274806&icde=13898278&ddparam=&ddvalue=&ddsub=&cr=1&csb=default&cs=ASC&print=yes>; 3 pgs.

Harrington et al., "Membrane permeabilization by trypanosome lytic factor, a cytolytic human high density lipoprotein," May 15, 2009, *J Biol Chem;* 284(20):13505-13512. Available online on Mar. 26, 2009.

Harrington, John, "Killing of African trypanosomes by small hydrophobic peptides: the plasma membrane as a potential drug target," Meeting Abstract for the Heatley-Payne Travel Award Recipient. SGM Spring 2010 Meeting: Systems, Mechanisms and Micro-organisms (Society for General Microbiology Conferences). Edinburgh International Conference Centre: Mar. 29-Apr. 1, 2010. Meeting Abstract Book available online [retrieved on Sep. 25, 2012]. Retrieved from the Internet: <http://www.sgm.ac.uk/meetings/pdfabstracts/edinburgh2010abs.pdf>; Cover page and p. 1.

Harrington et al., "The plasma membrane of bloodstream-form African trypanosomes confers susceptibility and specificity to killing by hydrophobic peptides," Sep. 10, 2010, *J Biol Chem,* 285(37):28659-28666. Available online on Jul. 8, 2010.

Harrington, "Antimicrobial peptide killing of African trypanosomes," Aug. 2011 *Parasite Immunology;* 33:461-469.

Harrington, John, "Novel African Trypanocidal Agents: Membrane interaction and Physiological Effects of Hydrophobic Peptides," Meeting Abstract #3C. Woods Hole, MA: Sep. 11-15, 2011. Abstract available online [retrieved on Sep. 25, 2012]. Retrieved from the Internet: <http://hermes.mbl.edu/mpm/mpm-2011/abstracts/abstract.php?id=198>; 1 page.

Harrington et al., "Novel African trypanocidal agents: membrane rigidifying peptides," Sep. 7, 2012, *PLoS One;* 7:e44384; 7 pages.

Harrington, John M., "Mechanism of Membrane Permeabiltzation by a Cytolytic High Density Lipoprotein," Grant Abstract, Grant No. F32AI080114 [online]. National Institute of Allergy and Infectious Diseases, National Institutes of Health; project dates Aug. 11, 2009 to Aug. 10, 2011 [retrieved on Sep. 25, 2012]. Retrieved from the Internet: <http://projectreporter.nih.gov/pr_Prj_info_desc_dtls.cfm?aid=7919408&icde=13898607&ddparam=&ddvalue=&ddsub=&cr=1&csb=default&cs=ASC&print=yes>; 2 pgs.

Hassett et al., "Characterization of cDNA clones encoding rabbit and human serum paraoxonase: the mature protein retains its signal sequence," Oct. 22, 1991, *Biochemistry;* 30:10141-10149.

Homann and Göringer, "Combinatorial selection of high affinity RNA ligands to live African trypanosomes," May 1, 1999 *Nucleic Acid Res;* 27:2006-2014.

Homann and Göringer, "Uptake and intracellular transport of RNA aptamers in African trypanosomes suggest therapeutic "piggy-back" approach," Oct. 2001 *Bioorg Med Chem;* 9:2571-2580.

Homann et al., "Serum-stable RNA aptamers to an invariant surface domain of live African trypanosomes," Aug. 2006, *Comb Chem High Throughput Screen;* 9(7):491-499.

Jones and Gierasch, "Effect of charged residue substitutions on the membrane-interactive properties of signal sequences of the *Escherichia coli* LamB protein," Oct. 1994 *Biophys J;* 67(4):1534-1545.

Kamaraju and Sukharev, "The membrane lateral pressure-perturbing capacity of parabens and their effects on the mechanosensitive channel directly correlate with hydrophobicity," Oct. 7, 2008, *Biochem;* 47(40):10540-10550. Available online on Sep. 17, 2008.

Koynova and Caffrey, "Phases and phase transitions of the phosphatidylcholines," Jun. 29, 1998, *Biochim Biophys Acta;* 1376(1):91-145.

Lanteri et al., "Roles for the *Trypanosoma brucei* P2 transporter in DB75 uptake and resistance," Nov. 2006, *Mol Pharmacol;* 70(5):1585-1592. Available online on Aug. 15, 2006.

Lee, "How lipids affect the activities of integral membrane proteins," Nov. 3, 2004, *Biochim Biophys Acta;* 1666(1-2):62-87.

Lorger et al., "Targeting the variable surface of African trypanosomes with variant surface glycoprotein-specific, serum-stable RNA aptamers," Feb. 2003, *Eukaryot Cell;* 2(1):84-94.

McGwire et al., "Killing of African trypanosomes by antimicrobial peptides," Jul. 1, 2003, *J Infect Dis;* 188(1):146-152. Available online on Jun. 16, 2003.

McIntosh and Holloway, "Determination of the depth of bromine atoms in bilayers formed from bromolipid probes," Mar. 24, 1987, *Biochemistry;* 26(6):1783-1788.

Morgan et al., "Developmental and morphological regulation of clathrin-mediated endocytosis in *Trypanosoma brucei,*" Jul. 2001, *J Cell Sci;* 114(Pt 14):2605-2615.

Muranjan et al., "Characterization of the human serum trypanosome toxin, haptoglobin-related protein," Feb. 13, 1998, *J Biol Chem;* 273(7):3884-3887.

Nwaka and Ridley, "Virtual drug discovery and development for neglected diseases through public-private partnerships," Nov. 2003, *Nat Rev Drug Discov;* 2:919-928.

Nwaka and Hudson, "Innovative lead discovery strategies for tropical diseases," Nov. 2006, *Nat Rev Drug Discov;* 5:941-95.

Nwaka et al., "Advancing drug innovation for neglected diseases-criteria for lead progression," Aug. 25, 2009, *PLoS Negl Trop Dis;* 3(8):e440; 13 pages.

Oberholzer et al., "Social motility in African trypanosomes," Jan. 29, 2010, *PLoS Pathog;* 6(1):e1000739; 8 pages.

Ochsenreiter and Hajduk, "Alternative editing of cytochrome c oxidase III mRNA in trypanosome mitochondria generates protein diversity," Nov. 2006, *EMBO;* 7(11):1128-1133.

Raper et al., "Characterization of a novel trypanosome lytic factor from human serum," Apr. 1999, *Infect Immun;* 67:1910-1916.

Rodriguez et al., "Propulsion of African trypanosomes is driven by bihelical waves with alternating chirality separated by kinks," Nov. 17, 2009, *Proc Natl Acad Sci USA;* 106(46):19322-19327. Available online on Oct. 30, 2009.

Schmidt, "Trypanosome mystery solved?" Apr. 14, 1995, *Science;* 268:204.

Shiflett et al., "Human high density lipoproteins are platforms for the assembly of multi-component innate immune complexes," Sep. 23, 2005, *J Biol Chem;* 280(38):32578-32585. Available online on Jul. 26, 2005.

Shiflett et al., "African trypanosomes: intracellular trafficking of host defense molecules," Jan.-Feb. 2007, *J Eukaryot Microbiol;* 54(1):18-21.

Smith et al., "Killing of trypanosomes by the human haptoglobin-related protein," Apr. 14, 1995, *Science;* 268(5208):284-286.

Sorenson et al., "Human serum Paraoxonase/Arylesterase's retained hydrophobic N-terminal leader sequence associates with HDLs by binding phospholipids: apolipoprotein A-I stabilizes activity," Sep. 1999, *Arterioscler Thromb Vasc Biol;* 19(9):2214-2225.

Stijlemans et al., "High affinity nanobodies against the *Trypanosome brucei* VSG are potent trypanolytic agents that block endocytosis," Jun. 16, 2011, *PLoS Pathog;* 7(6):e1002072; 15 pages.

Treumann et al., "Structural characterisation of two forms of procyclic acidic repetitive protein expressed by procyclic forms of *Trypanosoma brucei,*" Jun. 20, 1997, *J Mol Biol;* 269(4):529-547.

Tyler et al., "Flagellar membrane localization via association with lipid rafts," Mar. 15, 2009, *J Cell Sci;* 122(Pt 6):859-866. Available online on Feb. 24, 2009.

Universal Protein Resource, UniProt Consortium—collaboration between the European Bioinfonnatics Institute (EBI), Hinxton, Cambridge, UK; the SIB Swiss Institute of Bioinformatics, Geneva, Switzerland; and the Protein Information Resource (PIR), Washington DC, USA. UniProtKB/Swiss-Prot Accession No. O95445, "Apolipoprotein M—*Homo sapiens* (Human)." Available online [retrieved on Sep. 25, 2012]. Retrieved from the Internet: <http://www.uniprot.org/uniprot/O95445>; 9 pgs.

Universal Protein Resource, UniProt Consortium—collaboration between the European Bioinformatics Institute (EBI), Hinxton, Cambridge, UK; the SIB Swiss Institute of Bioinformatics, Geneva, Switzerland; and the Protein Information Resource (PIR), Washington DC, USA. UniProtKB/Swiss-Prot Accession No. P00739, "Haptoglobin-related protein—*Homo sapiens* (Human)." Available online [retrieved on Sep. 25, 2012]. Retrieved from the Internet: <http://www.uniprot.org/uniprot/P00739>; 8 pgs.

Universal Protein Resource, UniProt Consortium—collaboration between the European Bioinformatics Institute (EBI), Hinxton, Cambridge, UK; the SIB Swiss Institute of Bioinformatics, Geneva, Switzerland; and the Protein Information Resource (PIR), Washington DC, USA. UniProtKB/Swiss-Prot Accession No. P27169, "Serum paraoxonase/arylesterase 1—*Homo sapiens* (Human)." Available online [retrieved on Sep. 25, 2012]. Retrieved from the Internet: <http://www.uniprot.org/uniprot/P27169>; 13 pgs.

Vanhollebeke et al., "Distinct roles of haptoglobin-related protein and apolipoprotein L-I in trypanolysis by human serum," Mar. 6, 2007, *Proc Natl Acad Sci USA;* 104(10):4118-4123. Available online on Feb. 26, 2007.

Visconti et al., "Novel signaling pathways involved in sperm acquisition of fertilizing capacity," Jan. 2002, *J Reprod Immunol;* 53(1-2):133-150.

Voglino et al., "Orientation of LamB signal peptides in bilayers: influence of lipid probes on peptide binding and interpretation of fluorescence quenching data," Jun. 8, 1999, *Biochemistry;* 38(23):7509-7516.

Widener et al., "Hemoglobin is a co-factor of human trypanosome lytic factor," Sep. 28, 2007, *PLoS Pathog;* 3(9):e291; 12 pages.

International Preliminary Report on Patentability issued Nov. 1, 2011, in connection with International Patent Application No. PCT/US2010/032545, filed Apr. 27, 2010; 8 pages.

International Search Report mailed Dec. 17, 2010, in connection with International Patent Application No. PCT/US2010/032545, filed Apr. 27, 2010; 5 pages.

Written Opinion mailed Dec. 17, 2010, in connection with International Patent Application No. PCT/US2010/032545, filed Apr. 27, 2010; 7 pages.

Corbett et al., "Response of transplantable tumors of mice to anthracenedione derivatives alone and in combination with clinically useful agents," May 1982, *Cancer Treatment Reports;* 66:1187-1200.

Göringer et al., "RNA aptamers as potential pharmaceuticals against infections with African trypanosomes," 2006, *Handb Exp Pharmacol;* 2006(173):375-393.

Langreth and Balber, "Protein uptake and digestion in bloodstream and culture forms of *Trypanosoma brucei*," Feb. 1975, *J Protozool;* 22(1):40-53.

A

| Peptide | Amino acid sequence |
|---|---|
| SHP-1 | SDLGAVISLLLWGRQLFA |
| SHP-2 | AKLIALTLLGMGLALFRNHQS |
| SHP-1-ΔL | SDLGAVISLLWGRQLFA |
| SHP-1-ΔLLL | SDLGAVISWGRQLFA |
| SHP-1-ΔLGA | SDVISLLLWGRQLFA |
| NSP | ERTEESWGRRFWRRGEAC |

```
                            SEQUENCE LISTING

<160> NUMBER OF SEQ ID NOS: 20

<210> SEQ ID NO 1
<211> LENGTH: 19
<212> TYPE: PRT
<213> ORGANISM: artificial
<220> FEATURE:
<223> OTHER INFORMATION: N-terminal amino acid residues 1-19 of human
      haptoglobulin-related protein

<400> SEQUENCE: 1

Met Ser Asp Leu Gly Ala Val Ile Ser Leu Leu Leu Trp Gly Arg Gln
1               5                   10                  15

Leu Phe Ala

<210> SEQ ID NO 2
<211> LENGTH: 18
<212> TYPE: PRT
<213> ORGANISM: artificial
<220> FEATURE:
<223> OTHER INFORMATION: amino acid sequence of small hydrophobic
      peptide -1 (SHP-1)

<400> SEQUENCE: 2

Ser Asp Leu Gly Ala Val Ile Ser Leu Leu Leu Trp Gly Arg Gln Leu
1               5                   10                  15

Phe Ala

<210> SEQ ID NO 3
<211> LENGTH: 22
<212> TYPE: PRT
<213> ORGANISM: artificial
<220> FEATURE:
<223> OTHER INFORMATION: N-terminal amino acid residues 1-22 of human
      paraoxonase-1 protein

<400> SEQUENCE: 3

Met Ala Lys Leu Ile Ala Leu Thr Leu Leu Gly Met Gly Leu Ala Leu
1               5                   10                  15

Phe Arg Asn His Gln Ser
                20

<210> SEQ ID NO 4
<211> LENGTH: 21
<212> TYPE: PRT
<213> ORGANISM: artificial
<220> FEATURE:
<223> OTHER INFORMATION: amino acid sequence of small hydrophobic
      peptide -2 (SHP-2)

<400> SEQUENCE: 4
```

```
Ala Lys Leu Ile Ala Leu Thr Leu Leu Gly Met Gly Leu Ala Leu Phe
1               5                   10                  15

Arg Asn His Gln Ser
            20

<210> SEQ ID NO 5
<211> LENGTH: 22
<212> TYPE: PRT
<213> ORGANISM: artificial
<220> FEATURE:
<223> OTHER INFORMATION: N-terminal amino acid residues 1-22 of human
      apolipoprotein M

<400> SEQUENCE: 5

Met Phe His Gln Ile Trp Ala Ala Leu Leu Tyr Phe Tyr Gly Ile Ile
1               5                   10                  15

Leu Asn Ser Ile Tyr Gln
            20

<210> SEQ ID NO 6
<211> LENGTH: 21
<212> TYPE: PRT
<213> ORGANISM: artificial
<220> FEATURE:
<223> OTHER INFORMATION: N-terminal amino acid residues 2-22 of human
      apolipoprotein M

<400> SEQUENCE: 6

Phe His Gln Ile Trp Ala Ala Leu Leu Tyr Phe Tyr Gly Ile Ile Leu
1               5                   10                  15

Asn Ser Ile Tyr Gln
            20

<210> SEQ ID NO 7
<211> LENGTH: 17
<212> TYPE: PRT
<213> ORGANISM: artificial
<220> FEATURE:
<223> OTHER INFORMATION: derivative of SHP-1 having a single leucine
      deletion

<400> SEQUENCE: 7

Ser Asp Leu Gly Ala Val Ile Ser Leu Leu Trp Gly Arg Gln Leu Phe
1               5                   10                  15

Ala

<210> SEQ ID NO 8
<211> LENGTH: 15
<212> TYPE: PRT
<213> ORGANISM: artificial
<220> FEATURE:
<223> OTHER INFORMATION: derivative of SHP-1 having a deletion of
      C-terminal leucine in triplicate

<400> SEQUENCE: 8

Ser Asp Leu Gly Ala Val Ile Ser Trp Gly Arg Gln Leu Phe Ala
1               5                   10                  15

<210> SEQ ID NO 9
<211> LENGTH: 15
<212> TYPE: PRT
<213> ORGANISM: artificial
<220> FEATURE:
<223> OTHER INFORMATION: derivative of SHP-1 having a deletion of the
      N-terminal leucine-glycine-alanine residues

<400> SEQUENCE: 9
```

Ser Asp Val Ile Ser Leu Leu Leu Trp Gly Arg Gln Leu Phe Ala
1               5                   10                  15

<210> SEQ ID NO 10
<211> LENGTH: 18
<212> TYPE: PRT
<213> ORGANISM: artificial
<220> FEATURE:
<223> OTHER INFORMATION: non-specific, hydrophilic peptide predicted
      from the N-terminus of the alternatively edited protein-1 from
      mitochondria of T. b. brucei

<400> SEQUENCE: 10

Glu Arg Thr Glu Glu Ser Trp Gly Arg Arg Phe Trp Arg Arg Gly Glu
1               5                   10                  15

Ala Cys

<210> SEQ ID NO 11
<211> LENGTH: 20
<212> TYPE: PRT
<213> ORGANISM: artificial
<220> FEATURE:
<223> OTHER INFORMATION: amino acid sequence of small hydrophobic
      peptide -3 (SHP-3)

<400> SEQUENCE: 11

Phe His Gln Ile Trp Ala Ala Leu Leu Tyr Phe Tyr Gly Ile Ile Leu
1               5                   10                  15

Asn Ser Ile Tyr
            20

<210> SEQ ID NO 12
<211> LENGTH: 20
<212> TYPE: PRT
<213> ORGANISM: artificial
<220> FEATURE:
<223> OTHER INFORMATION: derivative of SHP-3 having a leucine to
      arginine substitution at position -5

<400> SEQUENCE: 12

Phe His Gln Ile Trp Ala Ala Leu Leu Tyr Phe Tyr Gly Ile Ile Arg
1               5                   10                  15

Asn Ser Ile Tyr
            20

<210> SEQ ID NO 13
<211> LENGTH: 20
<212> TYPE: PRT
<213> ORGANISM: artificial
<220> FEATURE:
<223> OTHER INFORMATION: derivative of SHP-3 having a leucine to
      glutamic acid substitution at position -5

<400> SEQUENCE: 13

Phe His Gln Ile Trp Ala Ala Leu Leu Tyr Phe Tyr Gly Ile Ile Glu
1               5                   10                  15

Asn Ser Ile Tyr
            20

<210> SEQ ID NO 14
<211> LENGTH: 18
<212> TYPE: PRT
<213> ORGANISM: artificial
<220> FEATURE:
<223> OTHER INFORMATION: derivative of SHP-1 having an aspartic acid to
      arginine substitution at position 2 and an arginine to aspartic -continued acid substitution at position -5

<400> SEQUENCE: 14

Ser Arg Leu Gly Ala Val Ile Ser Leu Leu Trp Gly Asp Gln Leu
1               5                   10                  15

Phe Ala

<210> SEQ ID NO 15
<211> LENGTH: 18
<212> TYPE: PRT
<213> ORGANISM: artificial
<220> FEATURE:
<223> OTHER INFORMATION: derivative of SHP-1 having a tryptophan
      substitution at position 1

<400> SEQUENCE: 15

Trp Asp Leu Gly Ala Val Ile Ser Leu Leu Gly Gly Arg Gln Leu
1               5                   10                  15

Phe Ala

<210> SEQ ID NO 16
<211> LENGTH: 18
<212> TYPE: PRT
<213> ORGANISM: artificial
<220> FEATURE:
<223> OTHER INFORMATION: derivative of SHP-1 having a tryptophan
      substitution at position 8

<400> SEQUENCE: 16

Ser Asp Leu Gly Ala Val Ile Trp Leu Leu Gly Gly Arg Gln Leu
1               5                   10                  15

Phe Ala

<210> SEQ ID NO 17
<211> LENGTH: 18
<212> TYPE: PRT
<213> ORGANISM: artificial
<220> FEATURE:
<223> OTHER INFORMATION: derivative of SHP-1 having a tryptophan
      substitution at position 18

<400> SEQUENCE: 17

Ser Asp Leu Gly Ala Val Ile Ser Leu Leu Gly Gly Arg Gln Leu
1               5                   10                  15

Phe Trp

<210> SEQ ID NO 18
<211> LENGTH: 20
<212> TYPE: PRT
<213> ORGANISM: artificial
<220> FEATURE:
<223> OTHER INFORMATION: derivative of SHP-3 having a tryptophan
      substitution at position 1

<400> SEQUENCE: 18

Trp His Gln Ile Gly Ala Ala Leu Leu Tyr Phe Tyr Gly Ile Ile Leu
1               5                   10                  15

Asn Ser Ile Tyr
            20

<210> SEQ ID NO 19
<211> LENGTH: 20
<212> TYPE: PRT
<213> ORGANISM: artificial
<220> FEATURE:

-continued

```
<223> OTHER INFORMATION: derivative of SHP-3 having a tryptophan
      substitution at position 13

<400> SEQUENCE: 19

Phe His Gln Ile Gly Ala Ala Leu Leu Tyr Phe Tyr Trp Ile Ile Leu
1               5                   10                  15

Asn Ser Ile Tyr
            20

<210> SEQ ID NO 20
<211> LENGTH: 20
<212> TYPE: PRT
<213> ORGANISM: artificial
<220> FEATURE:
<223> OTHER INFORMATION: derivative of SHP-3 having a tryptophan
      substitution at position 20

<400> SEQUENCE: 20

Phe His Gln Ile Gly Ala Ala Leu Leu Tyr Phe Tyr Gly Ile Ile Leu
1               5                   10                  15

Asn Ser Ile Trp
            20
```

ANTI-TRYPANOSOMAL PEPTIDES AND USES THEREOF

CONTINUING APPLICATION DATA

This application is a continuation-in-part of International Application No. PCT/US2010/032545, filed Apr. 27, 2010, which claims the benefit of U.S. Provisional Application Ser. Nos. 61/172,908, filed Apr. 27, 2009, and 61/317,895, filed Mar. 26, 2010, all of which are incorporated herein by reference in their entireties.

GOVERNMENT FUNDING

The present invention was made with government support under Grant Nos. AI039033 and 1F32AI080114-01A1, awarded by the National Institutes of Health. The Government has certain rights in this invention.

BACKGROUND

*Trypanosoma brucei* is the causative agent of both a veterinary wasting disease and human African trypanosomiasis, or sleeping sickness. Human African trypanosomiasis occurs in 36 countries in sub-Saharan Africa, threatening an estimated 60 million people with debilitating disease. Currently, approximately 500,000 people are infected with African trypanosomes. No vaccines are available for prevention of infection by *T. brucei*. Without chemotherapeutic treatment, *T. brucei* kills infected humans. Treatment of infected individuals is limited and there is an increase in the number of relapses from established drug treatment. Drugs currently in use are quite toxic and cause serious side effects and in some cases death. And, the development of drug resistance is of concern. Few drug candidates are currently under clinical trials, and one of the more promising compounds, DB75, has already shown a marked tendency to induce drug resistance (Lanteri et al., 2006, *Mol Pharmacol;* 70(5):1585-1592). Consequently, there is a strong need for new and safer drugs for the treatment of trypanosomiasis and new drugs must be developed in order to prepare for possible emergence of drug resistance in the parasites.

SUMMARY OF THE INVENTION

The present invention includes methods of killing a bloodstream form (BSF) of a kinetoplastid protozoan of the genus *Trypanosoma*, the method including contacting the protozoan with a hydrophobic signal sequence peptide, wherein the hydrophobic signal sequence peptide consists of about 12 to about 25 amino acid residues, and wherein the hydrophobic signal sequence peptide contains a positively charged amino acid at position minus five relative to the C-terminus of the hydrophobic signal sequence peptide.

The present invention includes methods of treating or preventing a trypanosomal infection in a subject, the method including administering to the subject an effective amount of a hydrophobic signal sequence peptide, wherein the hydrophobic signal sequence peptide consists of about 12 to about 25 amino acid residues, and wherein the hydrophobic signal sequence peptide contains a positively charged amino acid at position minus five relative to the C-terminus of the hydrophobic signal sequence peptide.

In some aspects of the methods of the present invention, the hydrophobic signal sequence peptide has the sequence of an uncleaved signal sequence peptide of haptoglobin-related protein or paraoxonase 1.

In some aspects of the methods of the present invention, the hydrophobic signal sequence peptide is soluble in ethanol or dimethyl sulfoxide (DMSO).

In some aspects of the methods of the present invention, the hydrophobic signal sequence peptide includes at least nine consecutive amino acid residues of MSDLGAVISLLL-WGRQLFA (SEQ ID NO:1), MAKLIALTLLGMGLAL-FRNHQS (SEQ ID NO:3), a derivative of SEQ ID NO:1, or a derivative of SEQ ID NO:3, wherein a derivative of SEQ ID NO:1 or SEQ ID NO:3 has up to four hydrophobic amino acid residues of SEQ ID NO:1 or SEQ ID NO:3 exchanged for another hydrophobic amino acid, and/or up to four positively charged amino acid residues of SEQ ID NO:1 or SEQ ID NO:3 exchanged for another positively charged amino acid.

In some aspects of the methods of the present invention, the hydrophobic signal sequence peptide is selected from the group consisting of MSDLGAVISLLLWGRQLFA (SEQ ID NO:1), SDLGAVISLLLWGRQLFA (SEQ ID NO:2), MAK-LIATLLGMGLALFRNHQS (SEQ ID NO:3), AKLI-ATLLGMGLALFRNHQS (SEQ ID NO:4), or SDLGAVIS-LLWGRQLFA (SEQ ID NO:7), WDLGAVISLLLGGRQLFA (SEQ ID NO:15), SDLGAVI-WLLLGGRQLFA (SEQ ID NO:16) and SDLGAVISLLLG-GRQLFW (SEQ ID NO:17).

In some aspects of the methods of the present invention, the trypanosome is selected from the group consisting of *Trypanosoma brucei brucei, T. b. gambiense*, and *T. b. rhodesiense, T. congolense*, and *T. vivax*.

In some aspects of the methods of the present invention, the hydrophobic signal sequence peptide is administered as a composition further including liposome, emulsion, or micelle.

In some aspects of the methods of the present invention, the hydrophobic signal sequence peptide is administered as a composition further including an RNA aptamer that binds to a structurally conserved region of a trypanosome variant surface glycoprotein (VSG).

The present invention includes compositions including a hydrophobic signal sequence peptide and a pharmaceutical carrier suitable for parenteral or enteral administration to a mammal, wherein the hydrophobic signal sequence peptide consists of about 12 to about 25 amino acid residues, and wherein the hydrophobic signal sequence peptide contains a positively charged amino acid at position minus five relative to the C-terminus of the hydrophobic signal sequence peptide.

The present invention includes methods of killing a bloodstream form of a kinetoplastid protozoan of the genus *Trypanosoma*, the method including contacting the protozoan with a composition of claim 11.

The present invention includes methods of treating or preventing a trypanosomal infection in a subject, the method including administering to the subject an effective amount of a composition of claim 11.

In some aspects of the compositions of the present invention, the composition is pyrogen-free.

In some aspects of the compositions of the present invention, the hydrophobic signal sequence peptide has the sequence of an uncleaved signal sequence peptide of haptoglobin-related protein or paraoxonase 1.

In some aspects of the compositions of the present invention, the hydrophobic signal sequence peptide is soluble in ethanol or dimethyl sulfoxide (DMSO).

In some aspects of the compositions of the present invention, the hydrophobic signal sequence peptide includes at least nine consecutive amino acid residues of MSDLGAVIS-LLLWGRQLFA (SEQ ID NO:1), MAKLIALTLLGMGLA- LFRNIHQS (SEQ ID NO:3), a derivative of SEQ ID NO:1, or a derivative of SEQ ID NO:3, wherein a derivative of SEQ ID NO:1 or SEQ ID NO:3 has up to four hydrophobic amino acid residues of SEQ ID NO:1 or SEQ ID NO:3 exchanged for another hydrophobic amino acid, and/or up to four positively charged amino acid residues of SEQ ID NO:1 or SEQ ID NO:3 exchanged for another positively charged amino acid.

In some aspects of the compositions of the present invention, the hydrophobic signal sequence peptide is selected from the group consisting of MSDLGAVISLLLWGRQLFA (SEQ ID NO:1), SDLGAVISLLLWGRQLFA (SEQ ID NO:2), MAKLIATLLGMGLALFRNHQS (SEQ ID NO:3), AKLIATLLGMGLALFRNHQS (SEQ ID NO:4), or SDLGAVISLLWGRQLFA (SEQ ID NO:7), WDLGAVISLLLGGRQLFA (SEQ ID NO:15), SDLGAVIWLLLGGRQLFA (SEQ ID NO:16) and SDLGAVISLLLGGRQLFW (SEQ ID NO:17).

In some aspects of the compositions of the present invention, the composition includes a liposome, emulsion, or micelle including the hydrophobic signal sequence peptide.

In some aspects of the compositions of the present invention, further including an RNA aptamer that binds to a structurally conserved region of a trypanosome variant surface glycoprotein (VSG).

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE FIGURES

In FIG. 1A, wild type 427 $T. b. brucei$ cells were incubated with increasing concentrations of Hpr-SP (8-80 µM) added from a stock solution in DMSO. Positive controls were trypanosome lytic factor (TLF). Addition of equivolume DMSO or equimolar concentrations of a non-specific hydrophilic 19 amino acid peptide (NS 19mer; SEQ ID NO:10) gave no trypanolysis. The inset in FIG. 1A shows cells treated with Hpr-SP. FIG. 1B is a cartoon of Hpr and the derived peptide Hpr-SP (SEQ ID NO:1). Hydrophobic residues are in bold.

In FIG. 7A, SHP-1 was assayed for killing activity against bloodstream form (BSF) $T. b. brucei$ (diamond), $T. b. rhodesiense$ (square), $T. b. gambiense$ (triangle) and procyclic form (PCF) $T. b. brucei$ (circle). Equivolume additions of solvent DMSO (black circle) showed no toxic effect. FIG. 7B is DIC micrographs of untreated, $T. b. brucei$ fixed with formaldehyde and unfixed $T. b. brucei$ incubated with 4 and 80 µM SHP-1 for two hours at 37° C. FIG. 7C presents binding of Texas-red labeled SHP-1 to bloodstream form (BSF), with and without peptide, and procyclic form (PCF), with and without peptide. $T. b. brucei$ monitored by flow cytometry.

In FIG. 8A, human cell lines, HEK (circles) and LNCaP (square), are not killed by SHP-1 as assayed by trypan blue exclusion. FIG. 8B demonstrates that SHP-1 (80 µM) does not induce morphological changes in HEK or LNCaP cells. The cytolytic peptide melittin (25 µM) was utilized as a positive control. FIG. 8C, flow cytometry indicates that Texas-red labeled SHP-1 does not bind HEK or LNCaP cells. FIG. 8D, potential hemolytic activity of SHP-1 was assayed against fresh human erythrocytes.

FIG. 9A presents peptide amino acid sequences, N to C-terminal. SBP-1 is SDLGAVISLLLWGRQLFA (SEQ ID NO:2); SHP-2 is AKLIALTLLGMGLALFRNHQS (SEQ ID NO:4); SHP-1-ΔL is SDLGAVISLLWGRQLFA (SEQ ID NO:7); SHP-1-ΔLLL is SDLGAVISWGRQLFA (SEQ ID NO:8); SBP-1-ΔLGA is SDVISLLLWGRQLFA (SEQ ID NO:9); and NSP is ERTEESWGRRFWRRGEAC (SEQ ID NO:10). FIG. 9B demonstrates the killing of bloodstream form (BSF) $T. b. brucei$ by SHP-1 (squares) and its variants, SHP-2 (diamonds), SHP-1-ΔL (white circles), SHP-1ΔLLL (black triangles), SHP-1-ΔLGA (gray triangles) and a non-specific hydrophilic peptide (NSP, gray circles). FIG. 9C is representative traces of liposome permeabilization by 200 nM SHP-1, 200 nM SHP-2 and the deletion variants, 500 nM SHP-1-ΔL, 500 nM SHP-1-ΔLLL and 500 nM SHP-1Δ-LGA.

FIG. 10A demonstrates that killing of BSF $T. b. brucei$ does not require cellular uptake, indicated by robust SHP-1-mediated killing at 3° C., a temperature non-permissive for endocytosis. Alexa 594-labeled transferrin (Tf) binds at the flagellar pocket, but is not taken up at 3° C. (inset). In FIG. 10B, fluorescence microscopy with Texas-red labeled SHP-1 reveals diffuse labeling of the cell surface rather than accumulation within an intracellular vesicle as displayed by Alexa 594-labeled transferrin (Tf). Cell nuclei and kinetoplast are labeled with DAPI.

FIG. 11A demonstrates that lateral van der Waals interactions dictate sensitivity to Hpr-SP, as indicated by the ability of 200 nM SHP-1 to readily elicit calcein leakage from unilamellar liposomes composed of egg phosphatidylcholine (PC), a highly fluid, heterogeneous mixture of naturally derived lipids with $T_m$<0° C., whereas liposomes composed of homogeneous lipid species with symmetric acyl chains, 15:0 ($T_m$=34° C.) or 16:0 ($T_m$=41° C.) are resistant. No permeabilization is seen against liposomes composed of symmetric 17:0 or 18:0 PC either. In FIG. 11B, the addition of 1,2-dimyristoyl-sn-glycero-3-phosphocholine (DMPC) (indicated by percentage) to refractory compositions 1,2-distearoyl-sn-glycero-3-phosphocholine (DSPC) renders liposomes susceptible to permeabilization by SHP-1. FIG. 11C demonstrates that liposomes composed of 1-stearoyl-2-oleoyl-sn-glycero-3-phosphocholine (SOPC) or 1-palmitoyl-2-oleoyl-sn-glycero-3-phosphocholine (POPC), asymmetrical PC lacking myristate, but exhibiting fluid lipid packing due to unsaturations (16:0, 18:1, $T_m=-2°$ C. and 18:0, 18:1, $T_m=6°$ C.) are susceptible to permeabilization by SHP-1. FIG. 11D demonstrates that thermal fluidization of symmetrical 15:0 and 16:0 PC lipid bilayers renders liposomes susceptible to permeabilization by SHP-1. Assays were carried out at approximately 60° C.

In FIG. 12A, the rigidity of BSF *T. brucei* plasma membranes is increased by the addition of SHP-1 as revealed by the anisotropic changes in the membrane probe 1-(4-trimethylammoniumphenyl)-6-phenyl-1,3,5-hexatriene p-toluenesulfonate (TMA-DPH) (SHP-1—closed circle, DMSO only—open circles). Consistent with the lack of binding to more rigid lipid bilayers and the higher anisotropic values acquired for procyclic form (PCF) *T. brucei*, SHP-1 has no effect on the anisotropy of PCF *T. brucei* cell plasma membranes (SHP-1—closed squares, DMSO only—open squares). FIG. 12B depicts the changes in motility of bloodstream form *T. brucei* treated with 8 M FIG. 12C presents images captured via DIC videomicroscopy illustrate the normal, hyperactive and constricted phenotype of cells treated with Hpr-SP. The normal motion of bloodstream form *T. brucei* displays a full rotation within 100 ms. Hyperactive cells appear to have accomplished 1.5-2 rotations within 50 ms. The constricted phenotype is commonly seen as a bent or boomerang shaped trypanosome that fails to complete a rotation.

In FIG. 13A the metacyclic developmental form (the developmental stage injected during a tsetse fly bite) of *T. b. brucei* (circles) and the veterinary pathogenic African trypanosomes, *T. vivax* (triangles) and *T. congolense* (squares), were assayed for susceptibility to SHP-1 in a two hour in vitro killing assay. In FIG. 13B the sequences of trypanolytic and non-trypanolytic SHP are shown from N- to C-terminus and aligned to the C-terminus in order to emphasize the identity of the amino acid at position −5 relative to the putative signal peptidase cleavage site. Positively charged amino acids are circled, negatively charged amino acids are boxed and non-polar amino acids are underlined. SHP-1 is SDLGAVISLLLWGRQLFA (SEQ ID NO:2); SHP-2 is AKLIALTLLGMGLALFRNHQS (SEQ ID NO:4); SHP-3 is FHQIWAALLYFYGIILNSIY (SEQ ID NO:11); SHP-3ΔR is FHQIWAALLYFYGERNSIY (SEQ ID NO:12); SHP-3ΔE is FHQIWAALLYFYGMENSIY (SEQ ID NO:13); and SHP-1swap is SRLGAVISLLL-WGDQLFA (SEQ ID NO:14). In FIG. 13C the SHP listed in FIG. 13B were tested against BSF *T. b. brucei* in a two hour killing assay. Peptide used are shown in FIG. 13B; SHP-1 (closed circles), SHP-3 (closed squares), SHP-3ΔR (closed triangles), SHP-3ΔE (open triangles), SHP-1swap (open circles).

FIG. 14C is a FRAP analysis of the mobile fraction of BSF *T. b. brucei* VSG in the presence (gray bars) or absence (black bars) of 8 μM SHP-1. In FIG. 14D live BSF *T. b. brucei* treated with 40 μM SHP-1, SHP-3 or SHP-3ΔR were scored via video microscopy for hyperactivation (white bars), constriction (gray bars) or normal motility (black bars).

In FIG. 17A small hydrophobic peptide-1 tryptophan variants SHP-1Δ W1 (●), SHP-1ΔW8 (□) and SHP-1ΔW18 (▲) were tested for trypanocidal activity. In FIG. 17B the ability of the SHP-1 tryptophan variants 1 μM SHP-1ΔW1, 1 SHP-1ΔW8, 0.2 μM SHP-1 and 0.2 μM SHP-1ΔW18 to interact with lipid bilayers was determined by monitoring the release of entrapped calcein from unilamellar egg phosphatidylcholine liposomes. In FIG. 17C the ability of the SHP-3 tryptophan variants 1 μM SHP-3ΔW1, 1 μM SHP-3, 1 μM SHP-3ΔW13 and 4 μM SHP-3ΔW20 to interact with lipid bilayers was determined by monitoring the release of entrapped calcein from unilamellar egg phosphatidylcholine liposomes.

DETAILED DESCRIPTION OF ILLUSTRATIVE EMBODIMENTS OF THE INVENTION

Figure 1:
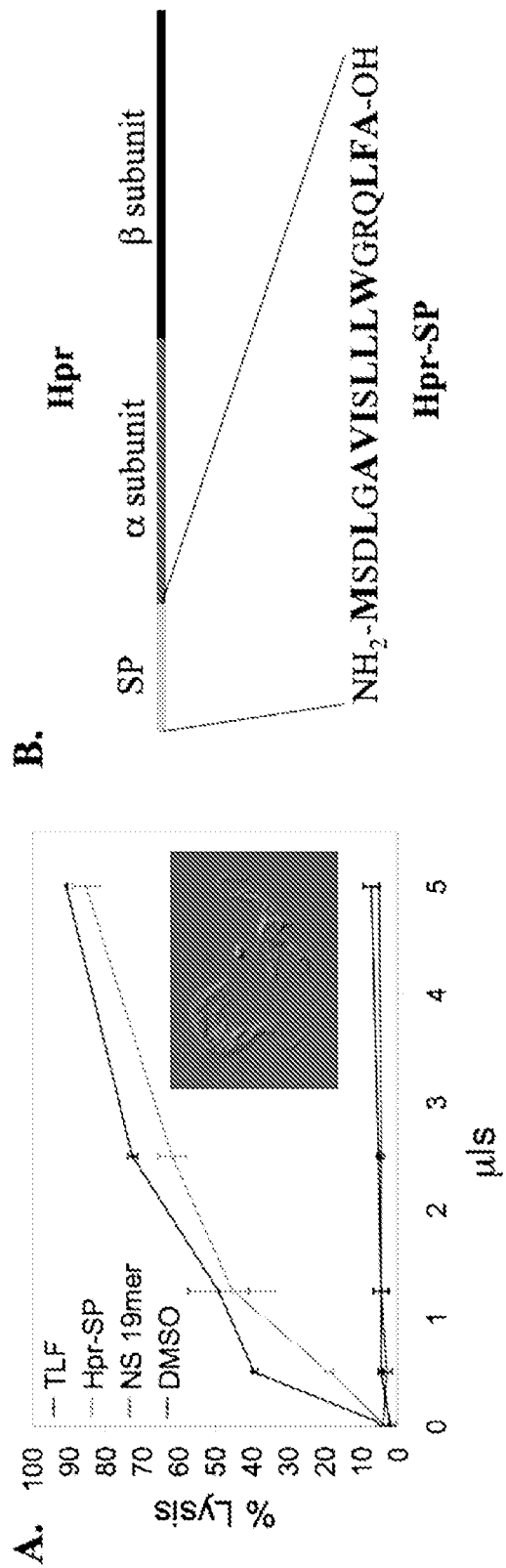
FIG. 1 shows the killing of $T. b. brucei$ by the Hpr-SP.

The present invention demonstrates, for the first time, the trypanocidal activity of hydrophobic signal sequence peptides and provides methods of killing, inhibiting the growth, and/or inhibiting the reproduction of kinetoplastid protozoan, including, but not limited to, kinetoplastid protozoan of the genus *Trypanosoma*, with hydrophobic signal sequence peptides and compositions including such hydrophobic signal sequence peptides. Protozoal pathogens have a worldwide impact and cause symptomatic as well as asymptomatic infections. Unfortunately, effective treatments for the different diseases are by and large not available. This is especially true for African trypanosomiasis, a parasitic disease caused by a specific class of protozoan organisms, trypanosomes. The eukaryotic parasite *Trypanosoma brucei* infects mammals and causes debilitating diseases in both humans and cattle. The subspecies *Trypanosoma brucei brucei* (*T. b. brucei*) causes the wasting disease in cattle nagana in cattle, while the two subspecies *Trypanosoma brucei rhodesiense* (*T. b. rhodesiense*) and *Trypanosoma brucei gambiense* (*T. b. gambiense*) cause sleeping sickness, also known as human African trypanosomiasis (HAT), in humans.

The methods and compositions of the present invention are applicable for a variety of protozoa, including, but not limited to, kinetoplastid protozoa. Kinetoplastids are a group of flagellate protozoa, including a number of parasites responsible for serious diseases in humans and other animals, including economically relevant livestock, as well as various forms found in soil and aquatic environments. They are included in the *Euglenozoa*, and are distinguished from other such forms mainly by the presence of a kinetoplast, a DNA-containing granule located within the single mitochondrion and associated with the flagellar bases. Kinetoplastids typically have complex life-cycles involving more than one host, and go through various morphological stages. The most distinctive of these is the trypomastigote stage, where the flagellum runs along the length of the cell and is connected to it by an undulating membrane. Kinetoplastid protozoa, include, for example, protozoa of the *Blastocrithidia, Crithidia, Endotrypanum, Herpetomonas, Leishmania, Leptomonas, Phytomonas, Trypanosoma*, and *Wallaceina* genera. Diseases caused by trypanosomes include African Sleeping Sickness and South American Chagas Disease, from species of *Trypanosoma*, and leishmaniasis, from species of *Leishmania*.

In some embodiments, the methods and compositions of the present invention are applicable for species of *Trypanosoma*, including, but are not limited to, *T. avium*, which causes trypanosomiasis in birds, *T. boissoni, T. brucei*, which causes sleeping sickness in humans and nagana in cattle, *T. carassii*, in freshwater teleosts, *T. cruzi*, which causes Chagas disease in humans, *T. gambiense, T. rhodesiense, T. congolense*, which causes nagana in cattle, horses, and camels, *T. equinum, T. equiperdum*, which causes dourine or covering sickness in horses, *T. evansi*, which causes one form of the disease surra in certain animals, *T. lewisi*, in rats, *T. melophagium, T. percae* in fish, *T. rangeli, T. rotatorium* in amphibian, *T. simiae, T. suis, T. theileri, T. triglae*, and *T. vivax*.

In some embodiments, the methods and compositions of the present invention are applicable for the protozoan *T. brucei*, including, but not limited to, *Trypanosoma brucei brucei, T. cruzi, T. brucei, T. b. gambiense, T. b. rhodesiense, T. congolense*, and *T. vivax*. In some embodiments, the methods and compositions of the present invention are applicable for the protozoan *Trypanosoma brucei brucei, T. b. gambiense*, and *T. b. rhodesiense, T. congolense*, and *T. vivax*. In some embodiments, the methods and compositions of the present invention are applicable for various protozoan *Trypanosoma brucei*, excluding *T. cruzi*.

The present invention has identified peptides that demonstrate the ability of killing the bloodstream form (BSF) of kinetoplastid protozoans of the genus *Trypanosoma*. More specifically, these trypanocidal peptides are based upon the hydrophobic N-terminal signal sequences of various mammalian plasma proteins. Additionally these peptides exhibit reduced or no toxicity towards mammalian cell lines and induce limited or no hemolysis.

Proteins have intrinsic signals that govern their transport and localization within the cell. Almost all proteins that are transported to the endoplasmic reticulum and destined either to be secreted or to be membrane components have a short signal sequence that directs the transport of a protein through the cell membrane. This signal peptide is an amino acid sequence present on the protein. It is usually at the N terminus. It is usually is cleaved off and absent in the mature protein, though in some proteins, the signal peptide uncleaved and is retained in the mature protein. Signal peptides are highly hydrophobic but with some positively charged residues.

A trypanocidal peptides of the present invention may also be referred to herein as an anti-trypanosomal peptides, a signal peptide, SP, a signal sequence peptide, a hydrophobic peptide, a hydrophobic signal sequence peptide, a N-terminal signal sequence, or a hydrophobic N-terminal signal sequence.

A trypanocidal peptide of the present invention may be a known hydrophobic N-terminal signal sequence, or a fragment or derivative thereof. A trypanocidal peptide of the present invention may be a hydrophobic N-terminal signal sequence, with or without the N-terminal methionine residue, or a derivative or fragment thereof. Derivatives include, but are not limited to, the exchange of one, two, three, four, or more hydrophobic amino acid residues for another hydrophobic amino acid. Such hydrophobic amino acids include valine ("Val" or "V"), isoleucine ("He" or "I"), leucine ("Leu" or "L"), methionine ("Met" or "M"), phenyalanine ("Phe" or "F"), tryptophan ("Trp" or "W"), cysteine ("Cys" or "C"), alanine ("Ala" or "A"), tyrosine ("Tyr" or "Y"), histidine ("His" or "H"), threonine, ("Thr" or "T"), serine ("Ser" or "S"), proline ("Pro" or "P"), glycine ("Gly" or "G"), arginine ("Arg" or "R"), and lysine ("Lys" or "K"). In some embodiments, derivatives include, but are not limited to, the exchange of one, two, three, four, or more very hydrophobic amino acid residues for another very hydrophobic amino acid. Such very hydrophobic amino acids include valine ("Val" or "V"), isoleucine ("Ile" or "I"), leucine ("Leu" or "L"), methionine ("Met" or "M"), phenyalanine ("Phe" or "F"), tryptophan ("Trp" or "W"), and cysteine ("Cys" or "C"). Derivatives include, but are not limited to, the exchange of one, two, three, four, or more positively charged amino acid residues for another positively charged amino acid. Derivatives include, but are not limited to, the deletion of one, two, three, or more hydrophobic amino acids from the known signal sequence. Derivatives also include, but are not limited to, the deletion of one, two, three, or more very hydrophobic amino acids from the known signal sequence. Derivatives may also include any combination of the above substitutions and/or deletions. Fragments may include, but are no limited to, peptides having at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 consecutive amino acids of the hydrophobic N-terminal signal peptide. Such sequences may be consecutive sequences.

A trypanocidal peptide of the present invention may be any of a variety of lengths. A trypanocidal peptide of the present invention may be, for example, about 3 to about 60 amino acids in length, about 9 to about 25 amino acids in length, about 10 to about 25 amino acids in length, about 12 to about 25 amino acids in length, about 14 to about 25 amino acids in length, about 17 to about 25 amino acids in length, about 19 to about 25 amino acids in length, about 19 to about 22 amino acids in length, or about 17 to about 23 amino acids in length. A trypanocidal peptide of the present invention may be, for example, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 amino acids in length and/or no more that about 10, no more than about 11, no more than about 12, no more than about 13, no more than about 14, no more than about 15, no more than about 16, no more than about 17, no more than about 18, no more than about 19, no more than about 20, no more than about 21, no more than about 22, no more than about 23, no more than about 24, no more than about 25, no more than about 26, no more than about 27, no more than about 28, no more than about 29, or no more than about 30 amino acids in length. For example, a trypanocidal peptide of the present invention may be, for example, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids in length. For example, a trypanocidal peptide of the present invention may be, for example, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids in length.

A trypanocidal peptide of the present invention may be a hydrophobic peptide. For example, in a hydrophobic peptide at least about 50%, at least about 55%, at least about 60%, at least about 65%, at least about 70%, at least about 75%, at least about 80%, at least about 85%, at least about 90%, or at least about 95% of the amino acid residues are hydrophobic amino acid residues. For example, in a hydrophobic peptide all but 10 or fewer, all but 9 or fewer, all but 8 or fewer, all but 7 or fewer, all but 6 or fewer, all but 5 of fewer, all but 4 or fewer, all but 3 or fewer, all but 2 or fewer, or all but 1 of the amino acid residues are hydrophobic amino acid residues.

A trypanocidal peptide of the present invention may have a positively charged amino acid residue at a position minus 5 from the C-terminus of the peptide. Such positively charged amino acids include arginine ("Arg" or "R"), lysine ("Lys" or "K"), and histidine ("His" or "H").

A trypanocidal peptide of the present invention may have an alpha helical conformation in a nonpolar environment or solution.

Trypanocidal peptides of the present invention may be identified by any of a variety of means, including, but not limited to, any of the assays described herein, including, but not limited to, a trypanosome lysis assay. Trypanocidal peptides of the present invention may target the cell membrane of protozoans, including, but not limited to kinetoplastid protozoans of the genus *Trypanosoma*, and may that increase the rigidity of lipid bilayers of the cell membrane. Trypanocidal peptides of the present invention may selectively partition into the plasma membrane of BSF trypanosomes resulting in an increase in the rigidity of the bilayer, changes in cell motility and/or subsequent cell death.

A trypanocidal peptide of the present invention may be a hydrophobic N-terminal signal sequence of a protein that is associated with high density lipoproteins (HDL). A trypanocidal peptide of the present invention may be a hydrophobic N-terminal signal sequence of an apolipoprotein, including, but not limited to a human apolipoprotein.

In some embodiments, a trypanocidal peptide of the present invention is an uncleaved, hydrophobic N-terminal signal peptide, that is, a signal peptide that is retained on the mature protein, and derivatives and fragments thereof. Examples of proteins with uncleaved signal peptides are haptoglobin-related protein (Hpr), serum paraoxonase/arylesterase (PON1), and apolipoprotein M (Apo M), including, but not limited to, human haptoglobin-related protein, human serum paraoxonase/arylesterase (PON1), and human apolipoprotein M (Apo M).

In some embodiments, a trypanocidal peptide of the present invention includes the hydrophobic N-terminal signal peptide of haptoglobin-related protein (also referred to herein as "Hpr" or "HPR"), including, but not limited to, human haptoglobin-related protein (UniProtKB/Swiss-Prot Accession No: P00739), fragments and derivatives thereof. Hpr is an integral part of two distinct high molecular weight complexes (trypanosome lytic factor 1 (TLF1) and trypanosome lytic factor 2 (TLF2)) that are lytic for the African parasite *Trypanosoma brucei brucei*. See, for example, Smith et al., 1995, *Science;* 268(5208):284-6; Drain et al., 2001, *J Biol Chem;* 276(32):30254-60; and Muranjan et al., 1998, *J Biol Chem;* 273(7):3884-7. Human haptoglobin-related protein demonstrates an uncleaved signal peptide. For example, trypanocidal peptides of the present invention include peptides having the N-terminal amino acid residues 1-19, or 2-19 of the human haptoglobulin-related protein (MSDLGAVIS-LLLWGRQLFA (SEQ ID NO:1) and SDLGAVISLLL-WGRQLFA (SEQ ID NO:2), respectively), fragments, and derivatives thereof. Derivatives include any of the derivatives described herein, including, but are not limited to, the exchange of one, two, three, four, or more hydrophobic amino acid residues for another hydrophobic amino acid. Derivatives may include, but are not limited to, the exchange of one, two, three, four, or more very hydrophobic amino acid residues for another very hydrophobic amino acid. Derivatives include, but are not limited to, the exchange of one, two, three, four, or more positively charged amino acid residues for another positively charged amino acid, including, but not limited to, a substitution at the positively charged amino acid at position minus 5 from the C terminus. Derivatives may include, but are not limited to, the deletion of one, two, three, or more hydrophobic amino acids from the known signal sequence. Derivatives may also include, but are not limited to, the deletion of one, two, three, or more very hydrophobic amino acids from the known signal sequence. Derivatives also include any combination of the above substitutions and/or deletions. Fragments may include, but are no limited to, peptides having at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 consecutive amino acids of the hydrophobic N-terminal signal peptide of haptoglobin-related protein or derivative thereof, including, but not limited to, human haptoglobin-related protein (UniProtKB/Swiss-Prot Accession No: P00739)

In some embodiments, a trypanocidal peptide of the present invention includes the hydrophobic N-terminal signal peptide of serum paraoxonase/arylesterase (PON1), including, but not limited to, human serum paraoxonase/arylesterase (UniProtKB/Swiss-Prot Accession No. P27169), fragments and derivatives thereof. Serum paraoxonase/arylesterase, like haptoglobin-related protein, demonstrates an uncleaved signal peptide. For example, trypanocidal peptides of the present invention include peptides having the N-terminal amino acid residues 1-22, or 2-22 of human paraoxonase-1 protein (MAKLIALTLLGMGLALFRNHQS (SEQ ID NO:3) and AKLIALTLLGMGLALFRNHQS (SEQ ID NO:4), respectively), fragments, and derivatives thereof. Derivatives include any of the derivatives described herein, including, but are not limited to, the exchange of one, two, three, four, or more hydrophobic amino acid residues for another hydrophobic amino acid. Derivatives may include, but are not limited to, the exchange of one, two, three, four, or more very hydrophobic amino acid residues for another very hydrophobic amino acid. Derivatives include, but are not limited to, the exchange of one, two, three, four, or more positively charged amino acid residues for another positively charged amino acid, including, but not limited to, a substitution at the positively charged amino acid at position minus 5 from the C terminus. Derivatives may include, but are not limited to, the deletion of one, two, three, or more hydrophobic amino acids from the known signal sequence. Derivatives may also include, but are not limited to, the deletion of one, two, three, or more very hydrophobic amino acids from the known signal sequence. Derivatives also include any combination of the above substitutions and/or deletions. Fragments may include, but are no limited to, peptides having at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 consecutive amino acids of the hydrophobic N-terminal signal peptide of paraoxonase or derivative thereof, including, but not limited to, human serum paraoxonase/arylesterase (UniProtKB/Swiss-Prot Accession No. P27169.

In some embodiments, a trypanocidal peptide of the present invention includes the hydrophobic N-terminal signal peptide of apolipoprotein M (Apo M), including, but not limited to, human apolipoprotein M (UniProtKB/Swiss-ProtO95445), fragments and derivatives thereof. Apolipoprotein M, like haptoglobin-related protein, and paraoxonase demonstrates an uncleaved signal peptide. For example, trypanocidal peptides of the present invention include peptides having the N-terminal amino acid residues 1-22, or 2-22 of human apolipoprotein. M (MFHQIWAALLYFYGIILNSIYQ (SEQ ID NO:5) and FHQIWAALLYFYGIILLNSIYQ (SEQ ID NO:6), respectively), fragments, and derivatives thereof. Derivatives include, but are not limited to, any of the derivatives described herein. Derivatives include the exchange of one, two, three, four, or more hydrophobic amino acid residues for another hydrophobic amino acid. Derivatives include the exchange of one, two, three, four, or more positively charged amino acid residues for another positively charged amino acid, including, but not limited to, a substitution at the positively charged amino acid at position minus 5 from the C terminus. Derivatives may include the deletion of one, two, three, or more hydrophobic amino acids from the known signal sequence. Derivatives may also include the deletion of one, two, three, or more very hydrophobic amino acids from the known signal sequence. Derivatives also include any combination of the above substitutions and/or deletions. Fragments may include, but are no limited to, peptides having at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 consecutive amino acids of the hydrophobic N-terminal signal peptide of apolipoprotein M (Apo M) or derivative thereof, including, but not limited to, human apolipoprotein M UniProtKB/Swiss-Prot095445.

A trypanocidal peptide of the present invention includes any of the trypanocidal peptides described herein, including, but not limited to, MSDLGAVISLLLWGRQLFA (SEQ ID NO:1), SDLGAVISLLLWGRQLFA (SEQ ID NO:2), MAKLIATLLGMGLALFRNHQS (SEQ ID NO:3), AKLIATLLGMGLALFRNHQS (SEQ ID NO:4), or SDLGAVISLLWGRQLFA (SEQ ID NO:7), WDLGAVISLLLGGRQLFA (SEQ ID NO:15), SDLGAVIWLLLGGRQLFA (SEQ ID NO:16) or SDLGAVISLLLGGRQLFW (SEQ ID NO:17) and derivatives and fragments thereof. Derivatives include, but are not limited to, any of the derivatives described herein. Derivatives include, but are not limited to, the exchange of one, two, three, four, or more hydrophobic amino acid residues for another hydrophobic amino acid. Derivatives include, but are not limited to, the exchange of one, two, three, four, or more positively charged amino acid residues for another positively charged amino acid, including, but not limited to, a substitution at the positively charged amino acid at position minus 5 from the C terminus. Derivatives may also include, but are not limited to, the deletion of one, two, three, or more very hydrophobic amino acids from the known signal sequence. Derivatives also include any combination of the above substitutions and/or deletions. Fragments may include, but are no limited to, peptides having at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 consecutive amino acids of SEQ ID NO:1), SEQ ID NO:2, SEQ ID NO:3, SEQ ID NO:4, or SEQ ID NO:7, SEQ ID NO:15, SEQ ID NO:16 or SEQ ID NO:17.

The present invention provides for the use of trypanocidal peptides as, anti-protozoan agents and provides methods of killing, inhibiting the growth, inhibiting the reproduction, and/or rigidifying the plasma membrane of a protozoan by contacting the protozoan with one or more trypanocidal peptides. As used herein, the term "inhibit" means prevent, decrease, or reverse. Such contact may be in vitro, ex vivo, and/or in vivo. As used herein in vitro is in cell culture, ex vivo is a cell that has been removed from the body of a subject, and in vivo is within the body of a subject. As used herein, the term "subject" or "individual" represents an organism, including, for example, a mammal. A mammal includes, but is not limited to, a human, a non-human primate, livestock (such as, but not limited to, a cow, a horse, a goat, and a pig), a rodent, such as, but not limited to, a rat or a mouse, or a domestic pet, such as, but not limited to, a dog or a cat.

The present invention provides methods of killing, inhibiting the growth, inhibiting the reproduction, and/or rigidifying the plasma membrane of a protozoan in a subject by administering to the subject an effective amount of one or more trypanocidal peptides. A trypanocidal peptide of the present invention may be administered in an amount effective to inhibit replication and/or growth of the protozoan. A trypanocidal peptide of the present invention may be administered in an amount effective to kill a protozoan in an infected individual Inhibition of the growth and reproduction of a protozoan and killing of an a protozoan may be determined by any of various known methods, including, but not limited to, the methods described in the examples herein.

The present invention provides for the use of trypanocidal peptides as anti-protozoan agents and provides methods of killing, inhibiting the growth, inhibiting the reproduction, and/or rigidifying the plasma membrane of a protozoan by contacting the protozoan with one or more trypanocidal peptides.

The present invention provides for the use of trypanocidal peptides as plasma membrane rigidifying agents and provides methods for rigidifying the plasma membrane of a protozoan by contacting the protozoan with one or more trypanocidal peptides. In some aspects, the trypanosome is a blood stage form (BSF).

The present invention provides methods of treating or preventing a protozoan infection in a subject by administering to the subject an effective amount of one or more trypanocidal peptides. Such a trypanocidal peptide may be identified by the methods described herein. As used herein "treating" or "treatment" may include therapeutic and/or prophylactic treatments. Desirable effects of treatment may include preventing occurrence or recurrence of disease, alleviation of symptoms, diminishment of any direct or indirect pathological consequences of the disease, decreasing the rate of disease progression, amelioration or palliation of the disease state, and remission or improved prognosis. A trypanocidal peptide may be administered to a subject to reduce the severity of the symptoms associated with a protozoan infection. Peptides of the present invention may be taken as a prophylactic to prevent the development of a protozoan infection. A peptide of the present invention may be administered to a subject to prevent the infection of a subject with a protozoan. A peptide of the present invention may be administered to a subject prior to and/or after exposure to a protozoan.

A trypanocidal peptide may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

By a "therapeutically effective amount" of a trypanocidal peptide is meant a sufficient amount of the compound to treat the subject at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

Trypanocidal peptides of the present invention can be administered by any suitable means including, but not limited to, for example, parenteral (involving piercing the skin or mucous membrane), oral (through the digestive tract), transmucosal, rectal, nasal, topical (including, for example, transdermal, aerosol, buccal and sublingual), or vaginal. Parenteral administration may include, for example, subcutaneous, intramuscular, intravenous, intradermal, intraperitoneal, infrasternal, and intraarticular injections as well as various infusion techniques)

The present invention includes compositions including one or more trypanocidal peptides as described herein. Also included are compositions of one or more isolated trypanocidal peptides. As used herein, the term isolated means a preparation that is either removed from its natural environment or synthetically derived, for instance by recombinant techniques, or chemically or enzymatically synthesized. In a preferred form, an isolated trypanocidal peptides is purified and substantially free of other agents.

Compositions may be administered in any of the methods of the present invention and may be formulated in a variety of foams adapted to the chosen route of administration. The formulations may be conveniently presented in unit dosage form and may be prepared by methods well known in the art of pharmacy. A composition may include a pharmaceutically acceptable carrier. The term "pharmaceutically acceptable," as used herein, means that the compositions or components thereof so described are suitable for use in contact with human skin without undue toxicity, incompatibility, instability, allergic response, and the like. A composition may be a pharmaceutical composition.

The preparation of such compositions is well understood in the art. The formulations of this invention may include one or more accessory ingredients including, but not limited to, diluents, buffers, binders, disintegrants, surface active agents, thickeners, lubricants, preservatives, including, for example, antioxidants, and the like. Pharmaceutically acceptable includes salts, amides and esters that are well known in the art. Representative acid addition salts include, for example, hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like. Representative alkali or alkaline earth metal salts include, for example, aluminum, calcium, lithium, magnesium, potassium, sodium, or zinc salt, an ammonium salt such as a tertiary amine or quaternary ammonium salt, and an acid salt such as a succinate, tartarate, bitartarate, dihydrochloiide, salicylate, hemisuccinate, citrate, isocitrate, malate, maleate, mesylate, hydrochloride, hydrobromide, phosphate, acetate, carbamate, sulfate, nitrate, formate, lactate, gluconate, glucuronate, pyruvate, oxalacetate, fumarate, propionate, aspartate, glutamate, or benzoate salt, and the like. Pharmaceutically acceptable carriers includes, for example, non-toxic, inert solid, semi-solid or liquid filler, diluent, encapsulating material or formulation auxiliary of any type. Examples of materials that may serve as pharmaceutically acceptable carriers include, but are not limited to, sugars, such as, for example, lactose, glucose and sucrose, starches such as, for example, corn starch and potato starch, cellulose and its derivatives such as, for example, sodium carboxymethyl cellulose, ethyl cellulose and cellulose acetate, powdered tragacanth, malt, gelatin, talc, excipients such as, for example, cocoa butter and suppository waxes, oils such as, for example, peanut oil, cottonseed oil, safflower oil, sesame oil, olive oil, corn oil and soybean oil, glycols, such as, for example, propylene glycol, polyols such as, for example, glycerin, sorbitol, mannitol and polyethylene glycol, esters such as, for example, ethyl oleate and ethyl laurate, agar, buffering agents such as, for example, magnesium hydroxide and aluminum hydroxide, alginic acid, pyrogen-free water, isotonic saline, Ringer's solution, ethyl alcohol and phosphate buffer solutions, as well as other non-toxic compatible substances used in pharmaceutical formulations. Wetting agents, emulsifiers and lubricants such as, for example, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

For parenteral administration in an aqueous solution, the solution may be suitably buffered if necessary and the liquid diluent first rendered isotonic with sufficient saline or glucose. For enteral administration, the inhibitor may be administered in a tablet or capsule, which may be enteric coated, or in a formulation for controlled or sustained release. Many suitable formulations are known, including polymeric or microparticles or nanoparticles encapsulating drug to be released, ointments, gels, or solutions which can be used topically or locally to administer drug, and even patches, which provide controlled release over a prolonged period of time. These can also take the form of implants. Compositions for nasal administration may be formulated for aerosol or inhalation administration. Such compositions may include solutions in saline which may also contain, for example, benzyl alcohol or other suitable preservatives, absorption promoters to enhance bioavailability, and/or other solubilizing or dispersing agents such as those known in the art. Compositions for rectal administration include, for example, suppositories which may contain a suitable non-irritating excipient, such as cocoa butter, synthetic glyceride esters or polyethylene glycols, which are solid at ordinary temperatures, but liquify and/or dissolve in the rectal cavity to release the drug.

For human and veterinary administration, compositions of the present invention may meet sterility, pyrogenicity, and general safety and purity standards as required by federal regulatory agencies, such as the FDA. Such compositions are considered suitable for parenteral or enteral administration to a mammal. Such compositions may be pyrogen-free.

In accordance with the present invention, trypanocidal peptides may be administered in combination with the administration of one or more previously known treatment modalities. As used herein, the term "additional therapeutic agent" represents one or more agents previously known to be effective for the treatment of a protozoan disease or other conditions. Such an additional therapeutic agent is not a trypanocidal peptide. The administration of a trypanocidal peptide may take place before, during, and/or after the administration of the other mode of therapy. The present invention includes methods of administering one or more trypanocidal peptides in combination with the administration of one or more previously known treatment modalities. The present invention includes compositions of one or more trypanocidal peptides and one or more previously known treatment modalities.

In some embodiments of the present invention, the administration of a trypanocidal peptide in combination with additional therapeutic agents may demonstrate therapeutic synergy. Likewise, the administration of two or more trypanocidal peptides may demonstrate therapeutic synergy. As used herein, a combination may demonstrate therapeutic synergy if it is therapeutically superior to one or other of the constituents used at its optimum dose (Corbett et al., 1982, *Cancer Treatment Reports;* 66:1187. In some embodiments, a combination demonstrates therapeutic synergy if the efficacy of a combination is characterized as more than additive actions of each constituent.

Liposomes are currently used as drug carriers for a variety of antitumor agents, antiinflammatory agents and the like. The present invention also includes liposomes, lipid carriers, complexes, mixtures, supramolecular structures, multimolecular aggregates as lipid-based drug delivery systems including one or more trypanocidal peptides. Such liposomes or liposome-like compositions may be in the form of a monolayer, bilayer, multimolecular aggregate, vesicle, helix, disc, tube, fiber, torus, hexagonal phase, gel phase, liquid-crystalline phase, liquid-crystalline multimolecular aggregate, micelle, reverse micelle, microemulsion, emulsion, microreservoir, oil globule, fat globule, wax globule and/or colloidal particle. Such liposomes and liposome-like compositions may further include additional agents, including, for example, additional therapeutic agents and/or targeting moieties, including, but not limited to, RNA apatamers. Such liposomes or liposome-like compositions including one or more trypanocidal peptides may be used in any of the methods described herein.

Compositions of the invention may further include one or more targeting moieties against parasite target molecules. Compositions including such targeting moieties may be used in any of the methods described herein. Targeting moieties include, but are not limited to, high-affinity nucleic acid ligands, also referred to as DNA aptamers and RNA aptamers, that bind with high affinity and high specificity to parasite target molecules. For example, a number of trypanosome-specific RNA aptamers that bind with high affinity and high specificity to the variant surface glycoprotein or to an invariant surface domain of live African trypanosomes have been identified. See, for example, Goringer et al., 20003, *Int J Parasitol;* 33(12):1309-17; Lorger et al., 2003, *Eukaryot Cell;* 2(1):84-94; Goringer et al., 2006, *Handb Exp Pharmacol;* (173):375-93; Homann et al., 2006, *Comb Chem High Throughput Screen;* 9(7):491-9; and Adler et al., 2008, *Comb Chem High Throughput Screen;* 11(1):16-23. Any of such RNA aptamers may be used in the compositions and methods of the present invention.

Many therapeutic agents possess a high degree of hydrophobicity which can impede their solubilization in aqueous media and thus hamper their oral or parenteral administration. Compositions of the present invention may include formulations that facilitate the solubilization and/or delivery of hydrophobic drugs. Such formulations may include any of a variety of such formulations, including, but not limited to, amphiphilic polymers, lipid-based nanocapsules, nanoformulations, polymeric micelles, magnetic nanocarriers, nano-sized carriers that contain a hydrophobic core, polymeric vectors, lipidic vectors, emulsions, lipid emulsions, and microemulsions. Such formulations may include any of the formulations described herein, such as for example, alcohol and dimethyl sulfoxide (DMSO).

The present invention is illustrated by the following examples. It is to be understood that the particular examples, materials, amounts, and procedures are to be interpreted broadly in accordance with the scope and spirit of the invention as set forth herein.

EXAMPLES

Example 1

Novel Antimicrobial Peptides Derived from Human Apolipoproteins

This example demonstrates that a small peptide derived from the human haptoglobin related protein (Hpr) exhibits potent and specific killing of African trypanosomes. The peptide acts upon the cell membrane of the trypanosome, inducing a rigidification of the bilayer lipids and subsequent cell death. The amino acid sequence of the peptide is based upon the N-terminal signal sequence of Hpr. Hpr is a secreted protein that associates with high density lipoproteins (HDL). It is unusual in that it is secreted without cleavage of its N-terminal signal sequence. Only two other proteins are known that exhibit this phenomenon, paraoxonase 1 and apolipoprotein M, both of which associate with HDL. This small 19 amino acid peptide, based upon the signal sequence of Hpr can be used as a therapeutic agent in the treatment of mammalian pathogens, particularly *Trypanosoma brucei*, the causative agent of African sleeping sickness. Currently, there are approximately 500,000 infected people in sub-Saharan nations. Treatment of infected individuals is limited and there is an alarming increase in the number of relapses from established drug treatment (Brun et al., 2001, *Trop Med Int Health;* 6:906-914). Few new drugs are currently under clinical trials, and one of the more promising compounds, DB75, has already shown a marked tendency to induce drug resistance (Lanteri et al., 2006, *Mol Pharmacol;* 70:1585-1592). Based upon the ancient evolutionary origin of antimicrobial peptides that target cell membranes and their abundance in all branches of life, it is likely that drug resistance will develop slowly, if at all, to the peptide of the present invention.

Haptoglobin related protein (Hpr) is a component of the trypanolytic human high density lipoprotein, termed trypanosome lytic factor (TLF). Unusual for secreted proteins, Hpr retains its N-terminal 19 amino acid signal peptide (Smith et al. 1995, *Science;* 268(5208):284-286). Native, delipidated Hpr has been shown to be cytotoxic to *Trypanosoma brucei* (Shiflett et al., 2005, *J Biol Chem;* 280(38):32578-32585). This example shows that trypanosome killing by Hpr is dependent upon the presence of the hydrophobic signal peptide and that a synthetic peptide corresponding to the signal sequence is sufficient for killing. Indeed, the synthetic Hpr signal peptide (Hpr-SP) specifically kills bloodstream, but not procyclic form *T. brucei*, is not inhibited by the serum resistance associated protein, which is responsible for evasion of TLF killing in *T. b. rhodesiense* (Hager and Hajduk, 1997, *Nature;* 385(6619):823-826), and Hpr-SP appears to act at the surface of the trypanosome. In vitro studies with model liposomes suggests that bloodstream form *T. brucei* are uniquely susceptible to killing by the peptide due to the acyl chain composition of their cellular membrane. Due to the VSG coat, bloodstream form *T. brucei* have a high content of relatively short myristoyl acyl chains (14 carbon, saturated) (Ferguson et al., 1985, *J Biol Chem;* 260(27):14547-14555; and Ferguson et al., 1985, *J Biol Chem;* 260(8):4963-4968), whereas the signal peptide resistant procyclic form *T. brucei* (the developmental stage found within the insect vector) contain a larger content of palmitoyl (16 carbon, saturated) and stearoyl (18 carbon, saturated) chains (Treumann et al., 1997, *J Mol Biol;* 269(4):529-547), providing for greater van der Waals interactions within the bilayer, possibly inhibiting signal peptide penetration. Data show that the Hpr-SP is not toxic towards mammalian cells, thus it may provide a novel therapeutic for treatment of African trypanosomiasis.

Materials and Methods

Peptides. Synthetic peptides corresponding to the 19 amino acid N-terminal signal peptide of Hpr (MSDLGAVIS-LLLWGRQLFA) (SEQ ID NO:1) were purchased from Bio-Synthesis, Inc. (Lewisville, Tex.). Non-specific, hydrophilic peptides (ERTEESWGRRFWRRGEAC) (SEQ ID NO:10) were predicted from the N-terminus of the alternatively edited protein-1 (AEP-1) from mitochondria of *T. b. brucei* (Ochsenreiter and Hajduk, 2006, *EMBO;* 7(11):1128-1133) and purchased from Alpha Diagnostic (San Antonio, Tex.).

Lipids. All lipids were purchased from Avanti Polar Lipids (Alabaster, Ala.). These include phosphatidylcholine from egg (#840051) and 1,2-distearoyl-sn-glycero-3-phosphocholine (DSPC) (#850365).

Trypanosome lysis assays. Trypanosomes were cultured in the appropriate media and incubated at a cell density of $3 \times 10^6$ cells/ml with the addition of peptide from a 10 mg/ml stock in DMSO, or control reagents for 2 hours (h) at 37° C. Lysis of bloodstream form trypanosomes was evaluated by phase-contrast microscopy. Procyclic form trypanosomes were stained with 0.1% trypan blue. Trypan blue staining was also used for some bloodstream form assays to eliminate any possible discrepancy between the procyclic and bloodstream form assays. No difference was observed with the presence of trypan blue in bloodstream form lysis assays.

Mammalian cell viability assays. Human embryonic kidney cells (HEK, ATCC #CRL-1573) were cultured in Eagle's Minimum Essential Medium supplemented with 10% fetal bovine serum. Cell viability after treatment with Hpr-SP or the relevant controls was determined via trypan blue exclusion. Briefly, cells were plated at approximately 50-60% confluency into 96-well poly-lysine coated microtiter plates. Serial dilutions of Hpr-SP from a 10 mg/ml stock in DMSO were added and the cells were incubated for 2 hours at 37° C. Positive killing controls were serial dilutions of melittin, a membrane permeabilizing peptide from honey bee venom.

Anisotropy assays. Bloodstream form trypanosomes were washed and resuspended at $3 \times 10^6$ cells/ml in phosphate buffered saline. The anisotropic probe trimethylammonium-1,6-diphenyl-1,3,5-hexatriene (TMA-DPH) was added to a concentration of 0.2 µM and allowed to intercalate into the cell membrane for 15 minutes (min) at ambient temperature (25° C.). The anisotropic value was acquired with a Perkin Elmer Life Sciences fluorescence spectrophotometer LS-55 with excitation at 358 nm and emission read at 430 nm, both with 10 nm slit widths. Values expressed were determined immediately after the addition of Hpr-SP or DMSO only and are the average of three independent assays (except for no addition and 0.167% DMSO). The anisotropy values did not change over the course of an hour.

Liposome permeabilization assays. Liposomes were constructed by hydration of dried lipid films with 10 mM Hepes and 30 mM calcein to a final lipid concentration of 10 mg/ml. Resulting multilamellar liposomes were extruded through a 0.1 polycarbonate filter at temperatures above the transition point of the particular lipid mixture. Untapped calcein was removed by gel filtration (Sephacryl S-300 HR). Permeabilization of liposomes was monitored fluorimetrically with a Perkin Elmer LS-55 luminescent spectrophotometer. Assays were performed by diluting liposomes 1:1000 into the appropriate buffer and monitoring fluorescence when excited by 484 nm light (5 nm slit width) and reading the emission intensity at 513 nm (10 nm slit widths). The percentage calcein release was calculated relative to the 100% fluorescence intensity, achieved by the addition of 0.01% Triton X-100.

Results

Hpr-SP is sufficient for trypanolysis. Based upon the necessity of the Hpr-SP for killing activity by Hpr, the trypanolytic activity of a synthetic peptide corresponding to the 19-amino acids of Hpr-SP was investigated. Addition of Hpr-SP to bloodstream form trypanosomes efficiently killed cells in a dose dependent fashion. The Hpr-SP solubilizing agent DMSO did not exhibit toxicity at concentrations equal to the highest dosage of Hpr-SP tested. The morphology of Hpr-SP killed trypanosomes is dramatic and distinct from cells killed by TLF. Excessive fraying of the cellular membrane, and what appears to be leakage of cytoplasmic contents is apparent. These data suggest that the mechanism of Hpr-SP trypanosome killing is quite different than that employed by TLF. FIG. 1A shows the killing of *T. b. brucei* by the Hpr-SP. Wild type 427 *T. b. brucei* cells were incubated with increasing concentrations of Hpr-SP (8-80 µM) added from a stock solution in DMSO. Positive controls were trypanosome lytic factor (TLF). Addition of equivolume DMSO or equimolar concentrations of a non-specific hydrophilic 19 amino acid peptide (NS 19mer; SEQ ID NO:10) gave no trypanolysis. The inset in FIG. 1A shows cells treated with Hpr-SP. FIG. 1B presents a cartoon of Hpr and the derived peptide Hpr-SP (SEQ ID NO:1). Hydrophobic residues are in bold.

Hpr-SP kills SRA-expressing *T. brucei* and exhibits specificity for bloodstream form trypanosomes. The trypanolytic activity of Hpr-SP against procyclic trypanosomes (the insect stage form which dramatically down regulates endocytic activity) was assayed. Surprisingly, only very minor trypanolytic activity was found against these cells (>20% at 80 µM Hpr-SP). This discrepancy may be accounted for by the different compositions of the bloodstream and procyclic form trypanosome membranes. Because the Hpr-SP is derived from TLF, we asked whether SRA, the protein responsible for inhibiting TLF killing in the human pathogenic trypanosome strain *T. b. rhodesiense*, provided protection against Hpr-SP mediated killing. SRA expressing trypanosomes were killed with identical activity as non-SRA expressing *T. b. brucei*. The morphology of Hpr-SP killed trypanosomes is dramatic and distinct from cells killed by TLF. Excessive fraying of the cellular membrane, and what appears to be leakage of cytoplasmic contents is apparent. These data suggest that the mechanism of Hpr-SP trypanosome killing is quite different than that employed by TLF.

Figure 2:
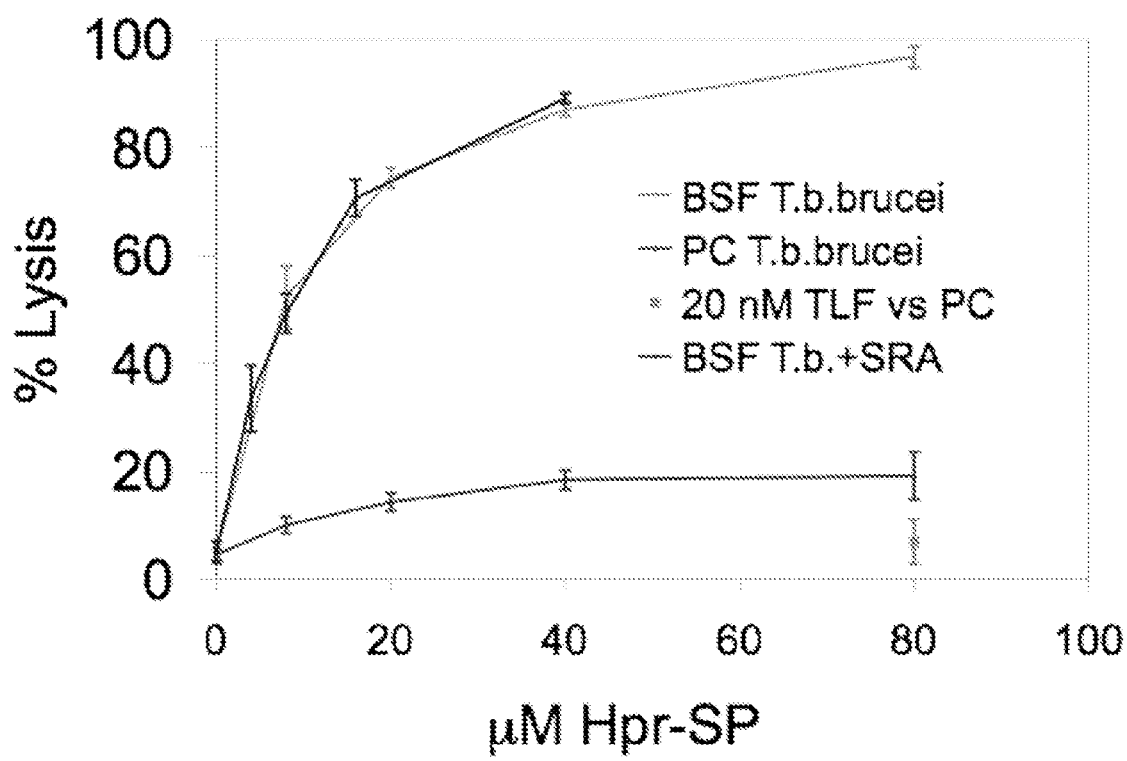
FIG. 2 shows the results of lysis assays conducted with $T. b. brucei$ expressing SRA or procyclic form $T. b. brucei$.

In FIG. 2, lysis assays were conducted with *T. b. brucei* expressing SRA or procyclic form *T. b. brucei*. SRA protects human pathogenic *T. b. rhodesiense* from the lytic activity of TLF. However, SRA offers no protection against Hpr-SP. Procylic form *T. b. brucei* are inefficiently killed by Hpr-Sp. As discussed below, it may be the case that a higher content of stearoyl acyl chains in the trypanosome membrane protects against the lytic effect of the small highly hydrophobic Hpr-Sp.

Hpr-SP acts at the cytoplasmic membrane of bloodstream form trypanosomes. A diagnostic feature of TLF killing is the necessity for trafficking to the lysosome of the target trypanosome, where the acidic environment activates a membrane disruptive activity by TLF. Therefore we asked if compounds that inhibit the acidification of the lysosome (and are known inhibitors of TLF) block the killing activity of Hpr-SP. Thus, lysis assays were performed with Hpr-SP in the presence of 10 mM $NH_4Cl$ or 50 µM chloroquine. No inhibitory effect by these pH neutralizing agents was found, suggesting that either Hpr-Sp is endocytosed but does not require acidic conditions or that the peptide acts at the surface of the target trypanosome. In order to answer this question, lysis assays were performed at 3° C., a temperature that effectively halts endocytosis. Robust trypanolysis was observed, equivalent to activity observed at 37° C., indicating that the Hpr-SP does not require cellular uptake to exert its toxic effects.

Figure 3:
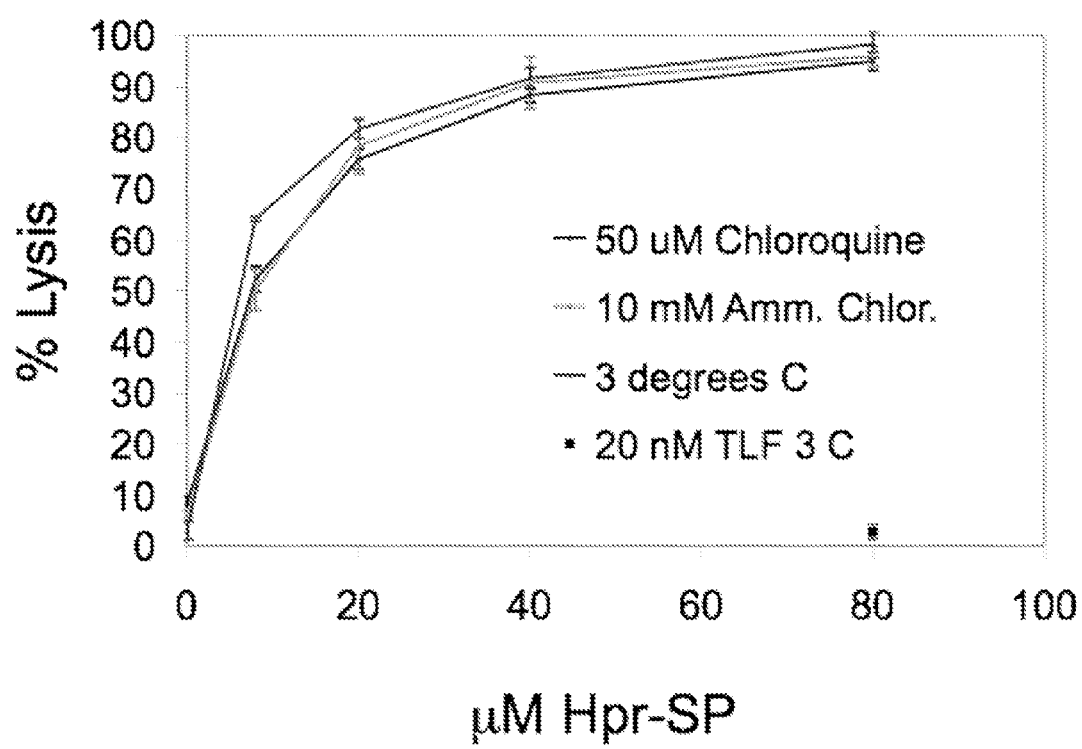
FIG. 3 presents the results of lysis assays in the presence of chloroquine, NH$_4$Cl or at 3° C.

In FIG. 3, the site of action was probed by conducting lysis assays in the presence of chloroquine, $NH_4Cl$, or at 3° C. Inhibiting the acidification of the lysosomes with either chloroquine $NH_4Cl$, protects against TLF killing. No inhibition of Hpr-Sp was observed, suggesting that Hpr-SP does not require targeting tp the intracellular compartment. Endocytosis was inhibited by incubating *T. b. brucei* at 3° C. The Hpr-SP readily killed cells at the non-permissive temperature, confirming the cell surface as the site of action of Hpr-Sp.

Hpr-SP exhibits specificity of permeabilizing activity against different model membranes. In order to test the effect of membrane composition on the specificity displayed by Hpr-SP, a model liposome system was utilized in which we fluorescently monitored the leakage of dye from the liposome interior. Liposomes composed entirely of egg PC, a heterogeneous mixture with respect to the length and degree of unsaturations, are readily permeabilized by nanomolar concentrations of Hpr-SP. Permeabilizing activity was robust at pH 6.8, consistent with the ability of Hpr-SP to target trypanosomal membranes in the extracellular medium. However, when Hpr-SP permeabilizing activity against liposomes composed entirely of DSPC, 18-carbon saturated lipids, no permeabilizing activity at neutral or acidic pH was found. This suggests that either the Hpr-SP is incapable of intercalating into the hydrophobic regions of the DSPC bilayer or that intercalation of the peptide is incapable of producing sufficient destabilization, and thus permeability increase, of the DSCP bilayer.

Figure 4:
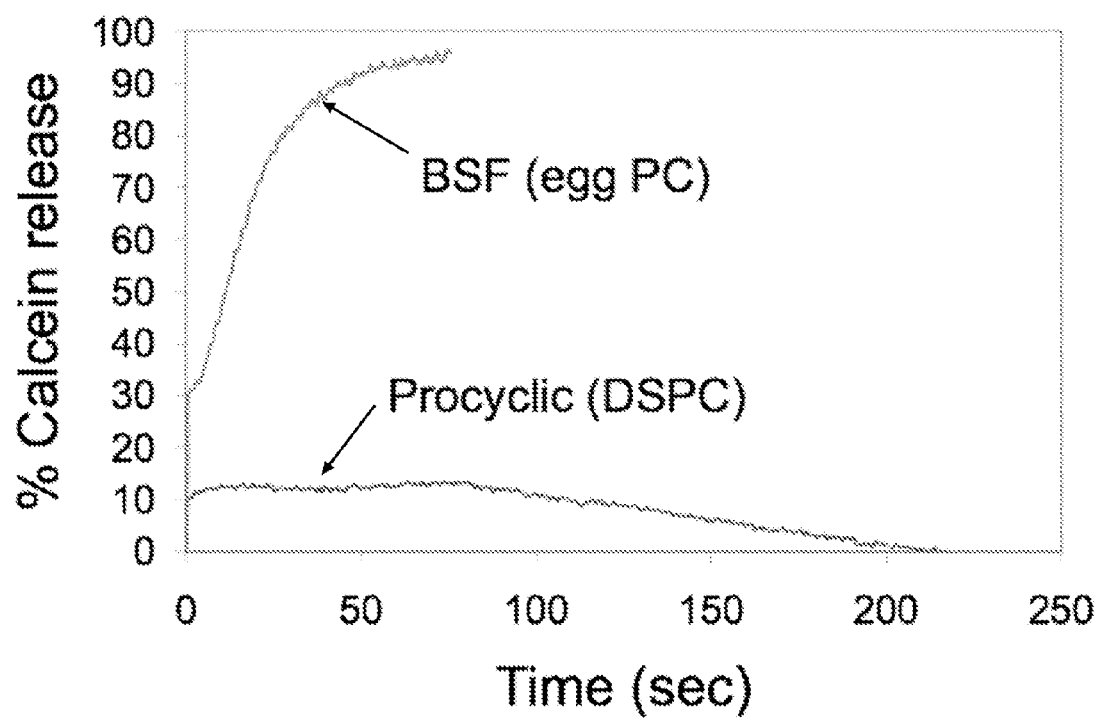
FIG. 4 shows modeling of $T. b. brucei$ cellular membranes with liposomes. Artificial vesicles were constructed with the phosphatidylcholines corresponding in acyl chain composition to either the VSG or procyclin lipid anchors, egg phosphatidylcholine (egg PC, transition temperature<0° C.) for VSG and distearoylphosphatidylcholine (DSPS) for procyclin. The leakage of liposomally entrapped calcein was fluorescently monitored as an indicator of Hpr-SP membrane interaction.

FIG. 4 shows modeling of *T. b. brucei* cellular membranes with liposomes. Artificial vesicles were constructed with the phosphatidylcholines corresponding in acyl chain composition to either the VSG or procyclin lipid anchors, egg phosphatidylcholine (eggPC, transition temperature<0° C.) for VSG and distearoylphosphatidylcholine (DSPS) for procyclin. The leakage of liposomally entrapped calcein was fluorescently monitored as an indicator of Hpr-SP membrane interaction.

Hpr-SP induces a rigidification of the bilayer lipids in *T. brucei*. In order to understand the effect of Hpr-SP on the cell membrane of target trypanosomes the lipid bilayer fluidity of trypanosomes treated with Hpr-SP was analyzed via anisotropy determinations. The addition of lytic concentrations of Hpr-SP induced a rigidity increase, i.e. a constriction of rotational and lateral motion of the lipid components, in the cell membrane. These data are particularly important as bloodstream form trypanosomes rely upon a fluid membrane to recycle their VSG coat and thus avoid killing mediated by host antibodies.

Figure 5:
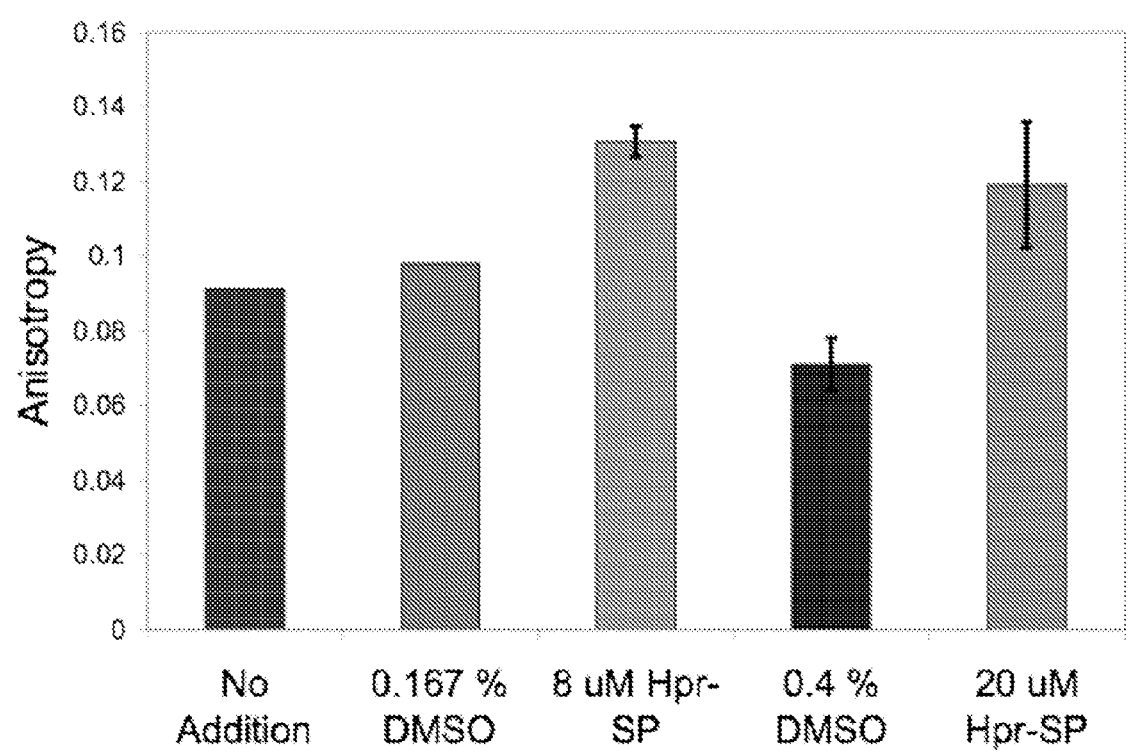
FIG. 5 monitors membrane rigidity in live $T. b. brucei$ with the anisotropic probe TMA-DPH. The addition of Hpr-SP results in an increase in the anisotropy of TMA-DPH labeled cells, indicating membrane rigidification. Equivolmes of DMSO, the Hpr-SP solvent, results in either no change (0.167% DMSO corresponding to 8 µM Hpr-SP) or a decrease (0.4% DMSO corresponding to 20 µM Hpr-SP) in membrane rigidity.

In FIG. 5, membrane rigidity in live *T. b. brucei* was monitored with the anisotropic probe TMA-DPH. The addition of Hpr-SP results in an increase in the anisotropy of TMA-DPH labeled cells, indicating membrane rigidification. Equivolmes of DMSO, the Hpr-SP solvent, results in either no change (0.167% DMSO corresponding to 8 µM Hpr-SP) or a decrease (0.4% DMSO corresponding to 20 µM Hpr-SP) in membrane rigidity. Modulation of the membrane fluidity may contribute to the cytotoxity of Hpr-SP.

Hpr-SP is not toxic towards mammalian cells. The potential toxicity of Hpr-SP towards human cells was assayed by determining the effect of exogenous Hpr-SP on the viability of human embryonic kidney cells. No toxicity was observed towards these cells by Hpr-SP or equivolume addition of DMSO, the solubilizing agent. These data are not unexpected as Hpr-SP is an endogenously derived molecule that is associated with hepatic cell membranes.

Figure 6:
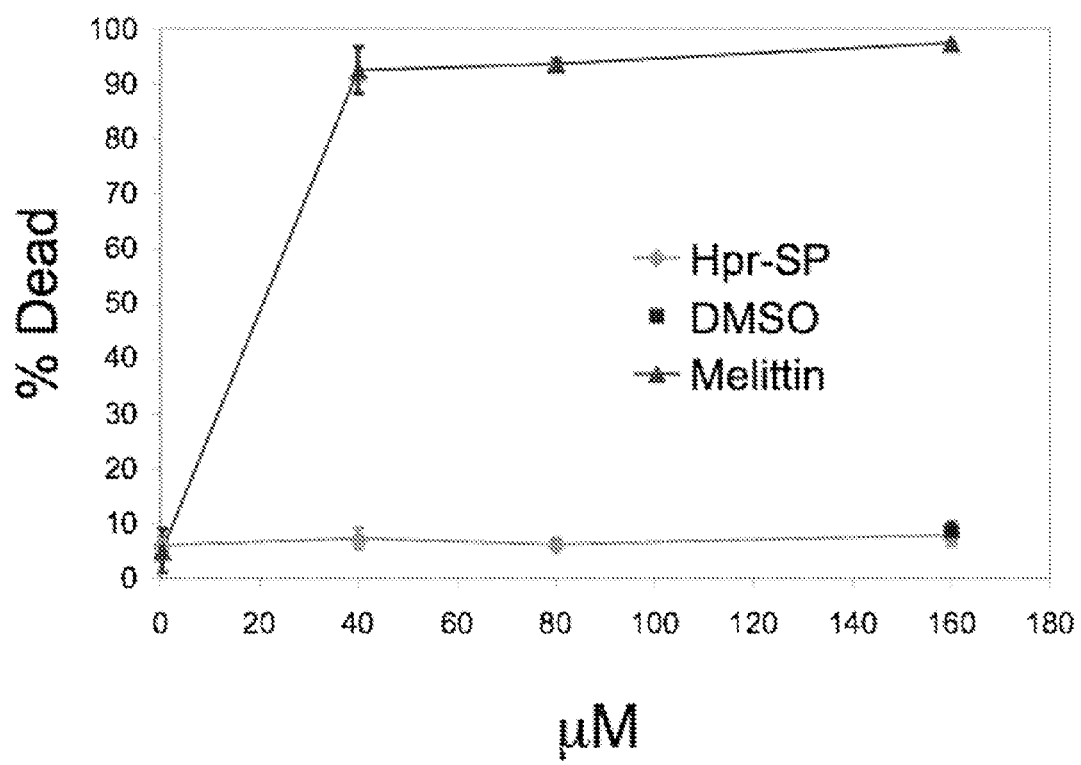
FIG. 6 assayed cell viability via trypan blue exclusion. Human embryonic kidney cells were incubated with increasing concentrations of Hpr-Sp for two hours at 37° C. No cell death was observed with trypanolytic concentrations of Hpr-SP or equivolume addition of DMSO. Positive killing controls provided by the lytic peptide melittin.

In FIG. 6, cell viability was assayed via trypan blue exclusion. Human embryonic kidney cells were incubated with increasing concentrations of Hpr-Sp for two hours at 37° C. No cell death was observed with trypanolytic concentrations of Hpr-SP or equivolume addition of DMSO. Positive killing controls provided by the lytic peptide melittin. Lack of cytotoxicity against mammalian cells suggest that Hpr-SP provide a novel therapeutic strategy for treating African trypanosomiasis.

In conclusion, this example demonstrates that the N-terminal signal sequence of Hpr is sufficient for trypanosome killing; that Hpr-SP exhibits specificity for BSF form *T. b. brucei* and evades the protective effect of SRA; that Hpr-SP acts at the surface of target trypanosomes, inducing a rigidification of the lipid bilayer; and that the lack of toxicity towards mammalian cells support Hpr-SP as a therapeutic agent.

Discussion

Previous studies had revealed that human Hpr, a protein encoded by a gene that evolved during primate evolution, was toxic to trypanosomes and when assembled in TLF, with another primate specific protein, ApoL-1, had a high specific activity for killing trypanosomes (Shiflett et al., 2005, *J Biol Chem*; 280(38):32578-32585). Studies to characterize the mechanism of Hpr killing revealed that Hpr was unusual in that it contained an unprocessed N-terminal signal peptide (Hpr-SP). Deletion of the Hpr-SP inactivated recombinant Hpr (Vanhollebeke et al., 2007, *PNAS*; 104(10):4118-4123). The 19 amino acid Hpr-SP was synthesized and tested for trypanosome killing activity. Hpr-SP damage to the trypanosomes is striking. Cells rapidly fragment and the rate of killing is independent of temperature. On the other hand, TLF killing of trypanosomes requires endocytosis and lysosomal trafficking, has a characteristic lag phase of ~20 min and killing activity is completely blocked at temperatures below 4° C. When human embryonic kidney cells were incubated at the same concentration of Hpr-SP no toxicity was observed, indicating the Hpr-SP selectively interacts with trypanosomes.

These results show that Hpr-SP is highly toxic to trypanosomes, at low μM concentrations, and acts rapidly at the cell surface. In addition, mammalian cells are resistant to Hpr-SP. The rigidification increase seen upon addition of Hpr-SP to bloodstream form trypanosomes may be directly involved in the cytotoxicity of the peptide. *T. brucei* rapidly turn over a dense protein surface coat through endocytosis at a specific site at the posterior of the cell (Engstler et al., 2007, *Cell;* 131(3):505-515). This turnover facilitates evasion from the host immune system. The fluidity of the cell membrane has been directly implicated in this process as the proteins are swept backwards towards the endocytic site by outside physical forces, i.e. the flow of the extracellular environment. In this regard it may even be the case that the peptide will facilitate immune destruction of trypanosomes by blocking the turnover of the cellular protein coat.

Example 2

Plasma Membrane of Bloodstream Form African Trypanosomes Confers Susceptibility and Specificity to Killing by Hydrophobic Peptides The developmental stage of *T. brucei* found within the mammalian host, the bloodstream form (BSF), is a highly motile cell (Rodriguez et al., 2009, *PNAS;* 106(46):19322-19327; and Oberholzer et al., 2010, *PLoS Pathog;* 6(1): e1000739), exhibits rapid rates of endocytosis (Engstler et al., 2004, *J Cell Sci;* 117(Pt 7):1105-1115) and free diffusion of densely packed GPI-anchored proteins (Bulow et al., 1988, *Biochem;* 27(7):2384-2388). Endocytosis is restricted to the flagellar pocket, a small, specialized membrane structure at the posterior of the cell (Field and Carrington, 2009, *Nature Rev;* 7(11):775-786). This morphology requires that surface associated cargo destined for endocytosis be laterally sorted in the plane of the membrane to the flagellar pocket. Perhaps the most striking example of this activity is the sorting of immunoglobulin bound variant surface glycoproteins (VSG) to the flagellar pocket by physical forces generated from the flow of extracellular medium over the surface of the trypanosome (Engstler et al. Al., 2007, *Cell;* 131(3):505-515). The nature of the trypanosome plasma membrane that facilitates rapid lateral sorting is not known. In the case of VSG, surface flow may benefit from the use of myristate, a relatively short acyl chain, as the membrane-anchoring moiety (Ferguson et al., 1985, *J Biol Chem;* 260(27):14547-14555; and Ferguson et al., (1985), *J Biol Chem,* 260(8):4963-4968). The procyclic form (PCF) *T. brucei,* found within the insect midgut, does not exhibit rapid rates of endocytosis (Langreth and Balber, 1975, *J Protozool;* 22(1):40-53; and Morgan et al., 2001, *J Cell Sci;* 114(Pt 14):2605-2615) and the GPI-anchored procyclin surface proteins are anchored with longer palmitoyl and stearoyl acyl chains (Field et al., 1991, *EMBO;* 10(10): 2731-2739).

The structure of the plasma membrane is also important for avoiding lysis by host defense factors such as complement or antimicrobial peptides. The terminal components of the complement membrane attack complex are sterically hindered from assembling by the dense surface coat of VSG. Human defensins, antimicrobial peptides with a distinct tertiary structure, are relatively inefficient at killing BSF *T. brucei* (McGwire et al., 2003, *J Infect Dis;* 188(1):146-152) and it may be the case that the VSG coat inhibits interaction with the cell membrane. Interestingly BSF and PCF *T. brucei* exhibit differential susceptibility to a number of antimicrobial peptides (McGwire et al., 2003, *J Infect Dis;* 188(1):146-152). This distinction may be attributed to the different surface density of GPI-anchored proteins between the two forms, VSG being present at roughly an order of magnitude greater than procylin, thereby providing greater steric hinderance. Alternatively, or in addition to the difference in surface protein density, the differences in phospholipid and sterol composition between the two developmental forms may play a role.

The present example describes the trypanocidal activity of a small hydrophobic peptide (SHP-1), derived from the signal sequence of a human apolipoprotein, haptoglobin related protein (Hpr), which circumvents steric hinderance from the VSG coat and interacts with the plasma membrane of BSF *T. brucei*. This example shows that this non-cationic peptide specifically targets fluid membranes. The SHP-1 rapidly binds BSF cells rather than PCF or mammalian cells. Consistently, BSF *T. brucei* are readily killed by SHP-1 and no lysis or killing is observed with PCF T. brucei, mammalian cells or human erythrocytes.

Methods

Peptides. Synthetic peptides corresponding to the N-terminal signal peptide of human apolipoproteins haptoglobin related protein ("SHP-1," SDLGAVISLLLWGRQLFA (SEQ ID NO:2)), paraoxonase-1 ("SHP-2," (AKLIATLLGMGLA-LFRNHQS (SEQ ID NO:4)) (both without the N-terminal methionine residue) and all derivatives ("SHP-1-ΔL," SDL-GAVISLLWGRQLFA (SEQ ID NO:7); "SHP-1-ΔLLL," SDLGAVISWGRQLFA (SEQ ID NO:8); and "SBP-1-ΔLGA," SDVISLLLWGRQLFA (SEQ ID NO:9) were purchased from Bio-Synthesis, Inc. (Lewisville, Tex.). A non-specific, hydrophilic peptide (ERTEESWGRRFWRRGEAC (SEQ ID NO:10)) predicted from the N-terminus of the alternatively edited protein-1 from mitochondria of *T. b. brucei*, was purchased from Alpha Diagnostic (San Antonio, Tex.) (Ochsenreiter and Hajduk, 2006, *EMBO;* 7(11):1128-1133).

Lipids. All lipids were purchased from Avanti Polar Lipids (Alabaster, Ala.). These include phosphatidylcholine from egg (egg PC, #840051), 1,2-distearoyl-sn-glycero-3-phosphocholine (DSPC) (#850365), 1,2-diheptadecanoyl-sn-glycero-3-phosphocholine (#850360), 1,2-dipalmitoyl-sn-glycero-3-phosphocholine (DPPC) (#850355), 1,2-dipentadecanoyl-sn-glycero-3-phosphocholine (#850350), 1,2-dimyristoyl-sn-glycero-3-phosphocholine (DMPC) (#850345), 1-palmitoyl-2-oleoyl-sn-glycero-3-phosphocholine (POPC) (#850457) and (#850467).

Trypanosome killing assays. Bloodstream form *T. b. brucei* Lister 427 (MiTat 1.2), *T. b. gambiense* type 1 (Eliane strain) and *T. b. rhodesiense* KETR12482 were used in these studies. Trypanosome killing assays were performed as described previously (Hajduk et al., 1989, *J Biol Chem;* 264(9):5210-5217; Shiflett et al., 2005, *J Biol Chem;* 280(38):32578-32585; and Widener et al., 2007, *PLoS Pathog;* 3(9):1250-1261). Cultured trypanosomes (except for T. b. gambiense which were incubated at $1 \times 10^6$ cells/ml) were incubated in HMI-9 media (BSF) or SM media (PCF) at a density of $1 \times 10^7$ cells/ml containing either 10% heat inactivated fetal bovine serum or bovine serum albumin and peptide or control reagents for two hours at 37° C. Killing of BSF trypanosomes was evaluated by phase-contrast microscopy. Procyclic form trypanosomes were stained with 0.1% trypan blue. Trypan blue staining was also used for some BSF assays to eliminate any possible discrepancy between the PCF and BSF assays. Trypan blue was added at the endpoint of each assay to avoid any toxic effects. No difference was observed with the presence of trypan blue in BSF killing assays.

Mammalian cell viability and hemolysis assays. Human embryonic kidney cells (HEK) (ATCC CRL-1573) and LNCaP prostate cancer cells (ATCC CRL-1740) were utilized for cell viability assays. Human embryonic kidney cells were cultured in Dulbecco's Modified Eagles Medium, high glucose (Thermo Scientific, cat #SH30243.01) with 10% fetal bovine serum at 37° C. and 5% $CO_2$. Prostate cancer cells were cultured in RPMI-1640 medium (Invitrogen, cat #A10491-01) with 10% fetal bovine serum at 37° C. and 5% $CO_2$. In both cases, assays were performed by aliquoting cells into 96 well plates at approximately 60% confluency and allowing the cells to adhere for two hours. Cells were then incubated with serial dilutions of SHP-1, or the relevant control, in the corresponding media for two hours at 37° C. Cell viability was determined by the ability of live cells to exclude trypan blue. The cells were incubated with 0.1% trypan blue for 10 minutes and examined microscopically for cytoplasmic staining. The potential for SHP-1 to induce hemolysis was assayed by monitoring hemoglobin (Hb) release from freshly collected human erythrocytes that had been washed and incubated with SHP-1 in PBS. The Hb concentration of the supernatant was determined by the absorbance at 412 nm and compared to 100% hemolysis acquired by hypotonic lysis. The membrane permeabilizing peptide, melittin, was used a positive control for killing or hemolysis.

Microscopy. All images were acquired with an Axio Observer Z1 equipped with an Axiocam MRm controlled by the Axiovision 4.6 software or a Zeiss Imager A1. Fluorescent microscopy with Texas Red-labelled SHP-1 was performed by incubating $3 \times 10^6$ cells/ml with 8 µM TR-Hpr-SP in media for 10 min before fixing with 1% paraformaldehyde for 1 min, air drying on glass slides and covering with DAPI containing antifade reagent ProlongGold (Molecular Probes). Videos were acquired with live cells at a density of $3 \times 10^6$ cells/ml incubated with the indicated concentration of SHP-1 at 37° C. Movies were recorded at 63× magnification at 50 msec acquisition times for normal and constricted motion trypanosomes and 25 msec acquisition times for hyperactivated trypanosomes. Visualized trypanosomes presented in supplementary movies were centered in the videos by digital tracking with Final Cut software (Apple) and videos were looped to facilitate comparisons.

Flow cytometry. Peptide binding to cells was monitored by flow cytometry. Binding assays were performed with $3 \times 10^6$ cells/ml in PBS at 25° C. Texas red-labelled SHP-1 was added to a final concentration of 0.8 µM and 50,000 cells were immediately counted with the CyAn ADP flow cytometer (Dako, available on the worldwide web at dako.com). Data were analyzed with FlowJo software (Treestar, available on the worldwide web at treestar.com).

Calcein release assays. Permeabilization of unilamellar liposomes was assayed as described previously (Harrington, et al., 2009, *J Biol Chem*; 284(20):13505-12). Briefly, liposomes were diluted 1:1000 into 50 mM Tris, pH 7.0 and calcein fluorescence was monitored at 513 nm when excited at 484 nm. The percent calcein release was calculated relative to the 100% fluorescence intensity, achieved by the addition of 0.01% Triton X-100.

Anisotropy assays. The membrane fluidity of live *T. b. brucei* was probed by measuring the fluorescence depolarization of 1-(4-trimethylammoniumphenyl)-6-phenyl-1,3,5-hexatriene p-toluenesulfonate (TMA-DPH) (Invitrogen, cat. #T204). Cells were washed twice with, and resuspended in PBS, or Voorheis's modified PBS (supplemented with 10 mM glucose, 79 mM sucrose) in the case of procyclic cells, at a density of $3 \times 10^6$ cells/ml. The anisotropic probe, TMA-DPH, was added to a final concentration of 0.5 µM and allowed to intercalate into the cell membrane for 15 min. Anisotropic values were acquired via the software function of the Perkin Elmer Life Sciences LS55. Samples were excited at 358 nm and emission was read at 430 nm, both with 10 nm slit widths.

Data was corrected for light scattering with an unlabeled sample of cells and anisotropy was calculated according to the equation, $r = (I_{VV} - GI_{VH})/(I_{VV} + 2GI_{VH})$, where r is the anisotropy value, $I_{VV}$ is the emission intensity acquired with the excitation and emission polarizing filters set vertically, G is the instrument correction factor and $I_{VH}$ is the emission intensity acquired with the excitation polarizing filter set vertically and the emission polarizing filter set horizontally. All assays were conducted at ambient temperature, ~25° C.

Results

Figure 7:
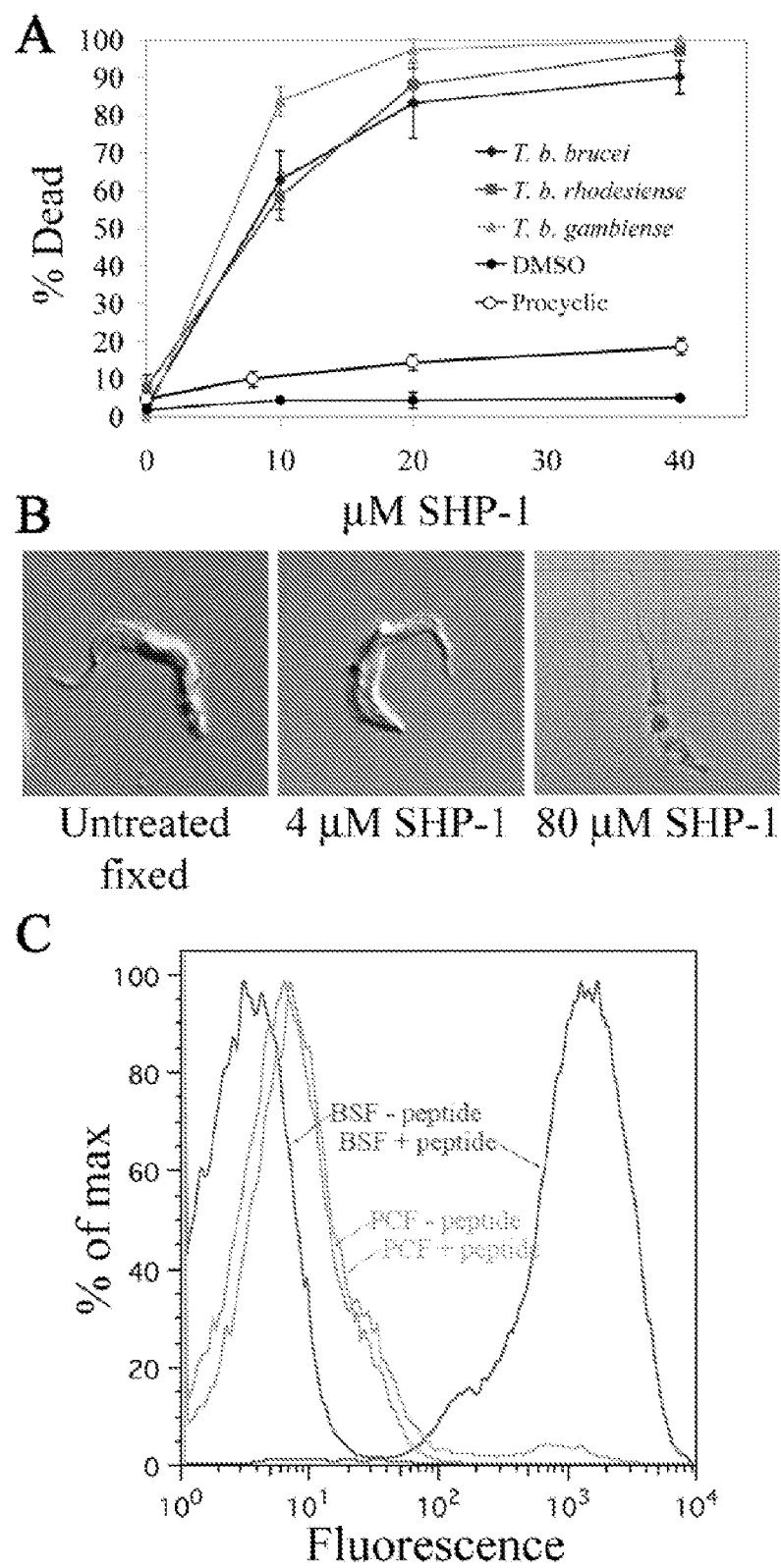
FIG. 7 demonstrates toxicity and specificity of SHP-1 for BSF African trypanosomes.

Small hydrophobic peptides specifically kill BSF African trypanosomes. IT has been previously reported that delipidated native human Hpr, purified from HDL, kills BSF *T. b. brucei* (Shiflett et al., 2005, *J Biol Chem*; 280(38):32578-32585; and Smith et al. 1995, *Science*; 268(5208):284-286). The lack of killing activity from a recombinant form of Hpr that lacks the N-terminal signal peptide (Vanhollebeke et al., 2007, *PNAS*; 104(10):4118-4123) led us to investigate the potential trypanocidal activity of a synthetic peptide corresponding to the signal sequence. Addition of SHP-1 to BSF *T. b. brucei* killed cells in a dose dependent fashion (FIG. 7A). Equivolume amounts of DMSO did not exhibit toxicity. The human pathogenic subspecies *T. b. rhodesiense* and *T. b. gambiense* are also sensitive to killing by SHP-1 (FIG. 7A). Cells treated with lower concentrations of SHP-1, ie. 4 µM, retain their elongated and twisted shape, and cell membranes appear completely intact, however cells are motionless and unable to exclude trypan blue (FIG. 7B). At higher concentrations of SHP-1, 40-80 µM, BSF trypanosomes retain their overall shape, however cellular membranes appear to have been stripped off or collapsed into the cytoplasm of the cells (FIG. 7B). Membrane degradation occurs subsequent to cell death, as revealed by video DIC microscopy.

SHP-1 exhibits specificity for BSF African trypanosomes. The specificity of SHP was initially examined by conducting killing assays with PCF *T. b. brucei*. No killing of PCF cells was observed (FIG. 7A). Flow cytometry was utilized to determine if the lack of PCF killing was due to a failure of SHP-1 to bind the PCF trypanosome (FIG. 7C). Texas-red SHP-1 rapidly binds BSF *T. brucei* as indicated by the labeling of the entire population of cells immediately after the addition of peptide. No labeling of PCF cells was observed immediately after addition of peptide indicating a dramatic difference in the affinity of SUP-1 for BSF and PCF trypanosomes.

Figure 8:
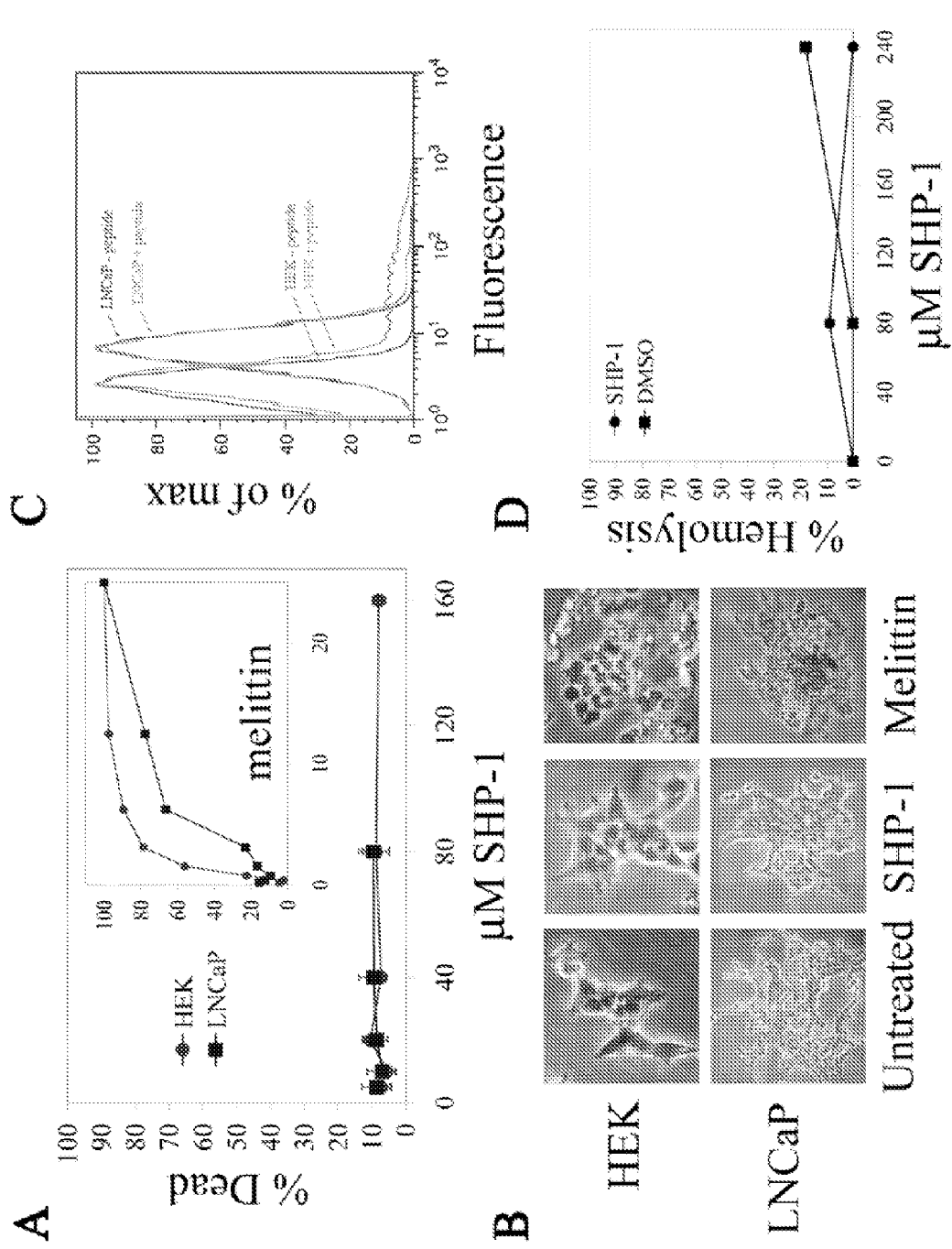
FIG. 8 demonstrates that SHP-1 is not toxic to mammalian cells.

The analysis of the spectrum of SHP-1 toxicity was broadened by testing the peptide against two human cell lines. Incubating human embryonic kidney cells (HEK) or prostate cancer cells (LNCaP) with relatively high concentrations of SHP-1, 80-160 µM, for 2 h at 37° C. did not result in cell death as evaluated by changes in morphology or the ability to exclude trypan blue (FIGS. 8A and 8B). Consistent with a lack of toxicity, flow cytometry indicated that these cells are not bound by SHP-1 (FIG. 8C). Additionally no hemolysis of freshly collected human erythrocytes incubated with 240 µM SHP-1, the highest concentration tested, was detected (FIG. 8D).

Figure 9:
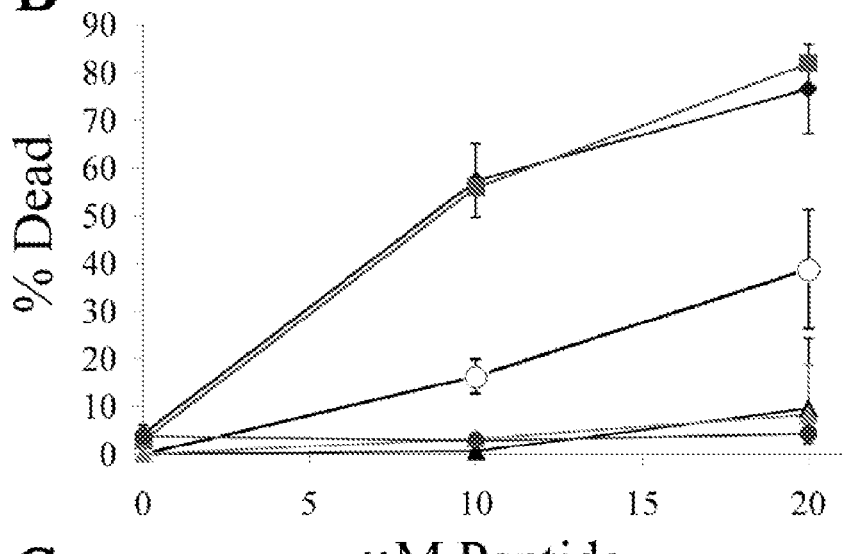
FIG. 9 presents hydrophobicity requirements for trypanosome killing by small peptides.
Figure 9:
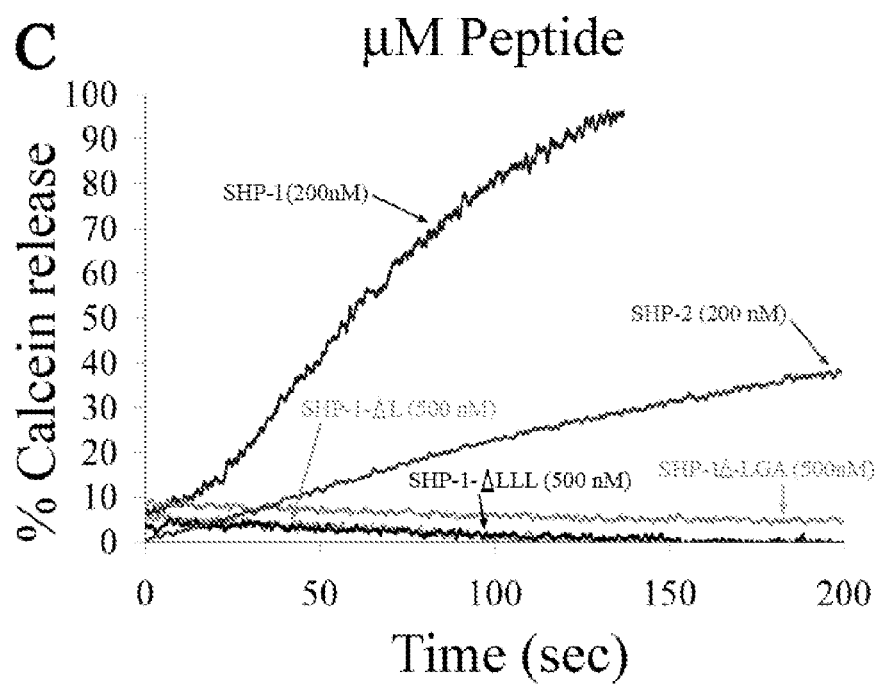

SHP-1 killing of BSF trypanosomes requires a hydrophobic stretch of amino acids. The sequence requirements for trypanocidal activity by SUP-1 (SEQ ID NO:2) were analyzed by conducting killing assays with synthetic peptides that mimicked, lessened or ablated the core hydrophobic region of SHP-1 (FIG. 9A). A peptide exhibiting similar hydrophobicity and length was derived from the signal sequence of the human apolipoprotein paraoxonase-1 (SHP-2) (SEQ ID NO:4) (Sorenson, 1999, *Arterioscler Thromb*

Vasc Biol; 19(9):2214-2225). Trypanocidal activity was observed against BSF *T. brucei* equivalent to SHP-1 (FIG. 9B). Conversely, a non-specific hydrophilic peptide of equal length to SHP-1 exhibited no toxicity (FIG. 9B). The size of the hydrophobic core of SHP-1 was decreased by a single leucine deletion from the C-terminal leucine triplicate (SEQ ID NO:7). Decreasing the length and hydrophobicity by a single amino acid resulted in a five-fold decrease in trypanocidal activity (FIG. 9B). Further deletions of the C-terminal leucine triplicate (SEQ ID NO:8) or the N-terminal leucine-glycine-alanine (SEQ ID NO:9) resulted in a complete lose of trypanosome killing activity (FIG. 9B).

The effect of altering peptide hydrophobicity on trypanosome killing suggested that membrane interaction might play a mechanistic role in SHP-1's trypanotoxicity. In an initial attempt to address this possibility, a model liposome system was utilized in which the release of internally trapped fluorophore, calcein, was monitored as an indicator of membrane interaction. The SHP-1 elicits calcein release from unilamellar liposomes composed of phosphatidylcholine (PC) from egg at nanomolar concentrations (FIG. 9C). Variant SHP peptides performed in the calcein release assay in a manner consistent with their ability to kill BSF trypanosomes, with a lack of liposome permeabilization by the deletion variants. The SHP-2 elicited calcein release, albeit reduced from SHP-1, while deleting a single leucine, the leucine truplicate or the leucine-glycine-alanine stretch resulted in a loss of permeabilizing activity at concentrations of 500 nM, the highest concentration tested (FIG. 9C).

These data indicate that, the amino acid sequence of SHP-1 is not strictly required but the necessary characteristic for trypanosome killing activity is a significantly high degree of hydrophobicity, and the ability to interact with lipid bilayers is consistent with the ability to kill BSF trypanosomes.

Figure 10:
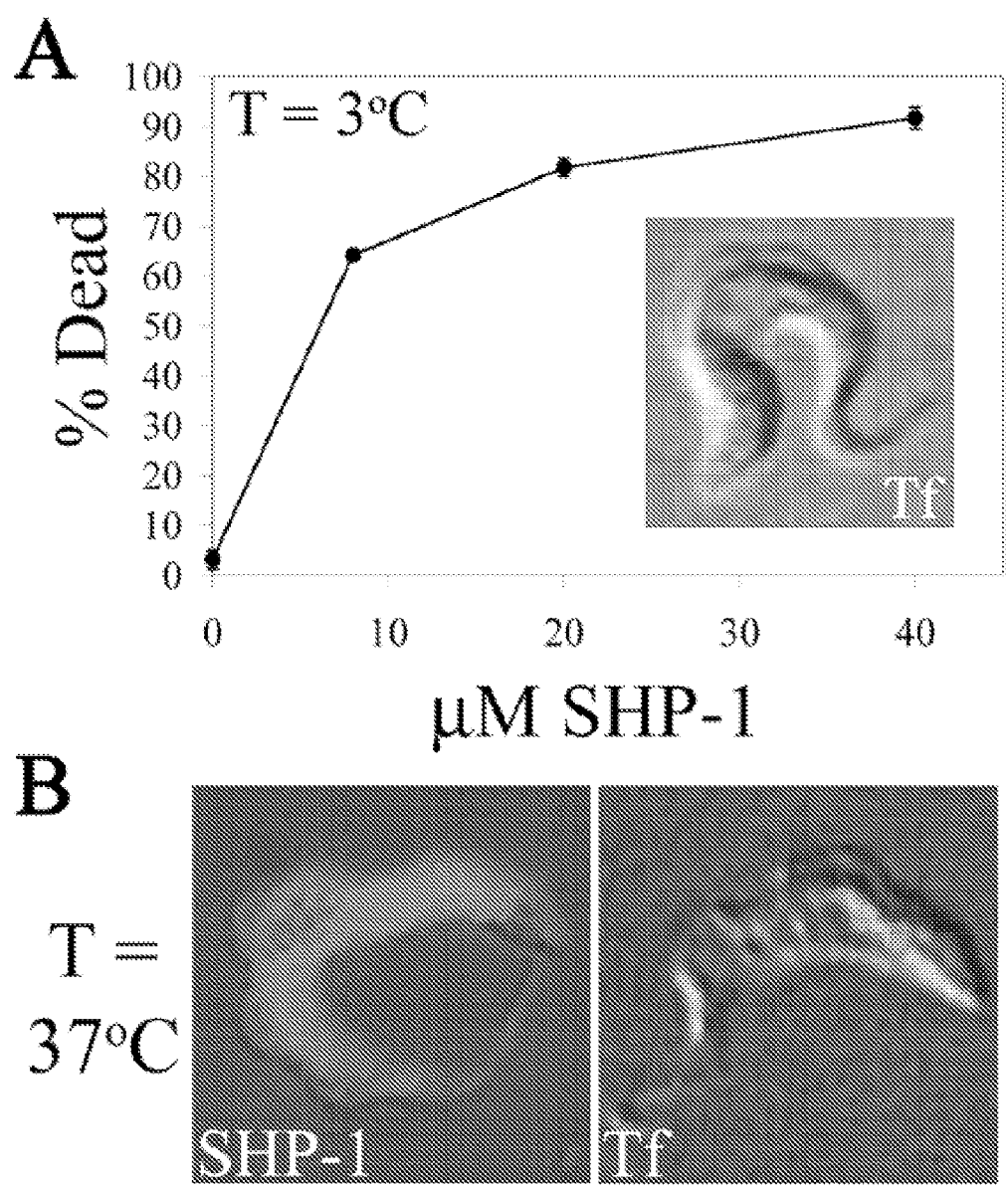
FIG. 10 demonstrates that SHP-1 acts at the surface of bloodstream form (BSF) African trypanosomes.

SHP acts at the surface of BSF trypanosomes. Multiple trypanocidal molecules have been identified which exert their toxic effect after localization within an intracellular vesicle rather than at the cell surface (Hager et al., 1994, *J Cell Biol;* 126(1):155-167; and Delgado et al., 2009, *Cell Death Differ;* 16(3):406-416). Therefore, whether SHP-1 requires internalization by the target trypanosome was addressed. Killing assays were performed with SHP-1 at 3° C., a temperature that halts endocytosis (Hager et al., 1994, *J Cell Biol;* 126(1): 155-167). Robust trypanocidal activity (FIG. 10A) was observed, equivalent to killing assays performed at 37° C., suggesting that SHP-1 does not require cellular uptake to exert its toxic effects. Consistent with these data, Texas Red-labeled SHP-1 uniformly binds the surface of BSF trypanosomes at 37° C. rather than accumulating in intracellular vesicles (FIG. 10B).

Figure 11:
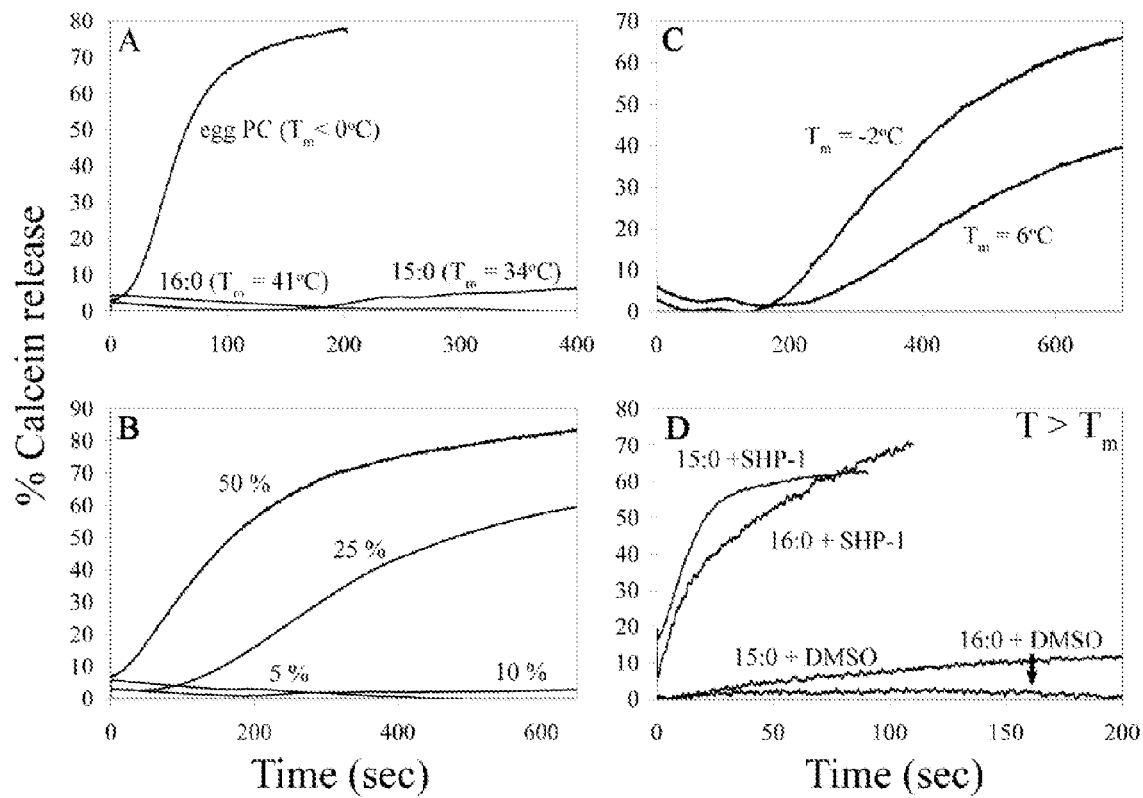
FIG. 11 shows that SHP-1 interacts with membranes exhibiting fluid phase packing.

SHP-1-membrane interaction is dependent on lipid bilayer fluidity. Based upon the physiological necessity of membrane surface flow in BSF *T. brucei*, the role lipid bilayer fluidity plays in dictating sensitivity to SHP-1 was addressed. Liposomes composed of highly fluid compositions such as egg phosphatidylcholine (PC) (Tm<0° C.) (Koynova and Caffrey, 1998, *Biochim Biophys Acta;* 1376(1):91-145), are readily permeabilized by SHP-1 (FIG. 11A). However, homogenous liposomes composed entirely of symmetric PC with saturated chains of 15 to 18 carbon atoms (Tm 34° C. and 55° C. respectively) (Koynova and Caffrey, 1998, *Biochim Biophys Acta;* 1376(1):91-145) are not permeabilized by SHP-1 (FIG. 11A). Fluidizing refractory lipid compositions by incorporating increasing mole percent DMPC (symmetric 14:0, Tm=23.6° C.) led to a DMPC-concentration-dependent increase in susceptibility to SHP-1 (FIG. 11B).

To determine whether SBP-1 has a specific affinity for membrane myristate or susceptibility is due to a general physical, property imparted by the short acyl chain, liposomes composed of PC with different acyl chain moieties and transition temperatures (Tm) were assayed. The presence of an unsaturation in 16- or 18-carbon acyl chains results in a large decrease in bilayer transition temperature relative to their unsaturated counterparts. Liposomes composed of POPC, Tm=−2° C. (25), or SOPC, 18:0-18:1 PC, Tm=6° C. (25), are susceptible to permeabilization by SHP-1 indicating that myristate is not a requirement for membrane interaction (FIG. 11C). The role of membrane fluidity in mediating membrane sensitivity to SHP-1 was further investigated by conducting permeabilization assays with the refractory lipid compositions at temperatures above their Tm. Fluidizing lipid bilayers composed of 1,2-dipentadecanoyl-sn-glycero-3-phosphocholine (symmetric 15:0, Tm=34° C.) or DPPC (symmetric 16:0, Tm=41.3° C.) (Koynova and Caffrey, 1998, *Biochim Biophys Acta;* 1376(1):91-145) by bringing liposomal suspensions above their respective Tm resulted in sensitivity to permeabilization by SHP-1 (FIG. 11D). These data indicate that it is not affinity for a specific bilayer moiety but the general physical property of membrane fluidity that confers susceptibility to SHP-1.

Figure 12:
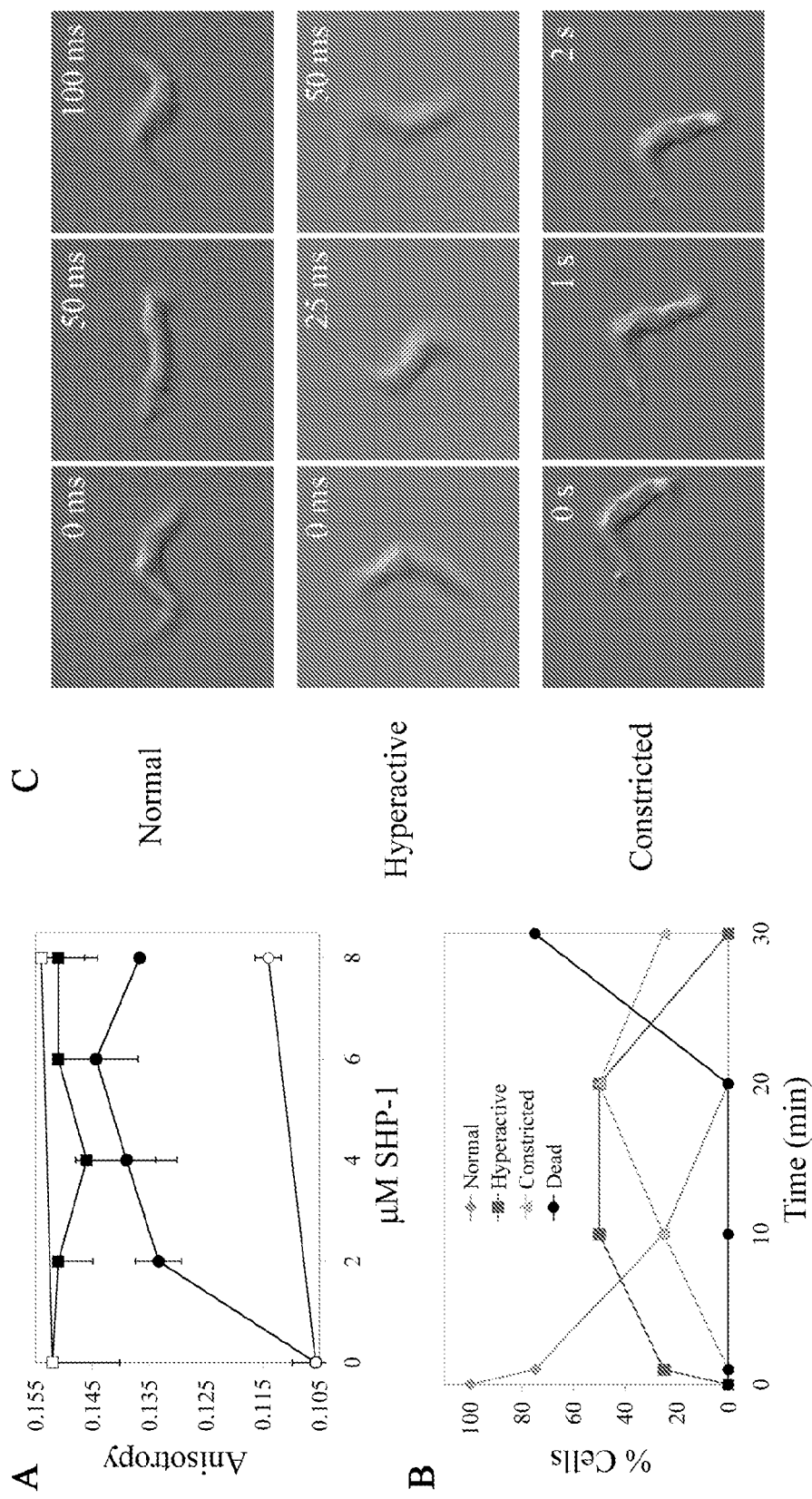
FIG. 12 demonstrates that SHP-1 changes the mechanoelastic properties of bloodstream form (BSF) *T. brucei* membranes and induces dramatic changes in motility.

SHP-1 induces rigidification of BSF trypanosome cell membranes. Based upon the role of lipid bilayer fluidity in SHP-1 membrane interaction and the restriction of liposomal acyl chain motion by *E. coli* LamB signal sequence peptides (Jones and Gierasch, (1994) *Biophys J;* 67(4):1534-1545), the effect SHP-1 has upon the fluidity of BSF *T. brucei* membranes was assayed. The surface membrane probe TMA-DPH, a cationic lipophilic molecule that rapidly partitions into the outer leaflet of the cellular lipid bilayer, was utilized. Addition of SHP-1 increases the rigidity of BSF cell membranes as indicated by an increase in the anisotropy of the surface membrane probe TMA-DPH (FIG. 12A). The difference in membrane composition of PCF trypanosomes is apparent in the higher anisotropic values, i.e. greater rigidity, acquired for PCF cells. Consistent with the lack of SHP-1 binding to PCF cells and data from model liposomes indicating that a high degree of fluidity is required for SHP-1 intercalation, the anisotropy of PCF trypanosomes is unchanged by the addition of peptide. In contrast to BSF cells, PCF trypanosomes are significantly less motile and do not exhibit high turnover rates of surface proteins or endocytic activity.

SHP-1 induces dramatic changes in cell motility. During the course of our investigations on BSF *T. brucei* killing, it readily became apparent that treatment of cells with SHP-1 resulted in motility changes. In order to assess the effect of SHP-1 on the motility of trypanosomes BSF cells were analyzed by DIC video microscopy. Addition of 8 M SHP-1 resulted in a progression of motility changes over 30 min (FIG. 12B). Untreated BSF trypanosomes exhibit a characteristic corkscrew motion (FIG. 12C). Within a minute of SHP-1 addition, a significant fraction of cells exhibit hyperactive motility (FIG. 12C). Hyperactivated cells are still present at 10-20 minutes, however, a portion of cells display highly constricted motion (FIG. 12C). The constricted motility phenotype is increasingly apparent at 20 minutes, with approximately 50% of the cells displaying constriction, the other 50% remaining hyperactivated in their motion. During the time course dead cells are increasingly apparent. This phenomenon is more pronounced at 80 µM SHP-1 with all of the cells exhibiting hyperactivity until slowing down and dying within 10 min.

Discussion

This example demonstrates that a small peptide that rapidly intercalates into the plasma membrane of BSF *T. brucei* and induces cell death. The peptide is highly specific for the developmental form found within a mammalian host. Specificity is mediated at the level of binding, or more likely intercalation into the acyl chain region of the target membrane. Indeed, studies with model membrane systems indicate that the peptide is sensitive to the acyl chain composition of lipid bilayers. In particular the membrane fluidity that is imparted by a given acyl chain composition dictates the ability of this peptide to interact with membranes.

Killing of BSF *T. brucei* has been demonstrated for a variety of bona fide antimicrobial peptides (McGwire et al., 2003, *J Infect Dis;* 188(1):146-152; and Haines et al., 2009, *PLoS Negl Trop Dis;* 3(2):e373), such as the cathelicidins and their derivatives novispirin and ovispirin, as well as unusual candidates such as neuropeptides (Delgado et al., 2009, *Cell Death Differ;* 16(3):406-416). In the case of cathelicidins it has been shown that these peptides permeabilize the plasma membrane and cells assume a rounded and crumpled morphology upon death (McGwire et al., 2003, *J Infect Dis;* 188(1):146-152). At relatively high concentrations of SHP-1, massive disruption of the cellular membrane is observed, however, as revealed by video microscopy, this occurs subsequent to cell death. Treatment with lower concentrations of SHP-1, i.e. 4 µM, results in dead *T. brucei* that exhibit a normal morphology and DIC microscopy indicates that the cellular membrane remains intact. The lack of osmotic swelling suggests that permeabilization of the plasma membrane is not the mechanism of killing. Furthermore, the observed changes in BSF *T. brucei* cell membrane rigidity by SBP-1 suggest a novel mechanism of toxicity.

Bloodstream form African trypanosomes are highly dynamic cells with respect to motility (Rodriguez et al., 2009, *PNAS;* 106(46):19322-19327; and Oberholzer et al., 2010, *PLoS Pathog;* 6(1):e1000739), endocytosis and vesicle trafficking (Engstler et al., 2004, *J Cell Sci;* 117(Pt 7):1105-1115) and lateral flow of surface molecules (Bulow et al., 1988, *Biochem;* 27(7):2384-2388; and Engstler et al., 2007, *Cell;* 131(3):505-515). All of these activities require movement of membrane components such as phospholipids, and in the case of endocytosis and vesicle trafficking, remodeling of the lipid bilayer. Decreasing the physical property of fluidity in the bulk membrane such that these activities are burdened may contribute to a general poisoning of the cell by SBP-1. Alternatively, or in synergy with membrane rigidification, SBP-1 may act through non-specific alterations of integral membrane protein stability/activity (Lee, 2004, *Biochim Biophys Acta;* 1666(1-2):62-87). For example, distortion of the lateral pressure profile, a mechanism that has been attributed to general anesthetics (Cantor, 1998, *Toxicol Lett;* 100-101: 451-458), may lead to increased lateral pressure which in turn may physically inhibit transmembrane channels (Kamaraju and Sukharev, 2008, *Biochem;* 47(40):10540-10550). Additionally, peptides corresponding to the *E. coli* LamB signal peptide have been shown to effect the oligomerization of integral transmembrane proteins (Benach et al., 2003, *J Biol Chem;* 278(6):3628-3638). Such surface activity is consistent with the SHIP-1 site of action being the plasma membrane as suggested by killing assays performed at 3° C. (FIG. 10A) and labeling of the surface of BSF *T. brucei* by Texas-red-SHP-1 (FIG. 10B). In either case, the fluidity of the BSF trypanosome cell membrane appears to not only be modified by the SHP-1, but also specifically targeted.

The studies of this example, with model liposomes, indicate that the fluidity of the target lipid bilayer determines the ability of SHIP-1 to bind and permeabilize membranes. These data are consistent with previous studies showing that modulation of the surface pressure of lipid monolayers dictates the ability of signal peptides to intercalate into the acyl chain region (Briggs et al., 1986, *Science;* 233(4760):206-208). Membranes exhibiting gel phase lipid order are refractory to permeabilization by SHP-1. When these refractory liposomes are brought above their transition temperatures, thus exhibiting liquid crystalline order, they are rendered susceptible to permeabilization by SHP-1. These data indicate that the lateral van der Wants forces dictate the ability of SHP-1 to intercalate into target lipid environments. The immediate labeling of the entire population of BSF *T. brucei* by Texas-red labeled SHP indicates a very rapid rate of bilayer intercalation (FIG. 7C).

The consequences of SHP-1 intercalation into BSF trypanosome membranes are immediately apparent on the cellular level. Cells exhibit hypermotility immediately after introduction of SHP-1 subsequently becoming constricted in their motion before dying. The cause for these changes in motility can only be speculated upon. Spermatozoa are examples of flagellated cells that undergo changes in membrane fluidity concurrent with the onset of hypermotility (Visconti et al., 2002, *J Reprod Immunol;* 53(1-2):133-150). Hyperactivation is associated with efflux of cholesterol and an increase in membrane fluidity. In this regard Tyler et al. have recently demonstrated that *T. brucei* flagellar membranes are enriched in cholesterol and exhibit a higher degree of order than the pellicle of the cell (Tyler et al., 2009, *J Cell Sci;* 122(Pt 6):859-866). It is intriguing to imagine that SHP-1 induces a redistribution of cholesterol from the flagellum to the pellicular fraction of the cell membrane. This would result in an overall increase in cell membrane rigidity coupled with a localized decrease of the flagellar rigidity, and thus alleviation of physical strain against flagellar motors and acceleration of flagellar beating. The observed constricted motility at later time points following treatment with SHP-1 may be the result of metabolic depletion.

Small hydrophobic peptides target a fundamental physiological characteristic of *T. brucei*, namely the fluid physical property of the cell membrane. It is not likely that BSF trypanosomes will quickly develop a strategy to circumvent the cytotoxicity of molecules that alter the mechanoelastic properties of the cell membrane. This example demonstrates that the BSF trypanosome cell membrane is an attractive target for the development of novel therapeutics. See also, Harrington et al., 2010, *J Biol Chem,* 285(37):28659-66 (Epub 2010 Jul. 8).

Example 3

Killing *T. congolense, T. vivax,* and the Metacyclic Forms of *T. brucei*

African trypanosomes are eukaryotic parasites that cause sleeping sickness in humans and a wasting disease known as Nagana in cattle. As shown in the previous examples, a small trypanocidal peptide has been derived from the human trypanosome lytic factor (TLF), a subset of high density lipoproteins that confers immunity to veterinary pathogenic trypanosomes. As described in Examples 1 and 2, the peptide kills both the veterinary pathogen *Trypanosoma brucei brucei* and the human pathogenic subspecies responsible for African sleeping sickness, *T. b. rhodesiense* and T. b. gambiense. Screening of the peptide against a number of eukaryotic pathogens, human cell lines and the procyclic form trypanosome, the developmental stage within the insect vector midgut, indicates that the peptide uniquely targets the developmental stage of trypanosome found within the mammalian host. The lack of toxicity against mammalian cell lines suggests a therapeutic potential for treatment of human and animal trypanosomiasis. This example will test the peptides against the major cattle pathogens T. congolense and T. vivax. Additionally, the activity of the peptide will be tested against metacyclic trypanosomes, the developmental form within the tsetse fly salivary gland and thus the first developmental stage encountered by a potential human or animal host.

Trypanosome lytic factor uniquely contains two trypanolytic proteins, haptoglobin related protein (Hpr) and apolipoprotein L-1 (Shiflett et al., 2005, J Biol Chem; 280 (38):32578-32585). Haptoglobin related protein is unusual in that it is secreted from hepatocytes without cleavage of its hydrophobic N-terminal signal peptide (Hpr-SP) (Smith et al., 1995, Science; 268(5208): 284-286). Previous work established that human Hpr, when purified in a delipidated form, kills bloodstream form T. b. brucei (Shiflett et al., 2005, J Biol Chem; 280(38): 32578-32585). The lack of trypanolytic activity from recombinant Hpr (Vanhollebeke et al. 2006, PNAS; 104(10), 4118-4123) led us to investigate the potential activity of a synthetic 19-amino acid peptide corresponding in sequence to the Hpr-SP. The previous examples have established that Hpr-SP is toxic to all bloodstream form T. brucei and that the specificity of Hpr-SP is mediated by the high presence of myristate, a short 14 carbon, saturated acyl chain, in the cell membrane. The unusually high content of myristate is due to the glycerophosphoinositol-anchoring of the trypanosome's variable surface glycoproteins. The high content of myristate lends the cell membrane a high degree of fluidity that facilitates both the rapid uptake of bound host antibodies and cell surface bound nutrients. The Hpr-SP induces a rigidification of the cell membrane that results in dramatic motility changes and rapid onset of cell death (as shown, for example, in Examples 1 and 2).

In the case on of the T. brucei subspecies, the membrane composition is particularly well characterized; The VSG proteins in bloodstream form trypanosomes are membrane anchored via myristate (Ferguson et al., 1985, J Biol Chem; 260(27):14547-14555), whereas the procyclic forms utilize longer saturated chains, stearate and palmitate (Field et al., 1991, EMBO; 10(10): 2731-2739) which provide increased lateral van der Waals forces and presumably protect the membrane from intercalation of Hpr-SP. Example 2 shows that cells refractory to Hpr-SP killing are not bound by the peptide.

With this example, the cattle pathogens T. congolense and T. vivax will be tested for susceptibility to binding and killing by hydrophobic signal sequence peptides, including, but not limited to, SEQ ID NO:1-20. There are some indications that these species possess different membrane compositions than the T. brucei subspecies. For instance probing the surface with antibodies against surface lectins suggests a less dense VSG coat, and therefore less myristate within the cell membrane. In vitro killing assays will be carried out against T. congolense and T. vivax. Assays will be performed by incubating trypanosomes with various concentrations of peptide in HMI-9 media for two hours at 37° C. Purified human TLF will serve as a positive killing control. Additionally, the binding, or lack thereof, of hydrophobic signal sequence peptides to these cell lines will be determined utilizing Texas-red labeled Hpr-SP and analysis by flow cytometry or fluorescence microscopy.

The metacyclic form of T. brucei resides within the salivary glands of the tstese fly vector. This developmental stage is primed for encountering a potential mammalian host through the bite of the fly. Consistently, the metacyclic form expresses GPI-anchored VSG rather than the procyclic acid repeats characteristic of the developmental stages within the mid- and hind gut of the tsetse fly. Thus, the metacyclic forms will likely be susceptible to killing by Hpr-SP. Metacyclic T. brucei will be collected from tsetse fly salivary glands, washed into PBS supplemented with 30% media and subject to the previously described assays. These assays will indicate the possibility of utilizing hydrophobic signal sequence peptides, such as Hpr-SP, as a molecule capable of preventing initial infection of potential animal hosts from interaction with the trypanosome containing insect vector. The studies of this example will greatly inform our knowledge of the therapeutic potential of Hpr-SP and the membrane physiology of different Trypanosoma sp. and developmental forms.

Example 4

Novel African Trypanocidal Agents

Membrane Rigidifying Peptides

The bloodstream developmental forms of pathogenic African trypanosomes are uniquely susceptible to killing by small hydrophobic peptides. Trypanocidal activity is conferred by peptide hydrophobicity and charge distribution and results from increased rigidity of the plasma membrane. This mechanism reveals a necessary phenotype, high membrane fluidity, unique to these pathogens, and indicates that the plasma membrane and its biosynthetic components are novel targets for the development of pharmaceutical agents.

As shown in the previous examples, both veterinary and human pathogenic bloodstream form (BSF) T. brucei are uniquely susceptible to killing by two small hydrophobic peptides, SHP-1 and SHP-2. This example demonstrates that the specificity of SHP is mediated by a high degree of fluidity in the plasma membrane of BSF cells. These peptides do not bind, and thus do not kill, procyclic (PC) form T. brucei, which has a more rigid plasma membrane, or mammalian cells, nor are they hemolytic at concentrations orders of magnitude higher than necessary to kill BSF T. brucei. See also, Harrington et al., 2010, J Biol Chem; 285(37):28659-66.
Materials and Methods Peptides and Lipids. All peptides were purchased from Bio-Synthesis, Inc. (Lewisville, Tex.). All lipids were purchased from Avanti Polar Lipids (Alabaster, Ala.). These include phosphatidylcholine from egg (8450051) and 1-palmitoyl-2-(6,7-dibromo)stearoyl-sn-glycero-3-phosphocholine (850480) and 1-palmitoyl-2-(9,10-dibromo) stearoyl-sn-glycero-3-phosphocholine (850481).

Trypanosome Killing Assays. Light microscopy based trypanosome killing assays were performed as previously described in detail (Harrington et al., 2010, J Biol Chem; 285(37):28659-66; Widener et al., 2007, PLoS Pathog; 3(9): 1250-61; Shiflett et al., 2007, J Eukaryot Microbiol; 54(1): 18-21; and Hajduk et al., 1989, J Biol Chem; 264(9):5210-7). Metacyclic T. b. brucei TREU 667 were obtained from dissection of the salivary glands of infected tsetse flies. Newly hatched Glossina morsitans morsitans (24-48 hours post eclosion) were fed defibrinated horse blood containing $2 \times 10^6$ $ml^{-1}$ trypanosomes and maintained at 25° C. in 75% relative humidity and fed maintenance blood meals three times per week. Following day 20-30, flies were harvested and salivary glands were dissected out and washed in HMI 9 media containing 10% fetal bovine serum. Metacyclic cells were collected via centrifugation and maintained in HMI 9 media with 10% fetal bovine serum at 37° C. in 5% $CO_2$ until use. Killing assays were conducted with 1×10⁴ cells/ml in HMI 9 media containing 10% fetal bovine serum. *Trypanosoma vivax* and *T. congolense* were grown from stabilites in donor ICR mouse (Harlan, United Kingdom). Parasites were harvested from mice by terminal exsanguination and passage of infected blood through a small anion exchange column. Cells were maintained in HMI 9 with 20% goat serum at 37° C. in 5% $CO_2$ until use. Killing assays were performed with 1×10⁷ cells/ml in HMI 9 media with either 20% goat serum, in the case of *T. vivax* and *T. congolense*, and 10% fetal bovine serum, for *T. b. brucei*. Cells were incubated at 37° C. for 2 hours and dead parasites were scored visually. All were conducted in at least duplicate, and data points are the averages with standard deviations.

Anisotropy Assays. The plasma membrane rigidity of live *T. b. brucei* was determined by measuring the fluorescence depolarization of diphenyl-1,3,5-hexatriene p-toluenesulfonate (DPH) or 1-(4-trimethylammoniumphenyl)-6-diphenyl-1,3,5-hexatriene p-toluenesulfonate (TMA-DPH; Invitrogen T204). Cells were washed 3 times with and resuspended in PBS at a density of 3×10⁶ cells/ml. The anisotropic probes were added to a final concentration of 0.5 M and allowed to intercalate into the cell membrane for one hour in the dark. Anisotropic values were acquired via the software function of a PerkinElmer Life Sciences LS55 spectrofluorometer. Samples were excited at 358 nm, and emission was read at 430 nm, both with 10-nm slit widths. Temperature was maintained at 37° C. by means of the PerkinElmer LS55 Biokinetics accessory. Data were corrected for light scattering with an unlabeled sample of cells, and anisotropy was calculated according to the equation $r=(I_{VV}-GI_{VH})/(I_{VV}+2GI_{VH})$, where r is the anisotropy value, $I_{VV}$ is the emission intensity acquired with the excitation- and emission-polarizing filters set vertically, G is the instrument correction factor, and $I_{VH}$ is the emission intensity acquired with the excitation-polarizing filter set vertically and the emission-polarizing filter set horizontally. All assays were conducted at 37° C. Data points shown are the average of triplicate measurements with standard deviations.

Trypanosome motility. All images and videos were acquired with an Axio Observer Z1 equipped with an AxioCam MRm controlled by AxioVision 4.6 software. Videos were acquired with live cells at a density of 1×10⁷ cells/ml in HMI 9 media with 10% fetal bovine serum, incubated with 40 M SHP-1 at 37° C. Videos were recorded at magnification 63× with 50-ms acquisition times. The motility of BSF trypanosomes was scored visually from video playback of trypanosomes scanned throughout 10 μl aliquots. Data is shown as the average of triplicate trials with standard deviations.

Parallax Analysis. The hydrocarbon penetration depth of tryptophans spaced throughout synthetic peptides corresponding to SHP-1 or SHP-3 (Table 1) was determined by parallax analysis with brominated phosphatidylcholine liposomes. Large unilamellar liposomes composed of egg phosphatidylcholine and 10 mol % 1-palmitoyl-2-(6,7-dibromo) stearoyl-sn-glycero-3-phosphocholine (shallow quencher) or 1-palmitoyl-2-(9,10-dibromo)stearoyl-sn-glycero-3-phosphocholine (deep quencher) were constructed by hydration of a thin dry lipid film with phosphate buffered saline. Resulting multilamellar liposomes were made unilameller via extrusion through polycarbonate filters with 0.1 μm pores. Peptides (500 nM) were incubated with 200 g/ml liposomes in phosphate buffered saline at 37° C. for 22 hours (h). Tryptophan fluorescence at 357 nm was measured from at least triplicate trials in the PerkinElmer Life Sciences LS55 spectrofluorometer and an excitation wavelength of 280 nm for SHP-1 and 290 nm for SHP-2, 10 nm excitation and 9 nm emission slit widths. The distance of tryptophans from the bilayer center (ZCF) is calculated from the equation: $Z_{CF}=L_{C1}+[-ln(F_1/F_2)/\pi C-L_{21}^{2}]/2L_{21}$ (Chattopadhyay and London, 1987, *Biochemistry;* 26(1):39-45); where $L_{C1}$ is the distance from the center of the bilayer to the shallow quencher, in this case 10.8 Å for 6,7-dibromo-PC (McIntosh and Holloway, 1987, *Biochemistry;* 26(6):1783-8), $F_1$ is the intensity of tryptophan in the presence of the shallow quencher and $F_2$ is the tryptophan intensity in the presence of the deep quencher, C is the mole fraction of quencher divided by the area of individual phospholipid (70 Å2), and $L_{21}$ is the difference in the depth of the two quenchers (2.7 Å) (McIntosh and Holloway, 1987, *Biochemistry;* 26(6):1783-8). The hydrocarbon insertion depth of tryptophans is then given by one half the bilayer thickness, 29 Å (McIntosh and Holloway, 1987, *Biochemistry;* 26(6): 1783-8), minus $Z_{CF}$.

Flow Cytometry. Peptide binding to BSF *T. b. brucei* was monitored by flow cytometry. Binding assays were performed with 3×10⁶ cells/ml in HMI 9 plus 10% fetal bovine serum at 25° C. FITC-labeled SHP-1 or SHP-3 was added to a final concentration of 8 μM and 50,000 cells were immediately counted on a CyAn ADP flow cytometer (Dako). Data were analyzed with FlowJo software (TreeStar Inc.).

Calcein Release Assays. Membrane permeabilization assays were conducted as described in detail previously (Harrington et al., 2010, *J Biol Chem;* 285(37):28659-66; and Harrington et al., 2009, *J Biol Chem;* 284(20):13505-12). Unilamellar liposomes were constructed as described above but with 30 mM calcein in 10 mM Hepes as the hydration buffer. Untrapped dye was removed by gel (Sephacryl S-300 HR, GE Healthcare). Liposomes were diluted 1:1000 into phosphate buffered saline, and calcein fluorescence was monitored at 513 nm when excited at 484 nm. The percent calcein release was calculated relative to the 100% fluorescence intensity, achieved by the addition of 0.01% Triton X-100.

Discussion

Figure 13:
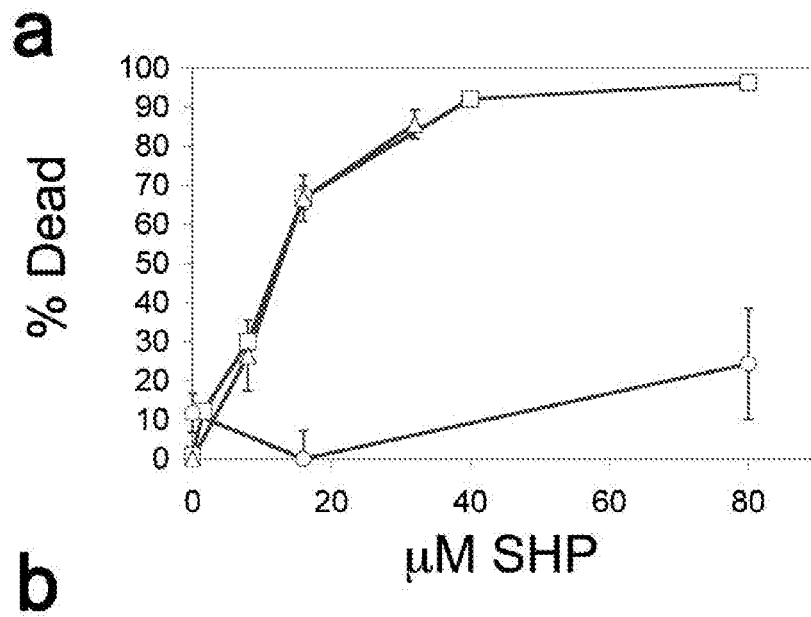
FIG. 13 demonstrates small hydrophobic peptide mediated killing of African trypanosomes.
Figure 13:
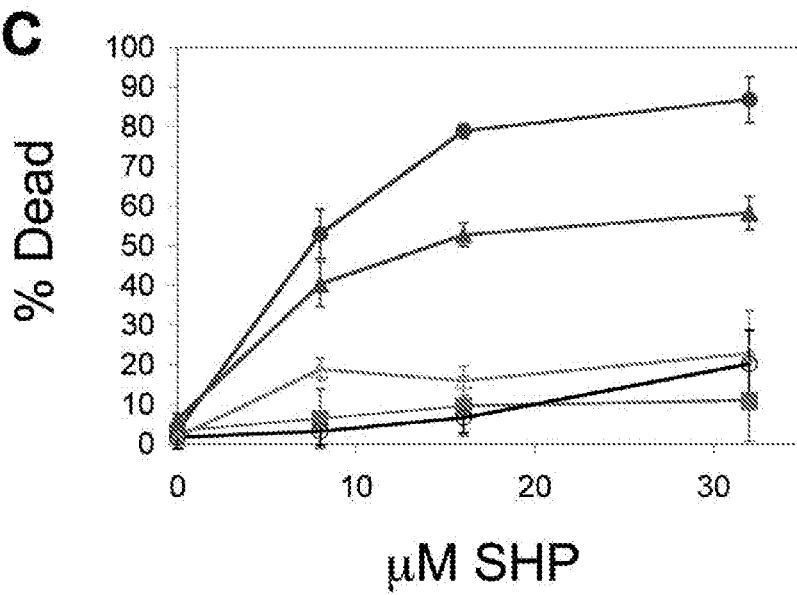

An immediately apparent difference between the plasma membranes of BSF and PC African trypanosomes is the lack of a dense coat of VSG in the insect stage cells. Metacyclic stage cells, which do express a VSG coat, were tested for susceptibility to SHP-1 and found no killing activity (FIG. 13A). Next this example determined whether other African trypanosomes are sensitive to SHP. Bloodstream developmental forms of both *T. vivax* and *T. congolense* are susceptible to killing by SHP-1 at concentrations similar to BSF *T. brucei* (FIG. 13A), indicating that membrane fluidity is a characteristic of both human and veterinary pathogenic African trypanosomes.

Figure 16:
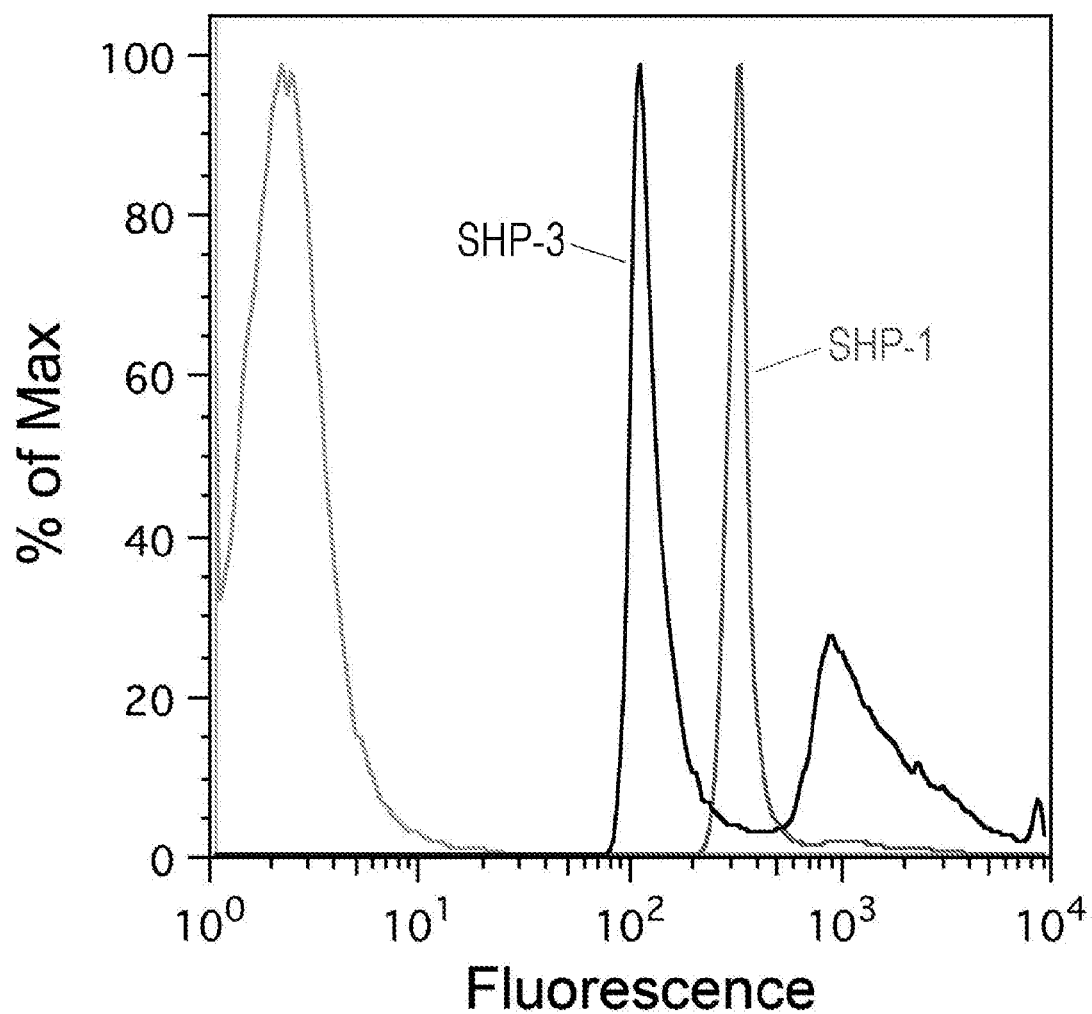
FIG. 16 shows SHP binding to BSF *T. b. brucei*. FITC-labeled SHP-1 and SHP-3 were assayed for binding to BSF *T. b. brucei* via flow cytometry. Trypanosomes were adjusted to $3\times10^6$ cells/ml in HMI 9 media with 10% fetal bovine serum, 8 μM FITC-SHP-1 or FITC-SHP-3 was added and 50,000 cells were immediately counted.

As shown in the previous examples, trypanocidal SHP are derived from apolipoproteins and exhibit the characteristics of secretory signal peptides, i.e. size (18-22 amino acids), a central hydrophobic region and a C-terminal putative signal peptidase cleavage site defined by specific amino acid patterns. See also Harrington et al., 2010, *J Biol Chem;* 285(37): 28659-66. Although these peptides share physical features, their primary structures are entirely different (FIG. 13B). A third, distinct SHP (SHP-3) was tested for trypanocidal activity, also derived from an apolipoprotein (Axler et al., 2008, *FEBS Lett;* 582(5):826-8) and possessing similar features as SHP-1 and SHP-2 (FIG. 13C). Despite possessing the same general physical characteristics and binding to BSF *T. brucei* (FIG. 16), no killing was seen against BSF *T. brucei* (FIG. 13C). Comparison of the three sequences revealed that an arginine at position −5 relative to the C-terminus is common to trypanocidal SHP-1 and SHP-2, but is absent in SHP-3 (FIG. 13B). Substitution of an arginine for the leucine in this position of SHP-3 (SHP-3ΔR, FIG. 13B) confers trypanocidal activity (FIG. 13C). Replacement of the leucine with glutamate in SHP-3 (SHP-3ΔE, FIG. 13B) does not (FIG. 13C). Trypanolytic SHP-2 has a positive charge at both the N- and C-terminus, SHP-1 has only a single positive charge at the C-terminus; thus whether charge location is important was tested by swapping the C-terminal asparagine with the N-terminal aspartate of SHP-1 (SHP-1-swap, FIG. 13B). Rearranging the residues resulted in a loss of trypanocidal activity (FIG. 13C).

Figure 14:
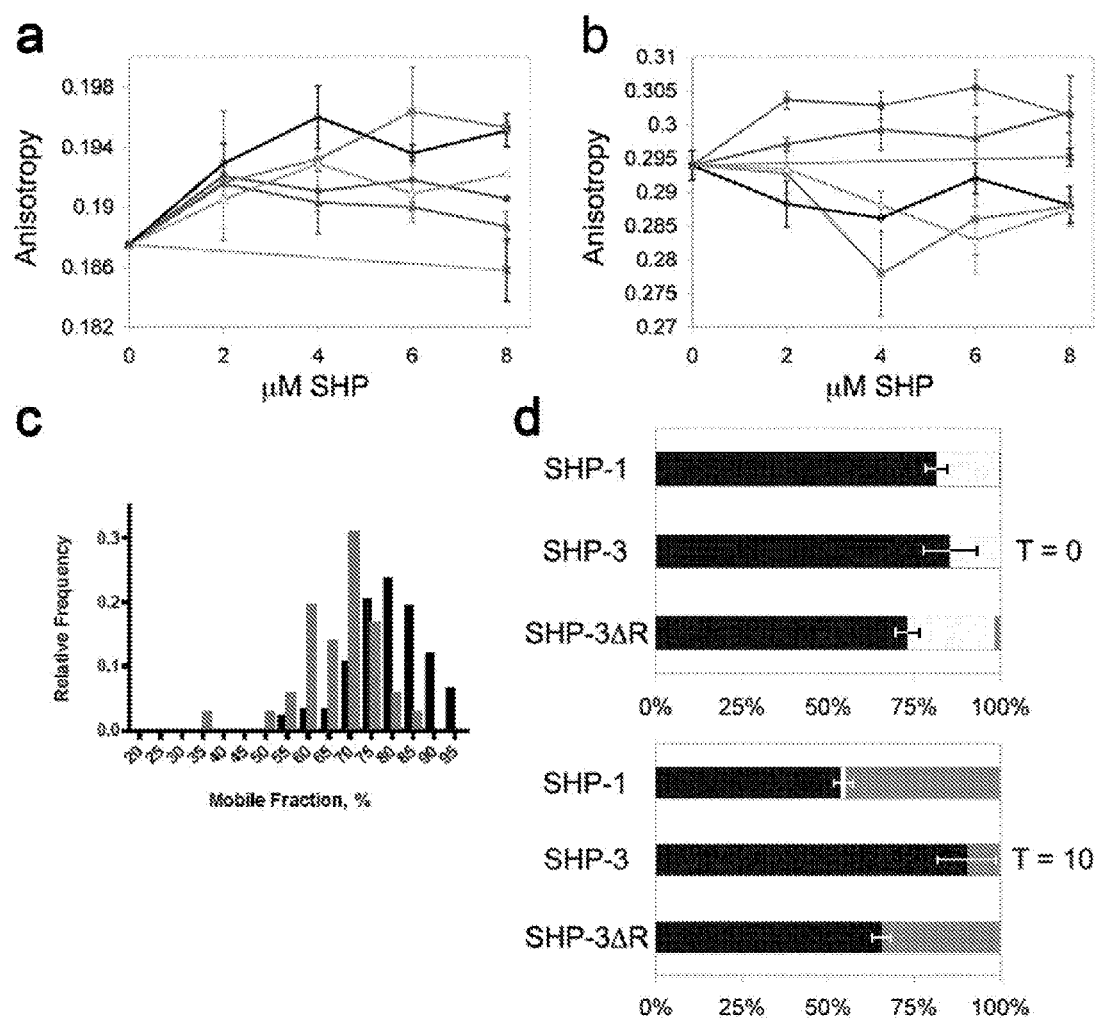
FIG. 14 presents membrane rigidity changes and physiological consequences of SHP. The rigidity of the interior (FIG. 14A) or interfacial (FIG. 14B) region of the plasma membrane of BSF *T. b. brucei* treated with increasing concentrations of SHP-1 (closed circles), SHP-3 (closed squares), SHP-3ΔR (closed triangles), SHP-3ΔE (open triangles), SHP-1swap (open circles) or solvent alone (DMSO) (X) was determined by measuring the fluorescence depolarization of DPH or TMA-DPH respectively.

As shown in the previous examples, trypanocidal SHP act at the plasma membrane but do not induce osmotic swelling or bursting (see also, Harrington et al., 2010, *J Biol Chem;* 285(37):28659-66), suggesting that any effect upon the BSF trypanosome must not result in a loss of plasma membrane integrity. This example investigated the rigidity of BSF *T. brucei* membranes, a property that can change without loss of membrane integrity, utilizing two anisotropic probes, diphenylhexatriene (DPH) that reports on the interior of the acyl chain region, and trimethylammonium-diphenylhexatriene (TMA-DPH) that is anchored at the membrane interface. Addition of either trypanocidal or non-trypanocidal SHP to BSF *T. brucei* results in increased rigidity of the interior region of the plasma membrane (FIG. 14A). However only the trypanocidal SHP-1, SHP-3 and SHP-3ΔR, increased the rigidity of the interfacial region of the plasma membrane (FIG. 14B). These data indicate that rigidification of the interfacial region is necessary for SHP killing of BSF *T. brucei*. The requirement for a C-terminal charge may indicate that ion pairing with the phospholipid headgroups contributes to an increase in interfacial rigidity and thus cell death.

Treatment of BSF African trypanosomes with SHP results in multiple physiological alterations. Rigidification of the plasma membrane by SHP-1 has a direct effect, decreasing the fraction of VSG exhibiting lateral mobility (FIG. 14C). Another physiological consequence, that may or may not be related to membrane rigidification, is SHP-induced changes in cell motility. As shown in Example 2, SHP-1 causes an initial hyperactivation followed by constricted motility and cell death (see also Harrington et al., 2010, *J Biol Chem;* 285(37):28659-66). Non-trypanocidal SHP-3 does cause initial hyperactivation of BSF *T. b. brucei*, however subsequent constriction of motility does not occur (FIG. 14D). Trypanocidal SHP including the SHP-3 variant, SHP-3ΔR, induce both initial hyperactivation and subsequent constriction (FIG. 14D). Constricted motility may result in reduced hydrodynamic forces acting upon surface proteins. Therefore trypanocidal SHP may not only directly kill BSF African trypanosomes, but may also render them more susceptible to immune killing by delaying the clearance of surface bound host defense molecules (Engstler et al., 2007, *Cell;* 131(3):505-15).

In order to understand why trypanocidal and non-trypanocidal SHP have differential effects on the BSF plasma membrane, this example determined the orientation of SHP-1 and SHP-3 in lipid bilayers by parallax analysis (Chattopadhyay and London, 1987, *Biochemistry;* 26(1):39-45). Tryptophans were substituted at positions 1, 8 and 18 (N- to C-terminus, native tryptophan located at position 12) (Table 1) in SHP-1 and positions 1, 13 and 20 in SHP-3 (N- to C-terminus, native tryptophan located at position 5) (Table 1). These placements were chosen, and native tryptophan residues were replaced with glycine, in order to retain the hydrophobic profile of the original peptides.

TABLE 1

Sequences and Quenching Data of SHP Tryptophan Variants.

| Peptide | Sequence (N- to C- terminus)[1] | SEQ ID No: | $F_1/F_2$ ± S.D.[2] |
|---------|-------------------------------|------------|---------------------|
| SHP-1ΔW1 | WDLGAVISLLLGGRQLFA | 15 | 0.8897 ± 0.1112 |
| SHP-1ΔW8 | SDLGAVIWLLLGGRQLFA | 16 | 0.9767 ± 0.0717 |
| SHP-1 | SDLGAVISLLLWGRQLFA | 2 | 0.9676 ± 0.0560 |
| SHP-1ΔW18 | SDLGAVISLLLGGRQLFW | 17 | 0.9285 ± 0.1557 |
| SHP-3ΔW1 | WHQIGAALLYFYGIILNSIY | 18 | N.A. |
| SHP-3 | FHQIWAALLYFYGIILNSIY | 11 | 0.9202 ± 0.1260 |
| SHP-3ΔW13 | FHQIGAALLYFYWIILNSIY | 19 | 0.9912 ± 0.0787 |
| SHP-3ΔW20 | FHQIGAALLYFYGIILNSIW | 20 | 1.1620 ± 0.3194 |

[1]Peptide sequences illustrate the different positions of tryptophan substitutions (bold).
[2]Quenching data is presented as the ratio of tryptophan fluorescence intensity in the presence of the shallow, $F_1$, and deep, $F_2$, quencher and the standard deviations (S.D.).

Figure 15:
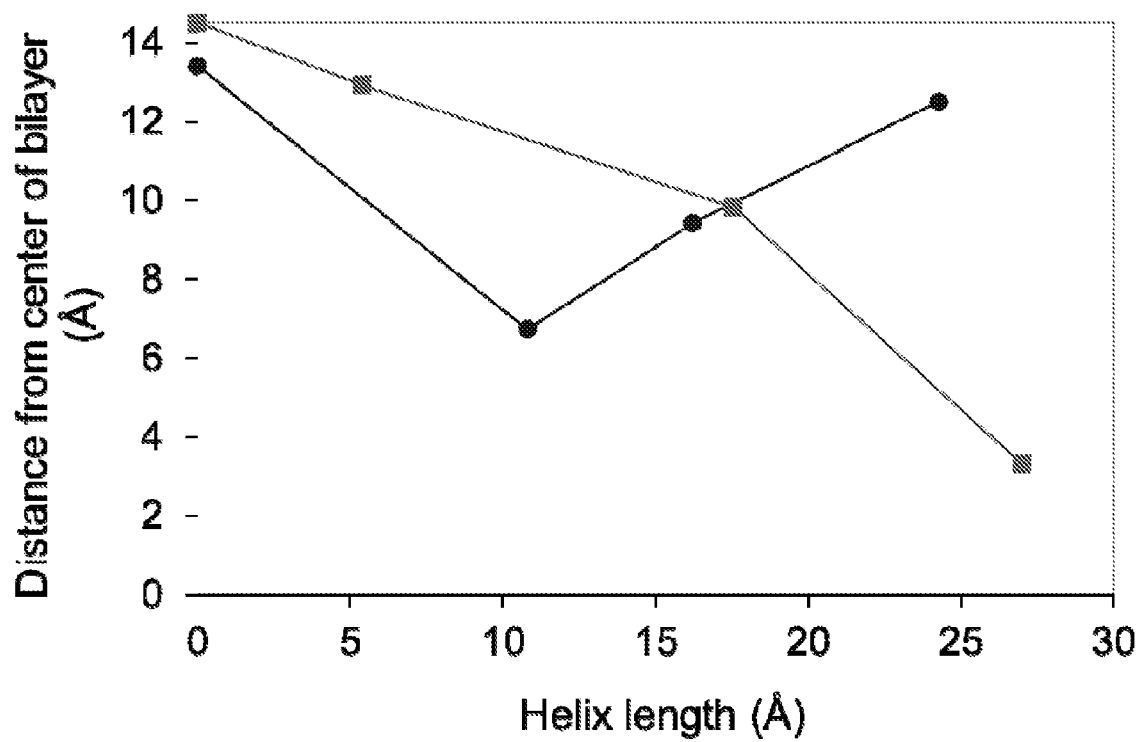
FIG. 15 demonstrates orientation of trypanocidal and non-trypanocidal SHP in lipid bilayers. The depth of tryptophan penetration into the hydrocarbon region of model liposomes was determined via parallax analysis. Assuming a hydrocarbon bilayer thickness of 29 Å, and utilizing depth values from tryptophans substituted along the entire peptides, SHP-1 (circles) and SHP-3 (squares) are illustrated in the context of a helical peptide embedded in the outer leaflet of a phospholipid bilayer.
Figure 17:
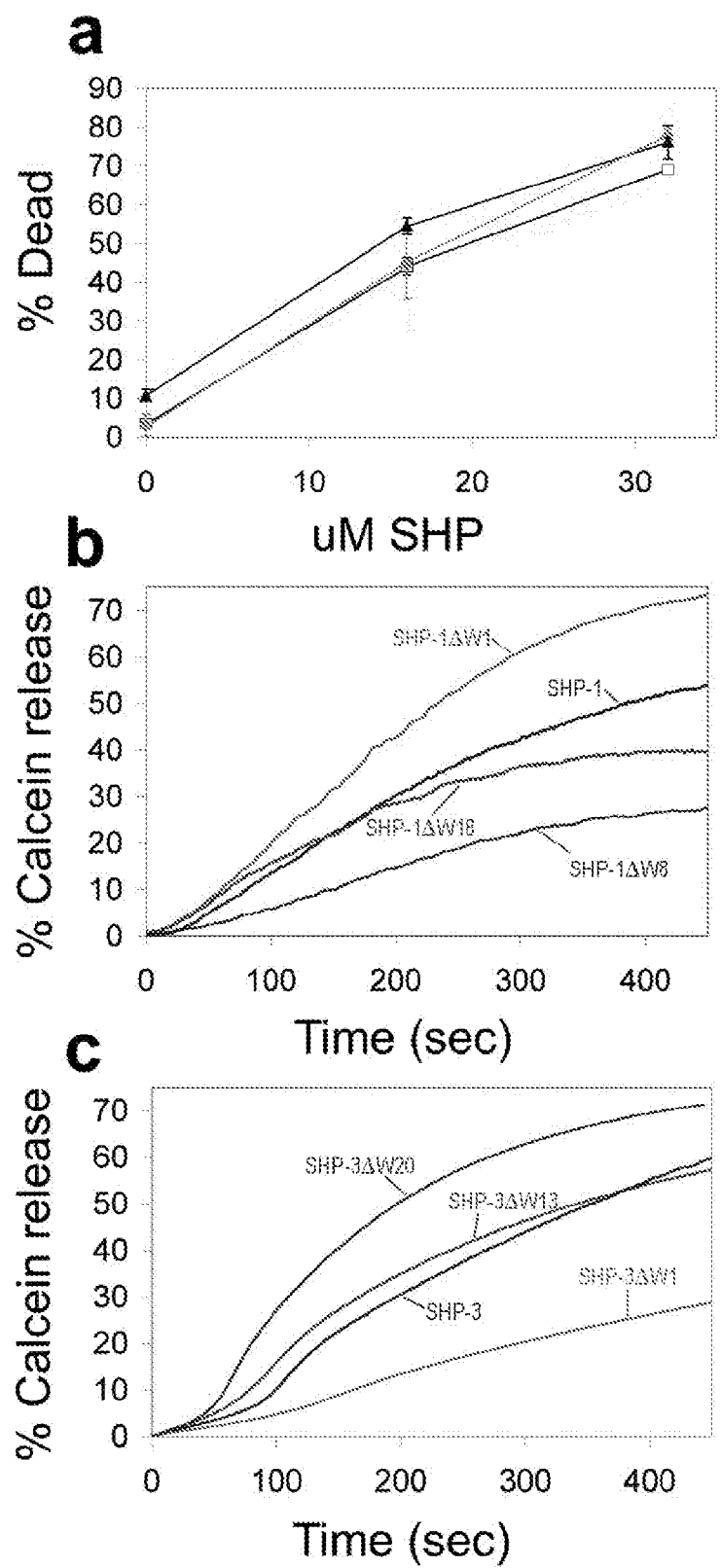
FIG. 17 shows trypanosome killing and membrane interaction with SHP tryptophan variants.

All of the substituted SHP-1 peptides show equivalent killing activity as well as membrane interaction (FIGS. 17A and 17B). The insertion depth of SHP tryptophans was determined by measuring the quenching efficiency of egg phosphatidylcholine liposomes containing 10 mol % brominated phospholipid. Ratiometric analysis of the quenching efficiency of bromines located at the 6,7 position and 9,10 positions of the acyl chains indicates that SHP-1 does not penetrate deeply into the hydrocarbon region and adopts a shallow U-shaped conformation (FIG. 15, Table 1). The two terminal tryptophans, positions 1 and 18, are located approximately 1.1 and 2.0 Å from the membrane interface respectively. The internal tryptophans at positions 8 and 12 are located approximately 7.8 and 5.1 Å from the interface respectively. Therefore, rather than aligning with the phospholipid acyl chains, SHP-1 inserts into the exterior leaflet parallel to the plane of the bilayer and proximal to the interface with the aqueous environment. These data are consistent with what has been observed for other signal peptides (Jones and Gierasch, 1994, *Biophys J;* 1994. 67(4):1534-45; and Voglino et al., 1999, *Biochemistry;* 38(23):7509-16). Non-trypanocidal SHP-3 and the tryptophan variants also exhibit membrane interaction with model liposomes (FIG. 17C). Parallax analysis of SHP-3 indicates deeper penetration into the hydrocarbon chains and a tilted orientation (FIG. 15). The N-terminal tryptophan was inefficiently quenched, suggesting that it does not intercalate into the hydrocarbon region. The native tryptophan, position 5, inserts to approximately 1.6 Å below the interface, while the tryptophan at position 13 is located approximately 4.7 Å deep and the C-terminal tryptophan penetrates most deeply, to approximately 11.2 Å. This orientation precludes interaction of the C-terminus with the lipid headgroups. These data again suggest a role for the positively charged C-terminus in mediating the interfacial rigidity increase of the outer leaflet of the plasma membrane.

African trypanosomes present an attractive target for membrane rigidifying peptides. The BSF cells exhibit extremely high rates of endocytosis and recently it has been reported that nanobodies against VSG that block endocytosis are highly efficient trypanolytic agents (Stijlemans et al., 2011, *PLoS Pathog;* 7(6):e1002072). Surface associated cargo, such as Ig-bound VSG are laterally sorted in the membrane, potentially over the entire length of the cell (Engstler et al., 2007, *Cell;* 131(3):505-15). Membrane rigidification may contribute to cell death by hindering these activities. A fluid membrane may also facilitate the diffusion of small molecule nutrients into the BSF cell. Finally, it has been shown that increasing the rigidity of trypanosome membranes results in a redistribution of proteins normally localized to the flagellar membrane (Tyler et al., 2009, *J Cell Sci;* 122(Pt 6):859-66). Therefore trypanolytic SHP may have pleiotropic effects, interfering with any number of these physiological processes. The specificity of SHP for BSF African trypanosomes reveals a phenotype that may be taken advantage of for the development of pharmaceutical agents. Drugs that target the fluidity of the plasma membrane may offer a means of circumventing the rapid onset of resistance exhibited by these pathogens. Compensating for a phenotype that is the result of a system of gene products would require multiple viable mutations rather than a single mutation within a targeted enzyme or transporter. Additionally the peptides described herein represent a tool to investigate the molecular basis of membrane fluidity.

Example 5

Efficacy of Small Hydrophobic Peptides (SHP) Against African Trypanosome Infection in Mice Peptides of the present invention may be tested in animal models, including, but not limited to, mouse model systems, for anti-trypanosomal activity.

Injection of parasites into animals. Mice will be injected with a defined number of *Trypanosoma brucei brucei* maintained as frozen stocks in liquid nitrogen (0.1-0.2 mL of infected animal blood with DMSO (final concentration 7.5%)). Stocks will be thawed at 37° C., and diluted with an equal volume of sterile saline containing 1% glucose. Mice will be infected by peritoneal injection of parasites. Animals will be swabbed with 70% ethanol on the abdomen prior to injection. Small gauge needles (for example, 26 g) will be used. Animals will be securely held and the hypodermic needle slowly inserted approximately 0.5 cm through the skin into the abdomen at a 60° angle. Parasites will be injected slowly into the abdomen and the needle slowly withdrawn. Following injection, animals will be released into a clean cage and monitored for abnormal activity. The site of injection will be examined five minutes post injection for swelling, bleeding, or other abnormal signs.

Administration of SHP. SHP will be administered by intraperitoneal injection as described above. Peptide will be diluted from a 20 mM stock in DMSO into sterile phosphate buffered saline. Several dosages encompassing a range of 15-60 mg/kg will be administered daily. Alternatively peptide will be administered via oral corn oil gavage.

Monitoring of parasite numbers in infected animals. Numbers of *T. b. brucei* will be monitored daily by phase contrast microscopy of blood samples. This procedure causes only slight and momentary pain to the animal. Tails will be first treated with 2% lidocaine as an analgesic. A drop of blood will be obtained by clipping the extreme end of the mouse tail. 10-20 µl of blood will be milked from the tail vein directly onto a microscope slide for examination. Snipped tails will be treated with liquid bandage to seal the wound and animals will be observed for wound closure. Infections will be monitored for 2-7 days. Parasitemias will be monitored daily and animals will be observed for appearance and behavior. Animals exhibiting signs of stress, ruffled coat, slow or erratic movement will be euthanized immediately. Under no circumstances will animals be allowed to suffer from parasite infection.

Pre-toxicity screens in non infected mice using up to 100 mg/kg may also be undertaken.

Further, guidelines of the World Health Organization (WHO) parasite drug discovery initiative may be followed for the identification and development of new drug candidates (reviewed, for example, by Nwaka and Hudson, 2006, *Nat Rev Drug Discov;* 5:941-95, Nwaka and Ridley, 2003, *Nat Rev Drug Discov;* 2:919-928, and Nwaka et al., 2009, *PLoS Negl Trop Dis;* 3(8):e440).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Sequence Listing Free Text

SEQ ID NO:1 N-terminal amino acid residues 1-19 of the human haptoglobulin-related protein
SEQ ID NO:2 N-terminal amino acid residues 2-19 of the human haptoglobulin-related protein (SHP-1)
SEQ ID NO:3 N-terminal amino acid residues 1-22 of the human paraoxonase-1 protein
SEQ ID NO:4 N-terminal al amino acid residues 2-22 of the human paraoxonase-1 protein (SHP-2)
SEQ ID NO:5 N-terminal amino acid residues 1-22 of the human apolipoprotein M (Apo M)
SEQ ID NO:6 N-terminal amino acid residues 2-22 of the human apolipoprotein M (Apo M)
SEQ ID NO:7 Derivative of SHP-1 having a single leucine deletion
SEQ ID NO:8 Derivative of SHP-1 with deletion of C-terminal leucine triplicate
SEQ ID NO:9 Derivative of SHP-1 with a deletion of the N-terminal leucine-glycine-alanine residues SEQ ID NO:10 Non-specific, hydrophilic peptide predicted from the N-terminus of the alternatively edited protein-1 from mitochondria of *T. b. brucei*

SEQ ID NO:11 Amino acid sequence of small hyrophobic peptide 3 (SHP-3)

SEQ ID NO:12 Derivative of SHP-3 having a leucine to arginine substitution at position −5

SEQ ID NO:13 Derivative of SHP-3 having a leucine to glutamic acid substitution at position −5

SEQ ID NO:14 Derivative of SHP-1 having an aspartic acid to arginine substitution at position 2 and an arginine to aspartic acid substitution at position −5

SEQ ID NO:15 Derivative of SHP-1 having a tryptophan to glycine substitution at position 1

SEQ ID NO:16 Derivative of SHP-1 having a tryptophan to glycine substitution at position 8

SEQ ID NO:17 Derivative of SHP-1 having a tryptophan to glycine substitution at position 18

SEQ ID NO:18 Derivative of SHP-3 having a tryptophan to glycine substitution at position 1

SEQ ID NO:19 Derivative of SHP-3 having a tryptophan to glycine substitution at position 13

SEQ ID NO:20 Derivative of SHP-3 having a tryptophan to glycine substitution at position 20

What is claimed is:

1. A method of inducing rigidification of the plasma membrane of a bloodstream form of a kinetoplastid protozoan of the genus *Trypanosoma*, the method comprising contacting the protozoan with an isolated hydrophobic signal sequence peptide, wherein the isolated hydrophobic signal sequence peptide consists of 17 to 25 amino acid residues of an uncleaved, hydrophobic N-terminal signal sequence, wherein the isolated hydrophobic signal sequence peptide contains a positively charged amino acid at position minus five relative to the C-terminus of the hydrophobic signal sequence peptide, and wherein the hydrophobic signal sequence peptide comprises at least nine consecutive amino acid residues of MSDLGAVISLLLWGRQLFA, SEQ ID NO:1 or a derivative of SEQ ID NO:1, wherein the derivative of SEQ ID NO:1 has up to four hydrophobic amino acid residues of SEQ ID NO:1 exchanged for another hydrophobic amino acid, and/or one positively charged amino acid residues of SEQ ID NO:1 exchanged for another positively charged amino acid.

2. The method of claim 1, wherein the hydrophobic signal sequence peptide is soluble in ethanol or dimethyl sulfoxide (DMSO).

3. A method of inducing rigidification of the plasma membrane of a bloodstream form of a kinetoplastid protozoan of the genus *Trypanosoma*, the method comprising contacting the protozoan with an isolated hydrophobic signal sequence peptide, wherein the isolated hydrophobic signal sequence peptide consists of 17 to 25 amino acid residues of an uncleaved, hydrophobic N-terminal signal sequence, wherein the isolated hydrophobic signal sequence peptide contains a positively charged amino acid at position minus five relative to the C-terminus of the hydrophobic signal sequence peptide, and wherein the hydrophobic signal sequence peptide comprises at least nine consecutive amino acid residues of SEQ ID NO:1, SEQ ID NO:2, SEQ ID NO:7, SEQ ID NO:15, SEQ ID NO:16 or SEQ ID NO:17.

4. The method of claim 1, wherein the trypanosome is selected from the group consisting of *Trypanosoma brucei brucei, T. b. gambiense*, and *T. b. rhodesiense, T. congolense*, and *T. vivax*.

5. The method of claim 1, wherein the hydrophobic signal sequence peptide is provided as a composition further comprising liposome, emulsion, or micelle.

6. The method of claim 1, wherein the hydrophobic signal sequence peptide is provided as a composition further comprising an RNA aptamer that binds to a structurally conserved region of a trypanosome variant surface glycoprotein (VSG).

7. The method of claim 1, wherein the hydrophobic signal sequence peptide is provided as a pyrogen-free composition.

8. The method of claim 1, wherein the plasma membrane rigidification results in killing, inhibition of growth, inhibition of reproduction, plasma membrane degradation, and/or constricted cell motility of the bloodstream form of a kinetoplastid protozoan of the genus *Trypanosoma*.

9. The method of claim 1 wherein contacting the protozoan with a hydrophobic signal sequence peptide comprises in vitro, ex vivo, or in vivo contact.

10. The method of claim 9 comprising in vivo contact within the body of a mammalian subject.

11. A method of inducing rigidification of the plasma membrane of a bloodstream form of a kinetoplastid protozoan of the genus *Trypanosoma*, the method comprising contacting the protozoan with an isolated hydrophobic signal sequence peptide, wherein the isolated hydrophobic signal sequence peptide is selected from the group consisting of SEQ ID NO:1, SEQ ID NO:2, SEQ ID NO:7, SEQ ID NO:15, SEQ ID NO:16 and SEQ ID NO:17.

12. A method of inducing rigidification of the plasma membrane of a bloodstream form of a kinetoplastid protozoan of the genus *Trypanosoma*, the method comprising contacting the protozoan with an isolated trypanocidal peptide of 12 to 25 amino acid residues in length, wherein the isolated trypanocidal peptide comprises at least nine consecutive amino acid residues of MSDLGAVISLLLWGRQLFA, SEQ ID NO:1 or a derivative of SEQ ID NO:1, wherein the derivative of SEQ ID NO:1 has up to four hydrophobic amino acid residues of SEQ ID NO:1 exchanged for another hydrophobic amino acid, and/or one positively charged amino acid residues of SEQ ID NO:1 exchanged for another positively charged amino acid.

13. The method of claim 3, wherein the plasma membrane rigidification results in killing, inhibition of growth, inhibition of reproduction, plasma membrane degradation, and/or constricted cell motility of the bloodstream form of a kinetoplastid protozoan of the genus *Trypanosoma*.

14. The method of claim 3, wherein the trypanosome is selected from the group consisting of *Trypanosoma brucei brucei, T. b. gambiense*, and *T. b. rhodesiense, T. congolense*, and *T. vivax*.

15. The method of claim 3, wherein the hydrophobic signal sequence peptide is provided as a composition further comprising liposome, emulsion, or micelle.

16. The method of claim 3, wherein the hydrophobic signal sequence peptide is provided as a composition further comprising an RNA aptamer that binds to a structurally conserved region of a trypanosome variant surface glycoprotein (VSG).

17. The method of claim 3, wherein the hydrophobic signal sequence peptide is soluble in ethanol or dimethyl sulfoxide (DMSO).

18. The method of claim 3, wherein the hydrophobic signal sequence peptide is provided as a pyrogen-free composition.

19. The method of claim 3, wherein contacting the protozoan with a hydrophobic signal sequence peptide comprises in vitro, ex vivo, or in vivo contact.

20. The method of claim 19 comprising in vivo contact within the body of a mammalian subject.

21. The method of claim 11, wherein the plasma membrane rigidification results in killing, inhibition of growth, inhibition of reproduction, plasma membrane degradation, and/or constricted cell motility of the bloodstream form of a kinetoplastid protozoan of the genus *Trypanosoma.*

22. The method of claim 11, wherein the trypanosome is selected from the group consisting of *Trypanosoma brucei brucei, T. b. gambiense*, and *T. b. rhodesiense, T. congolense*, and *T. vivax.*

23. The method of claim 11, wherein the hydrophobic signal sequence peptide is provided as a composition further comprising liposome, emulsion, or micelle.

24. The method of claim 11, wherein the hydrophobic signal sequence peptide is provided as a composition further comprising an RNA aptamer that binds to a structurally conserved region of a trypanosome variant surface glycoprotein (VSG).

25. The method of claim 11, wherein the hydrophobic signal sequence peptide is soluble in ethanol or dimethyl sulfoxide (DMSO).

26. The method of claim 11, wherein the hydrophobic signal sequence peptide is provided as a pyrogen-free composition.

27. The method of claim 11, wherein contacting the protozoan with a hydrophobic signal sequence peptide comprises in vitro, ex vivo, or in vivo contact.

28. The method of claim 27 comprising in vivo contact within the body of a mammalian subject.

29. The method of claim 12, wherein the plasma membrane rigidification results in killing, inhibition of growth, inhibition of reproduction, plasma membrane degradation, and/or constricted cell motility of the bloodstream form of a kinetoplastid protozoan of the genus *Trypanosoma.*

30. The method of claim 12, wherein the trypanosome is selected from the group consisting of *Trypanosoma brucei brucei, T. b. gambiense*, and *T. b. rhodesiense, T. congolense*, and *T. vivax.*

31. The method of claim 12, wherein the hydrophobic signal sequence peptide is provided as a composition further comprising liposome, emulsion, or micelle.

32. The method of claim 12, wherein the hydrophobic signal sequence peptide is provided as a composition further comprising an RNA aptamer that binds to a structurally conserved region of a trypanosome variant surface glycoprotein (VSG).

33. The method of claim 12, wherein the hydrophobic signal sequence peptide is soluble in ethanol or dimethyl sulfoxide (DMSO).

34. The method of claim 12, wherein the hydrophobic signal sequence peptide is provided as a pyrogen-free composition.

35. The method of claim 12, wherein contacting the protozoan with a hydrophobic signal sequence peptide comprises in vitro, ex vivo, or in vivo contact.

36. The method of claim 35 comprising in vivo contact within the body of a mammalian subject.

* * * * *

UNITED STATES PATENT AND TRADEMARK OFFICE
CERTIFICATE OF CORRECTION

| | | |
|---|---|---|
| PATENT NO. | : 8,475,767 B2 | Page 1 of 1 |
| APPLICATION NO. | : 13/282623 | |
| DATED | : July 2, 2013 | |
| INVENTOR(S) | : Harrington et al. | |

It is certified that error appears in the above-identified patent and that said Letters Patent is hereby corrected as shown below:

Title page,
Item (73) Assignee:
delete "George" and insert --Georgia--

Signed and Sealed this
Twenty-fifth Day of March, 2014

Michelle K. Lee
*Deputy Director of the United States Patent and Trademark Office*